(12) United States Patent
Lee et al.

(10) Patent No.: US 10,944,059 B2
(45) Date of Patent: Mar. 9, 2021

(54) COMPOUND FOR ORGANIC OPTOELECTRONIC DEVICE, ORGANIC OPTOELECTRONIC DEVICE, AND DISPLAY DEVICE

(71) Applicants: SAMSUNG SDI CO., LTD., Yongin-si (KR); SAMSUNG ELECTRONICS CO., LTD., Suwon-si (KR)

(72) Inventors: Hanill Lee, Suwon-si (KR); Jinseok Hong, Suwon-si (KR); Eun Sun Yu, Suwon-si (KR); Sung-Hyun Jung, Suwon-si (KR); Sujin Han, Suwon-si (KR)

(73) Assignees: SAMSUNG SDI CO., LTD., Yongin-si (KR); SAMSUNG ELECTRONICS CO., LTD., Suwon-si (KR)

( * ) Notice: Subject to any disclaimer, the term of this patent is extended or adjusted under 35 U.S.C. 154(b) by 160 days.

(21) Appl. No.: 16/336,964

(22) PCT Filed: Jun. 30, 2017

(86) PCT No.: PCT/KR2017/006974
§ 371 (c)(1),
(2) Date: Mar. 27, 2019

(87) PCT Pub. No.: WO2018/070641
PCT Pub. Date: Apr. 19, 2018

(65) Prior Publication Data
US 2019/0229275 A1 Jul. 25, 2019

(30) Foreign Application Priority Data
Oct. 12, 2016 (KR) .................. 10-2016-0131991

(51) Int. Cl.
*H01L 51/50* (2006.01)
*H01L 51/00* (2006.01)
(Continued)

(52) U.S. Cl.
CPC ........ *H01L 51/0067* (2013.01); *C07D 307/77* (2013.01); *C07D 333/50* (2013.01);
(Continued)

(58) Field of Classification Search
None
See application file for complete search history.

(56) References Cited

U.S. PATENT DOCUMENTS 7,846,560 B2   12/2010   Nakano et al.

FOREIGN PATENT DOCUMENTS

JP   2002-043061 A   2/2002
KR   10-2012-0072784 A   7/2012
(Continued)

OTHER PUBLICATIONS

International Search Report for PCT/KR2017/006974 filed on Jun. 30, 2017.

*Primary Examiner* — Gregory D Clark
(74) *Attorney, Agent, or Firm* — Lee IP Law, P.C.

(57) ABSTRACT

The present invention relates to a compound represented by Chemical Formula 1 for an organic optoelectronic device, an organic optoelectronic device employing the same and a display device. The details for Chemical Formula 1 above are as defined in the specification.

10 Claims, 1 Drawing Sheet

(51) Int. Cl.
  C07D 409/10    (2006.01)
  C09K 11/02     (2006.01)
  C07D 405/10    (2006.01)
  C07D 409/04    (2006.01)
  C07D 409/14    (2006.01)
  C09K 11/06     (2006.01)
  C07D 405/04    (2006.01)
  C07D 333/50    (2006.01)
  C07D 307/77    (2006.01)
  C07D 405/14    (2006.01)
  H01L 51/52     (2006.01)
  H01L 51/56     (2006.01)

(52) U.S. Cl.
  CPC ......... *C07D 405/04* (2013.01); *C07D 405/10* (2013.01); *C07D 405/14* (2013.01); *C07D 409/04* (2013.01); *C07D 409/10* (2013.01); *C07D 409/14* (2013.01); *C09K 11/025* (2013.01); *C09K 11/06* (2013.01); *H01L 51/00* (2013.01); *H01L 51/0073* (2013.01); *H01L 51/0074* (2013.01); *H01L 51/001* (2013.01); *H01L 51/5012* (2013.01); *H01L 51/5016* (2013.01); *H01L 51/5064* (2013.01); *H01L 51/5072* (2013.01); *H01L 51/5096* (2013.01); *H01L 51/5206* (2013.01); *H01L 51/5221* (2013.01); *H01L 51/56* (2013.01); *H01L 2251/301* (2013.01); *H01L 2251/308* (2013.01); *H01L 2251/558* (2013.01)

(56) References Cited

FOREIGN PATENT DOCUMENTS

| | | | | |
|---|---|---|---|---|
| KR | 10-2013-0067274 A | 6/2013 | | |
| KR | 10-2015-0003599 A | 1/2015 | | |
| KR | 10-2015-0007139 | * 1/2015 | ............ | C09K 11/06 |
| KR | 10-2015-0007139 A | 1/2015 | | |
| KR | 10-1627761 B1 | 5/2016 | | |
| WO | WO 2013/001997 A1 | 1/2013 | | |

* cited by examiner

【Figure 1】
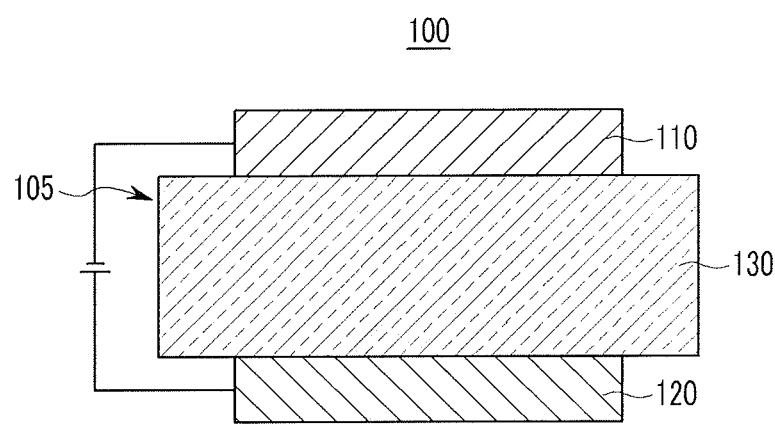
【Figure 2】
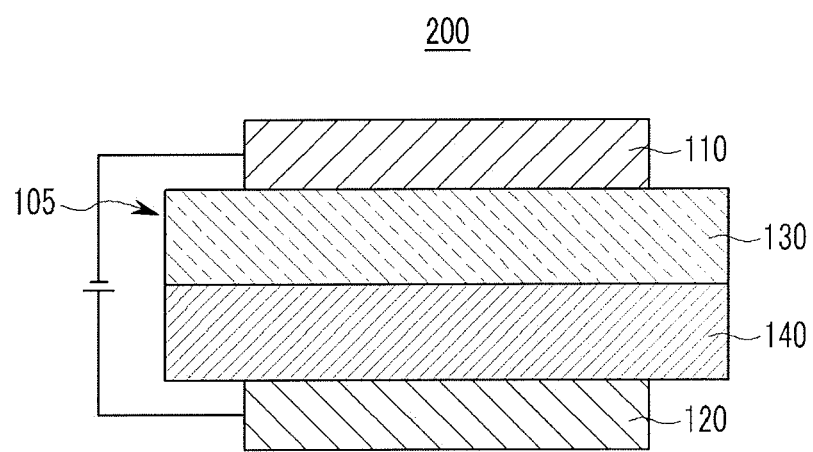

COMPOUND FOR ORGANIC OPTOELECTRONIC DEVICE, ORGANIC OPTOELECTRONIC DEVICE, AND DISPLAY DEVICE

CROSS-REFERENCE TO THE RELATED APPLICATION

This is the U.S. national phase application based on PCT Application No. PCT/KR2017/006974, filed Jun. 30, 2017, which is based on Korean Patent Application No. 10-2016-0131991, filed Oct. 12, 2016, the entire contents of all of which are hereby incorporated by reference.

TECHNICAL FIELD

A compound for an organic optoelectronic device, an organic optoelectronic device, and a display device are disclosed.

BACKGROUND ART

An organic optoelectronic device is an device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying a current to an organic light emitting material, and has a structure in which an organic layer is disposed between an anode and a cathode. Herein, the organic layer may include a light emitting layer and optionally an auxiliary layer, and the auxiliary layer may be for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material capable of increasing hole and electron mobility and simultaneously increasing electrochemical stability is needed so that the organic light emitting diode may be applied to a large-size flat panel display.

DISCLOSURE

Technical Problem

An embodiment provides a compound for an organic optoelectronic device capable of realizing high efficiency and long life-organic optoelectronic device.

Technical Solution

Another embodiment provides an organic optoelectronic device including the compound.

Yet another embodiment provides a display device including the organic optoelectronic device.

According to an embodiment, a compound for an organic optoelectronic device represented by Chemical Formula 1 is provided.

[Chemical Formula 1]

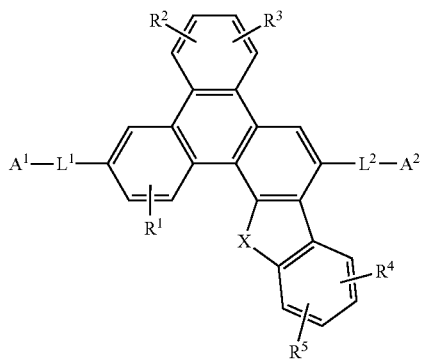

In Chemical Formula 1,

X is O or S, $R^1$ to $R^5$ are independently hydrogen, deuterium, a substituted or unsubstituted C1 to C5 alkyl group, or a substituted or unsubstituted C6 to C18 aryl group, $L^1$ and $L^2$ are independently a single bond, a substituted or unsubstituted C6 to C20 arylene group, or a substituted or unsubstituted C2 to C30 heteroarylene group, $A^1$ and $A^2$ are independently hydrogen, deuterium, a substituted or unsubstituted C6 to C18 aryl group, or a substituted or unsubstituted C2 to C30 heterocyclic group, and at least one of $A^1$ and $A^2$ includes a moiety represented by Chemical Formula A,

[Chemical Formula A]

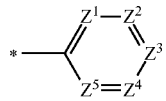

wherein, in Chemical Formula A, $Z^1$ to $Z^5$ are independently N or $CR^a$, at least one of $Z^1$ to $Z^5$ is N, $R^a$ is independently hydrogen, deuterium, a substituted or unsubstituted C1 to C5 alkyl group, or a substituted or unsubstituted C6 to C18 aryl group.

$R^a$ is independently present or adjacent groups thereof are linked with each other to form a substituted or unsubstituted aliphatic, aromatic or heteroaromatic monocyclic or polycyclic ring, m and n are independently one of integers of 0 to 2, \* is a linking point with $L^1$ or $L^2$ of Chemical Formula 1, the "substituted" refers to replacement of at least one hydrogen by deuterium, a cyano group, a C1 to C20 alkyl group, a C6 to C30 aryl group, or a C2 to C30 heteroaryl group.

According to another embodiment, an organic optoelectronic device includes an anode and a cathode facing each other and at least one organic layer disposed between the anode and the cathode, wherein the organic layer includes the compound for an organic optoelectronic device.

According to another embodiment, a display device including the organic optoelectronic device is provided.

Advantageous Effects

An organic optoelectronic device having high efficiency and a long life-span may be realized.

DESCRIPTION OF THE DRAWINGS

FIGS. 1 and 2 are cross-sectional views showing organic light emitting diodes according to embodiments.

DESCRIPTION OF SYMBOLS

100, 200: organic light emitting diode
105: organic layer
110: cathode
120: anode
130: light emitting layer
140: hole auxiliary layer

MODE FOR INVENTION

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, the "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in specific examples of the present invention, "substituted" refers to replacement of at least one hydrogen of a substituent or a compound by deuterium, a C1 to C20 alkyl group, a C6 to C30 aryl group, or a C2 to C30 heteroaryl group. In addition, in specific examples of the present invention, "substituted" refers to replacement of at least one hydrogen of a substituent or a compound by deuterium, a C1 to C5 alkyl group, a C6 to C18 aryl group, a pyridinyl group, a pyrimidinyl group, a triazinyl group, a quinolinyl group, an isoquinolinyl group, a quinazolinyl group, a benzoquinolinyl group, a benzoisoquinolinyl group, or a benzoquinazolinyl group. In addition, in specific examples of the present invention, "substituted" refers to replacement of at least one hydrogen of a substituent or a compound by deuterium, a methyl group, an ethyl group, a propanyl group, a butyl group, a phenyl group, a biphenyl group, a terphenyl group, a naphthyl group, a triphenyl group, a pyridinyl group, a pyrimidinyl group, a triazinyl group, a quinolinyl group, an isoquinolinyl group, a quinazolinyl group, a benzoquinolinyl group, a benzoisoquinolinyl group, or a benzoquinazolinyl group.

In the present specification, when a definition is not otherwise provided, "hetero" refers to one including one to three heteroatoms selected from N, O, S, P, and Si, and remaining carbons in one functional group.

In the present specification, when a definition is not otherwise provided, "an alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, a quinazolinyl group, a benzoquinolinyl group, a benzoisoquinolinyl group, a benzoquinazolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinazolinyl group, a substituted or unsubstituted benzoquinolinyl group, a substituted or unsubstituted benzoisoquinolinyl group, a substituted or unsubstituted benzoquinazolinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

Hereinafter, a compound for an organic optoelectronic device according to an embodiment is described.

A compound for an organic optoelectronic device according to an embodiment is represented by Chemical Formula 1.

[Chemical Formula 1]

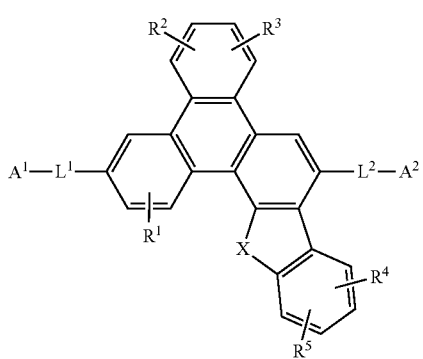

In Chemical Formula 1,
X is O or S,
$R^1$ to $R^5$ are independently hydrogen, deuterium, a substituted or unsubstituted C1 to C5 alkyl group, or a substituted or unsubstituted C6 to C18 aryl group,
$L^1$ and $L^2$ are independently a single bond, a substituted or unsubstituted C6 to C20 arylene group, or a substituted or unsubstituted C2 to C30 heteroarylene group, $A^1$ and $A^2$ are independently hydrogen, deuterium, a substituted or unsubstituted C6 to C18 aryl group, or a substituted or unsubstituted C2 to C30 heterocyclic group, and at least one of $A^1$ and $A^2$ includes a moiety represented by Chemical Formula A,

[Chemical Formula A]

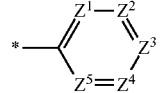

wherein, in Chemical Formula A,
$Z^1$ to $Z^5$ are independently N or $CR^a$,
at least one of $Z^1$ to $Z^5$ is N,
$R^a$ are independently hydrogen, deuterium, a substituted or unsubstituted C1 to C5 alkyl group, or a substituted or unsubstituted C6 to C18 aryl group,
$R^a$ is independently present or adjacent groups thereof are linked with each other to form a substituted or unsubstituted aliphatic, aromatic or heteroaromatic monocyclic or polycyclic ring, and
* is a linking point with $L^1$ or $L^2$ of Chemical Formula 1,
wherein the "substituted" refers to replacement of at least one hydrogen by deuterium, a cyano group, a C1 to C20 alkyl group, a C6 to C30 aryl group, or a C2 to C30 heteroaryl group. In specific examples of the present invention, the "substituted" refers to replacement of at least one hydrogen by deuterium, a C1 to C20 alkyl group, a C6 to C30 aryl group, a pyridinyl group, a pyrimidinyl group, a triazinyl group, a quinolinyl group, an isoquinolinyl group, a quinazolinyl group, a benzoquinolinyl group, a benzoisoquinolinyl group, or a benzoquinazolinyl.

For example, the "substituted" refers to replacement of at least one hydrogen by deuterium, a phenyl group, a biphenyl group, a naphthyl group, a pyridinyl group, a pyrimidinyl group, a triazinyl group, a quinolinyl group, an isoquinolinyl group, a quinazolinyl group, a benzoquinolinyl group, a benzoisoquinolinyl group, or a benzoquinazolinyl group.

The present invention provides a compound for an organic optoelectronic device in which an ET unit (electron transfer unit), that is, a compound having a high electron mobility, is linked with a compound in which triphenylenes, benzofurans, or benzothiophenes are fused, a device having long life-span, low driving, and high efficiency may be implemented.

The compound according to the present invention includes benzofuran or benzothiophene which is fused with triphenylene, and thereby a glass transition temperature (Tg) may be increased and stability of the compound may be increased and degradation thereof may be prevented during processes applied to a device. The glass transition temperature (Tg) may have a relation with thermal stability of a compound and a device including the same. That is, a compound for an organic optoelectronic device having a high glass transition temperature (Tg) is applied to an organic light emitting diode in a thin film form, subsequent processes after depositing the compound for an organic optoelectronic device, for example in an encapsulation process, degradation by a temperature may be prevented and thus life-span characteristics of an organic compound and a device may be ensured.

In addition, since a LUMO electron cloud of the ET group may be extended to triphenylene by substituting the triphenylenem moiety with the ET unit, a LUMO energy level may be relatively lowered than a compound including a benzofuran (or benzothiophene) moiety substituted with the ET group. Since it may interact with the electrode due to a polar group of nitrogen included in the ET unit, charge injection may be easy and mobility is high, so that a low driving voltage may be realized.

In addition, due to the steric hindrance of the molecular structure, an intermolecular interaction may be reduced and crystallization may be suppressed, so that improvement of a yield and a long life-span of an organic light emitting diode including the same may be ensured.

In an embodiment of the present invention, $A^1$ and $A^2$ may independently be hydrogen, deuterium, a substituted or unsubstituted C6 to C18 aryl group, or a substituted or unsubstituted C2 to C30 heterocyclic group and at least one of $A^1$ and $A^2$ may be represented by Chemical Formula A.

In an embodiment of the present invention, in Chemical Formula A, at least two of $Z^1$ to $Z^5$ may be N.

Chemical Formula A may be specifically represented by one of Chemical Formula A1, Chemical Formula A2, Chemical Formula A3, and Chemical Formula A4.

[Chemical Formula A1]

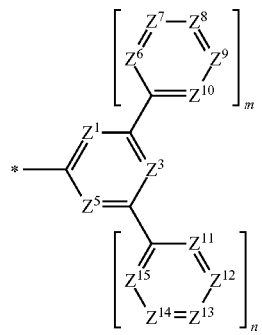

[Chemical Formula A2]

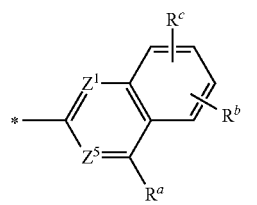

[Chemical Formula A3]

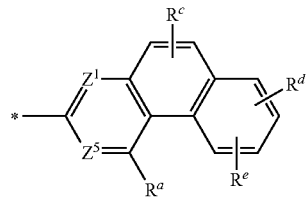

[Chemical Formula A4]

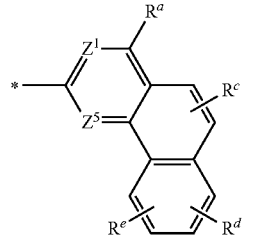

In Chemical Formula A1 to Chemical Formula A4,
$Z^1$, $Z^3$, $Z^5$, and $Z^6$ to $Z^5$ are independently N or $CR^a$,
at least one of $Z^1$, $Z^3$, $Z^5$, and $Z^6$ to $Z^5$ of Chemical Formula A1 is N, at least one of $Z^1$ and $Z^5$ of Chemical Formulae A2 to A4 is N, m and n are independently one of integers of 0 to 2, $R^a$ to $R^e$ are independently hydrogen, deuterium, a substituted or unsubstituted C1 to C5 alkyl group, or a substituted or unsubstituted C6 to C18 aryl group, and

* is a linking point with $L^1$ or $L^2$ of Chemical Formula 1.

In a specific embodiment of the present invention, at least two of $Z^1$, $Z^3$, $Z^5$, and $Z^6$ to $Z^{15}$ of Chemical Formula A1 may be N.

In another specific embodiment of the present invention, at least two of $Z^1$ and $Z^5$ of Chemical Formula A2 to A4 may be N.

Chemical Formula A may be for example as an ET unit, a substituted phenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted benzoquinolinyl group, a substituted or unsubstituted benzoisoquinolinyl group, or a substituted or unsubstituted benzoquinazolinyl group. Herein, "substituted" refers to replacement of at least one hydrogen by a phenyl group, a biphenyl group, a naphthyl group, a pyridinyl group, or a pyrimidinyl group.

On the other hand, the ET unit may refer to an N-containing hexagonal ring moiety except a carbazolyl group and may be a pyridinyl group, a pyrimidinyl group, a triazinyl group, a quinolinyl group, an isoquinolinyl group, a quinazolinyl group, a benzoquinolinyl group, a benzoisoquinolinyl group, a benzoquinazolinyl group, and the like. More specifically, it may be a pyridinyl group, a triazinyl group, a quinazolinyl group, or a benzoquinazolinyl group.

In a specific embodiment of the present invention, Chemical Formula A may be selected from substituents of Group I.

[Group 1]

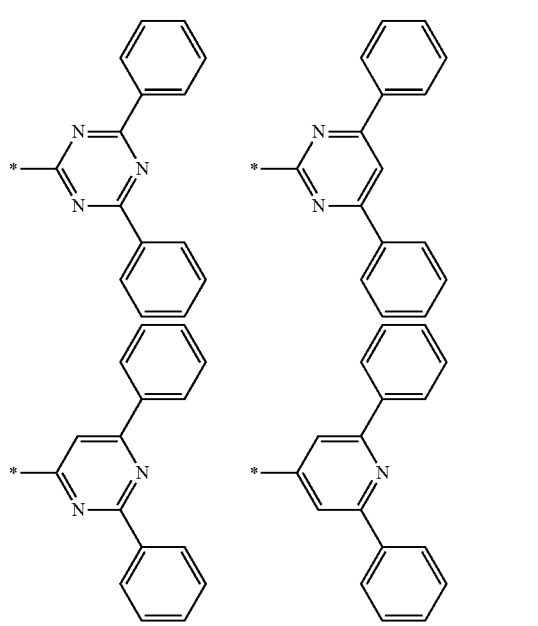

-continued
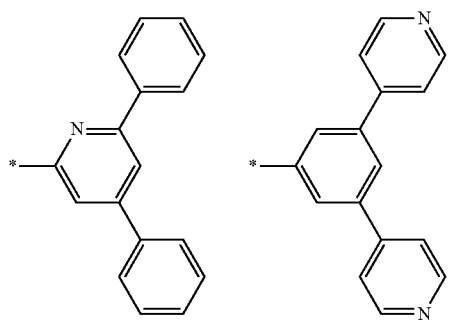 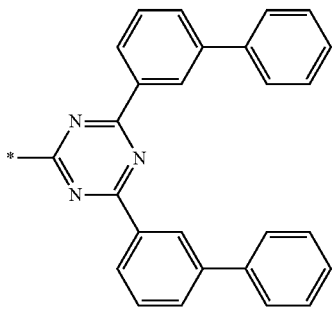
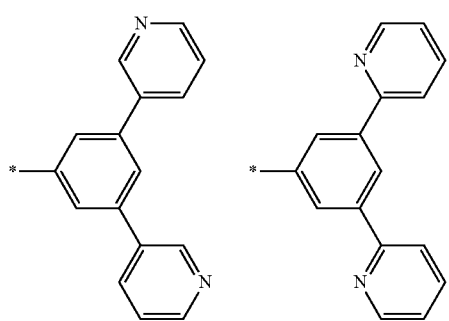 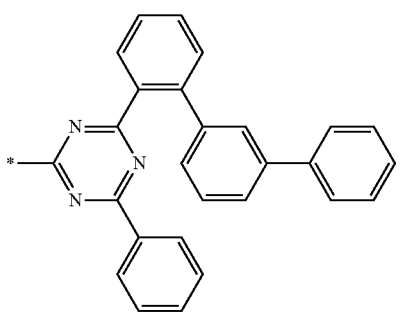
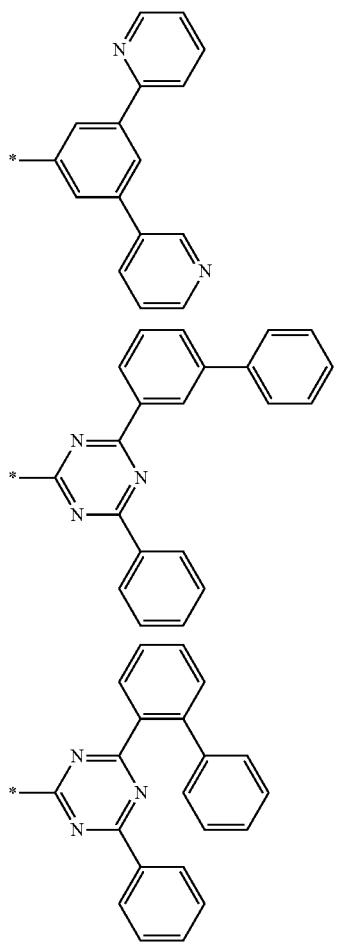
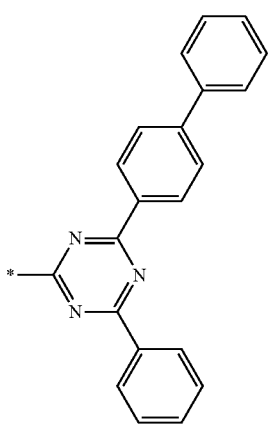

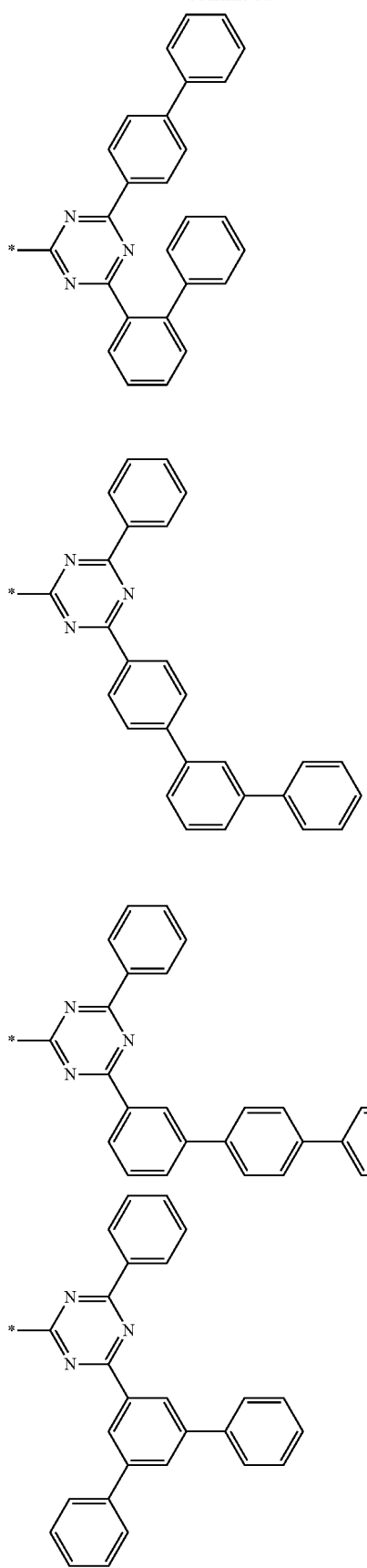

-continued

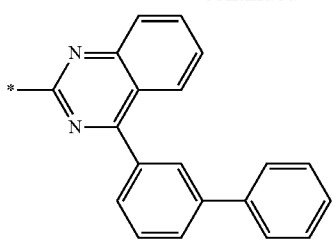

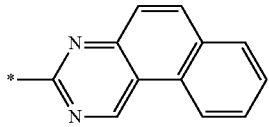

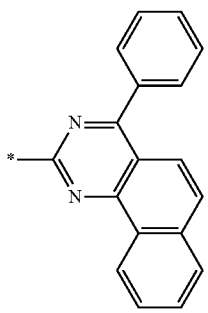

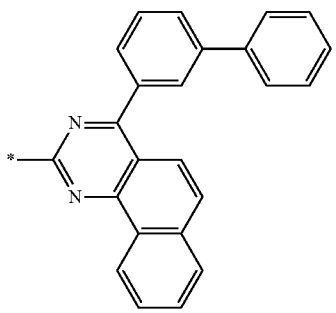

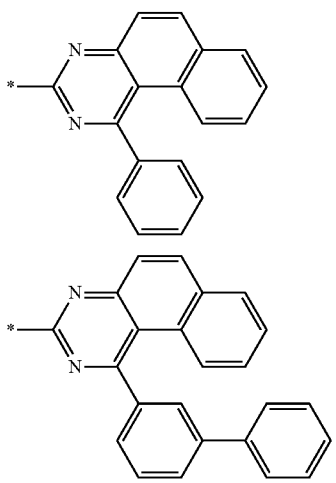

In Group I, * is a linking point with $L^1$ or $L^2$ of Chemical Formula 1.

In the most specific embodiment of the present invention, Chemical Formula A may be a substituted or unsubstituted pyrimidinyl group, a substituted or unsubstituted triazinyl group, a substituted or unsubstituted quinazolinyl group, or a substituted or unsubstituted benzoquinazolinyl group.

On the other hand, Chemical Formula 1 may be for example represented by Chemical Formula 1-I, or Chemical Formula 1-11 according to a substitution position of Chemical Formula A.

[Chemical Formula 1-I]

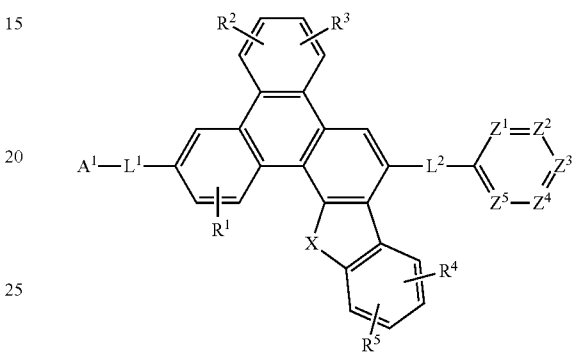

[Chemical Formula 1-II]

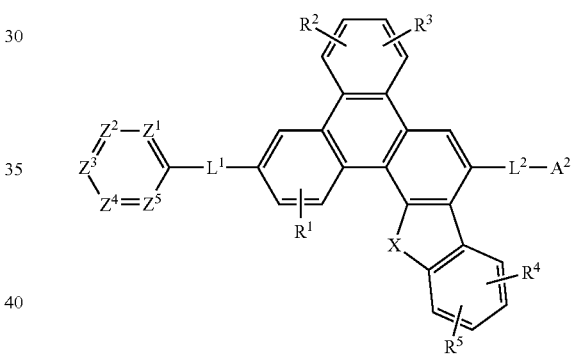

In Chemical Formula 1-I and Chemical Formula 1-II, $A^1$ and $A^2$, X, $Z^1$ to $Z^5$, $R^1$ to $R^5$ and $L^1$ and $L^2$ are the same as described above, $A^1$ and $A^2$ of Chemical Formula 1-I and Chemical Formula 1-II may independently be hydrogen, deuterium, or a substituted or unsubstituted C6 to C18 aryl group. Specifically, they may be hydrogen, deuterium, a substituted or unsubstituted phenyl group, a substituted or unsubstituted biphenyl group, or a substituted or unsubstituted naphthyl group, and more specifically hydrogen or a phenyl group.

In an embodiment of the present invention, $L^1$ and $L^2$ may independently be a single bond, or a substituted or unsubstituted C6 to C20 arylene group, specifically a single bond, or a substituted or unsubstituted C6 to C18 arylene group, and for example a single bond, a substituted or unsubstituted phenylene group, or a substituted or unsubstituted biphenylene group.

In a specific embodiment of the present invention, $R^a$ may be hydrogen, or a substituted or unsubstituted C6 to C18 aryl group, and $R^a$ may independently be present and thus Chemical Formula 1 may be for example represented by one of Chemical Formula 1-A1-a1, Chemical Formula 1-A1-a2, Chemical Formula 1-A1-b1, and Chemical Formula 1-A1-b2.

[Chemical Formula 1-A1-a1]

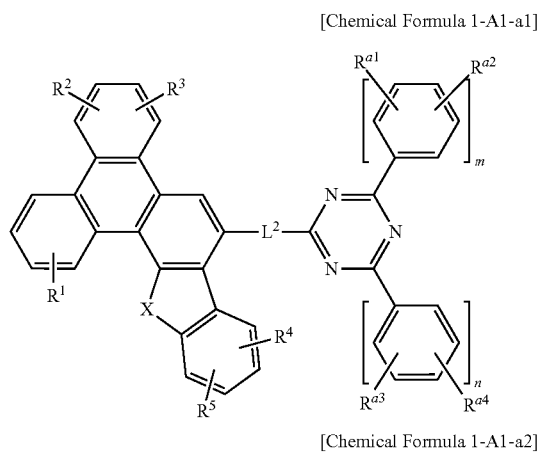

[Chemical Formula 1-A1-a2]

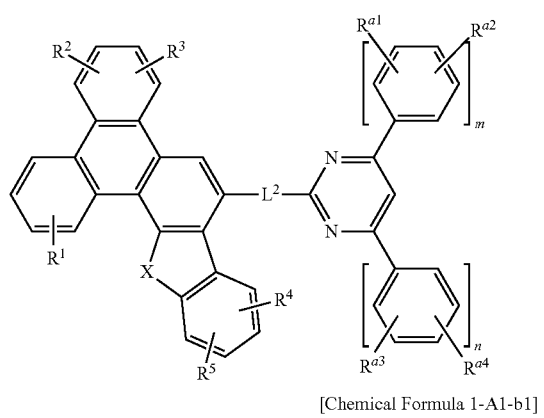

[Chemical Formula 1-A1-b1]

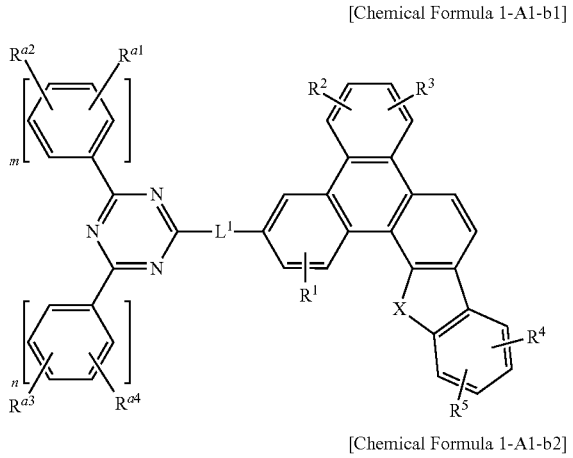

[Chemical Formula 1-A1-b2]

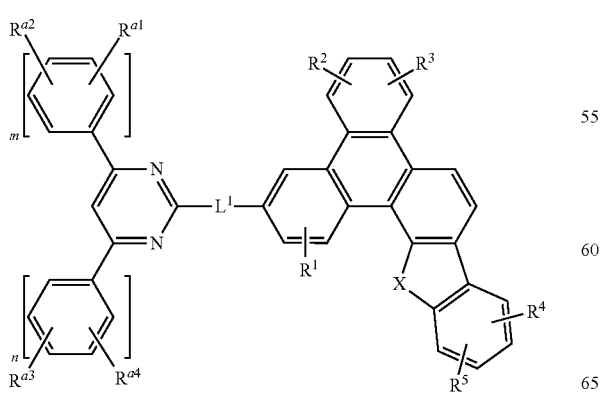

In Chemical Formula Chemical Formula 1-A1-a1, Chemical Formula 1-A1-a2, Chemical Formula 1-A1-b1, and Chemical Formula 1-A1-b2, X, $L^1$ and $L^2$, $R^1$ to $R^5$, m, and n are the same as described above, $R^{a1}$ to $R^{a4}$ may independently be hydrogen, deuterium, a substituted or unsubstituted C1 to C5 alkyl group, or a substituted or unsubstituted C6 to C12 aryl group, specifically hydrogen, deuterium, a substituted or unsubstituted C1 to C5 alkyl group, or a substituted or unsubstituted phenyl group, a substituted or unsubstituted biphenyl group, for example, hydrogen, a phenyl group, or a biphenyl group.

In addition, adjacent groups of $R^a$'s may be linked with each other to form a substituted or unsubstituted aliphatic, aromatic or heteroaromatic monocyclic or polycyclic ring.

The "linking of the adjacent groups" means that the phenyl group linked with $R^a$ is fused with any two adjacent substituents of $R^a$ to form a substituted or unsubstituted aliphatic, aromatic or heteroaromatic monocyclic ring or a substituted or unsubstituted aliphatic, aromatic or heteroaromatic polycyclic ring. Examples of the heteroaromatic polycyclic ring may be a substituted or unsubstituted quinolinyl group, a substituted or unsubstituted isoquinolinyl group, a substituted or unsubstituted quinazolinyl group, a substituted or unsubstituted benzoquinolinyl group, a substituted or unsubstituted benzoisoquinolinyl group, a substituted or unsubstituted benzoquinazolinyl group, and the like, and may be for example may be represented by one of Chemical Formula 1-A2-a, Chemical Formula 1-A2-b, Chemical Formula 1-A3-a, Chemical Formula 1-A3-b, Chemical Formula 1-A4-a, and Chemical Formula 1-A4-b.

[Chemical Formula 1-A2-a]

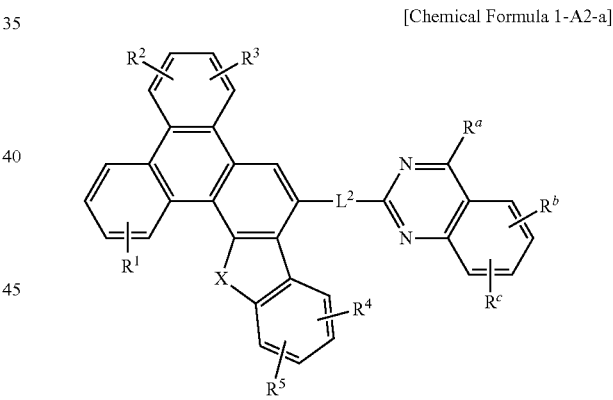

[Chemical Formula 1-A2-b]

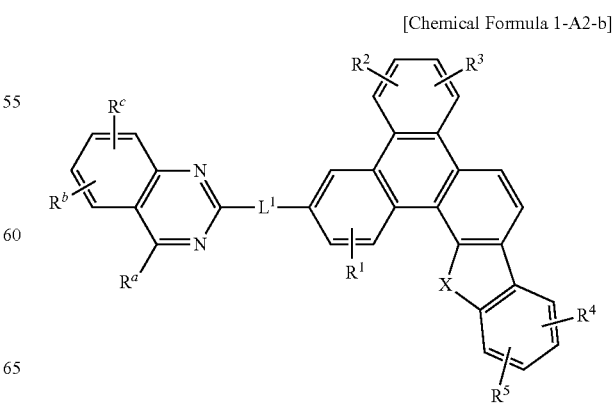

[Chemical Formula 1-A3-a]

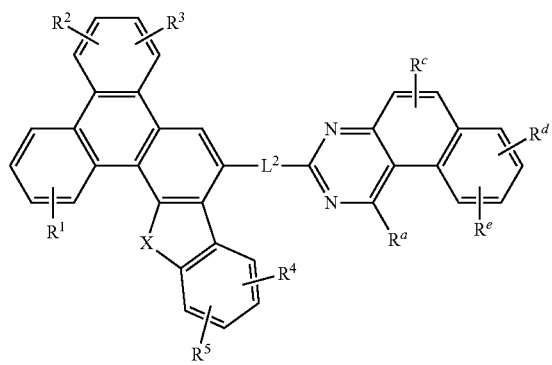

[Chemical Formula 1-A3-b]

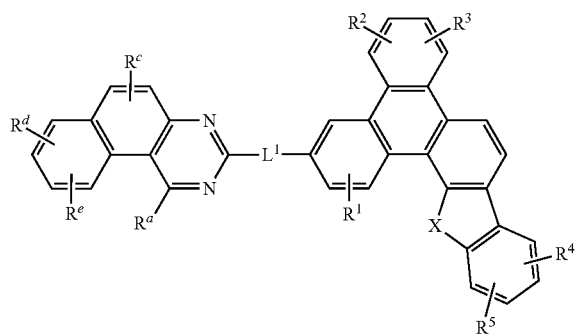

[Chemical Formula 1-A4-a]

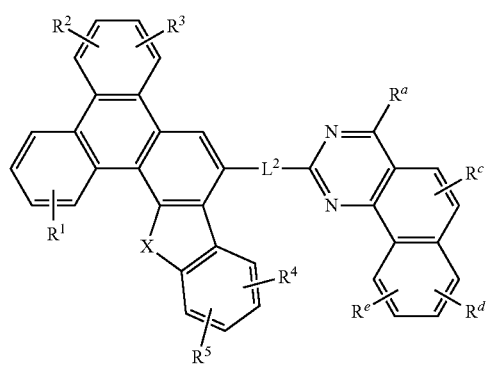

[Chemical Formula 1-A4-b]

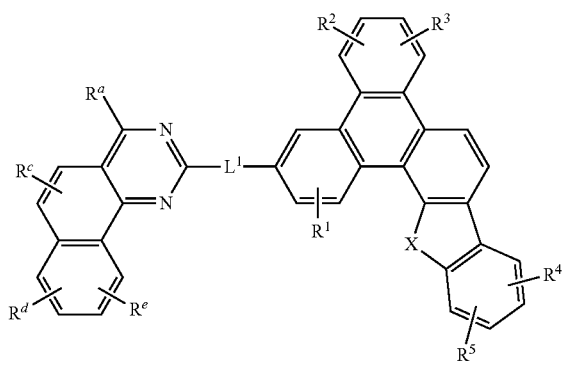

In Chemical Formula 1-A2-a, Chemical Formula 1-A2-b, Chemical Formula 1-A3-a, Chemical Formula 1-A3-b, Chemical Formula 1-A4-a, and Chemical Formula 1-A4-b, X, $L^1$ and $L^2$ and $R^1$ to $R^5$ are the same as described above, $R^a$ to $R^e$ may independently be hydrogen, deuterium, a substituted or unsubstituted C1 to C5 alkyl group, or a substituted or unsubstituted C6 to C12 aryl group, specifically hydrogen, deuterium, a substituted or unsubstituted C1 to C5 alkyl group, or a substituted or unsubstituted phenyl group, or a substituted or unsubstituted biphenyl group, for example, hydrogen, a phenyl group, or a biphenyl group.

In an embodiment of the present invention, $R^1$ to $R^5$ may be hydrogen, deuterium, or a substituted or unsubstituted C6 to C12 aryl group, specifically, hydrogen, a substituted or unsubstituted phenyl group, a substituted or unsubstituted biphenyl group, or a substituted or unsubstituted naphthyl group. For example, $R^1$ to $R^5$ may be all hydrogen or one of $R^1$ to $R^5$ may be a phenyl group or a naphthyl group.

The compound for an organic optoelectronic device according to a specific embodiment of the present invention may be represented by one of Chemical Formula 1-A1-a1, Chemical Formula 1-A1-a2, Chemical Formula 1-A1-b1, Chemical Formula 1-A1-b2, Chemical Formula 1-A2-a. Chemical Formula 1-A2-b, Chemical Formula 1-A4-a, and Chemical Formula 1-A4-b, and the most specifically may be represented by one of Chemical Formula 1-A1-a1, Chemical Formula 1-A1-a2, Chemical Formula 1-A2-a, and Chemical Formula 1-A4-a.

The compound for an organic optoelectronic device represented by Chemical Formula 1 may be for example selected from compounds of Group 1, but is not limited thereto.

[Group 1]

[A-1]

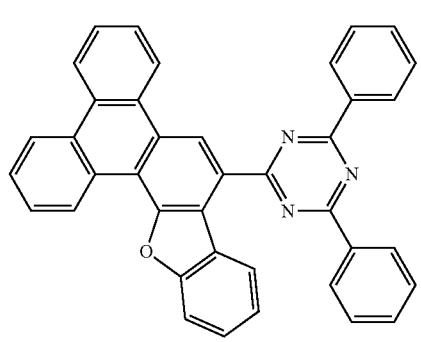

[A-2]

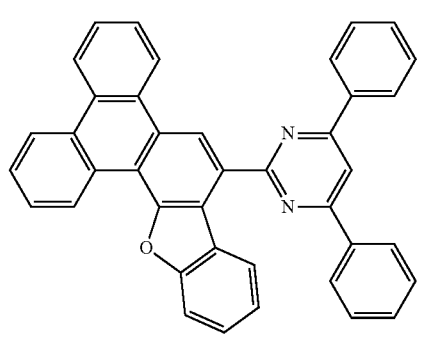

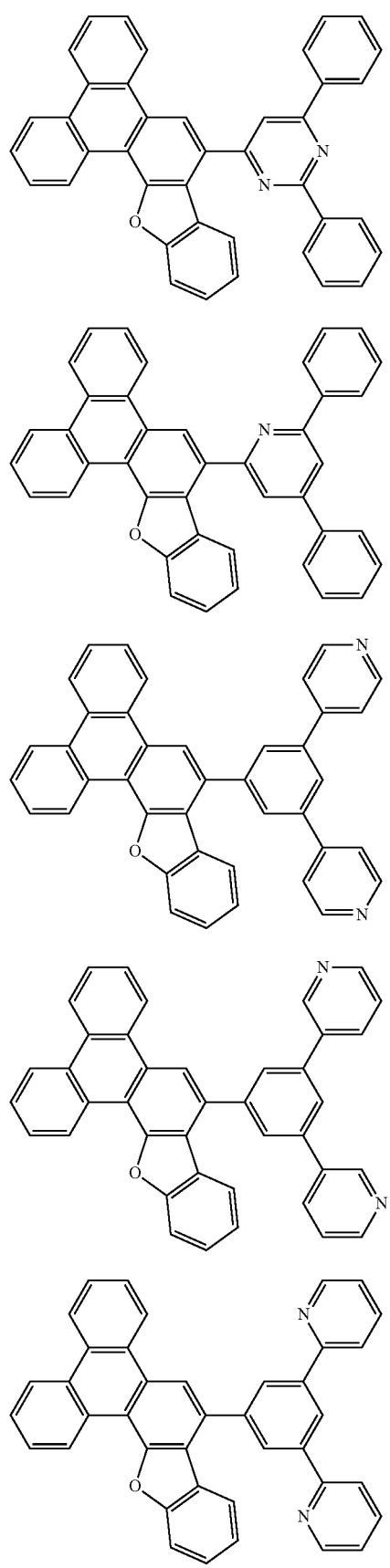
[A-3]
[A-4]
[A-5]
[A-6]
[A-7]
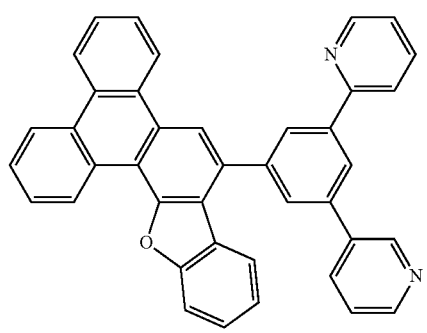
[A-8]
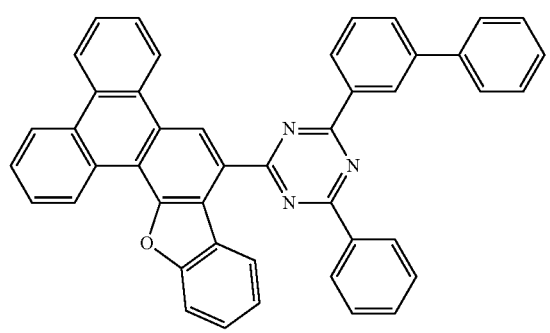
[A-9]
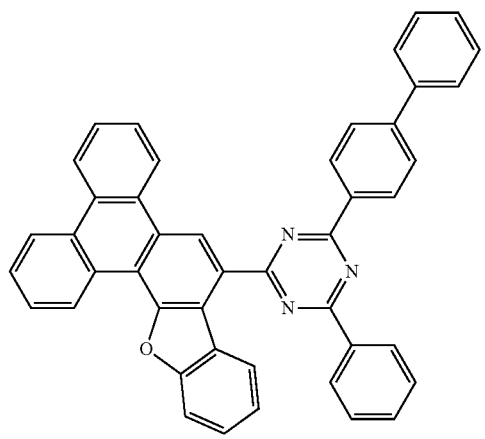
[A-10]
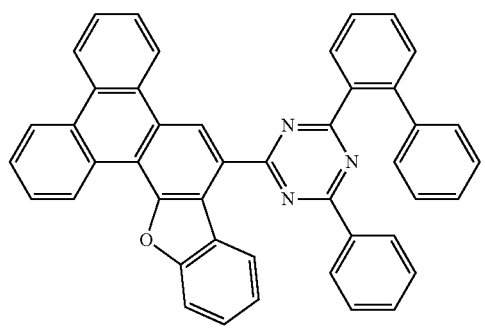
[A-11]

[A-12]
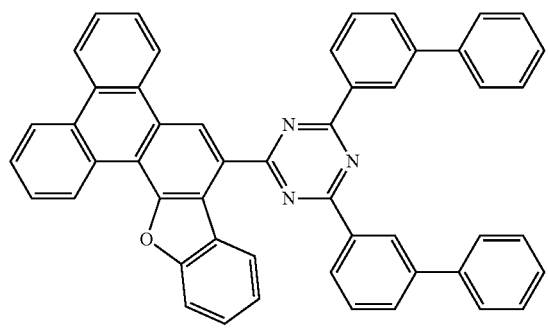
[A-13]
[A-14]
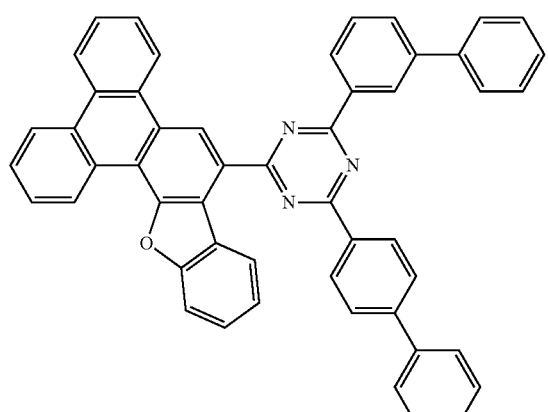
[A-15]
[A-16]
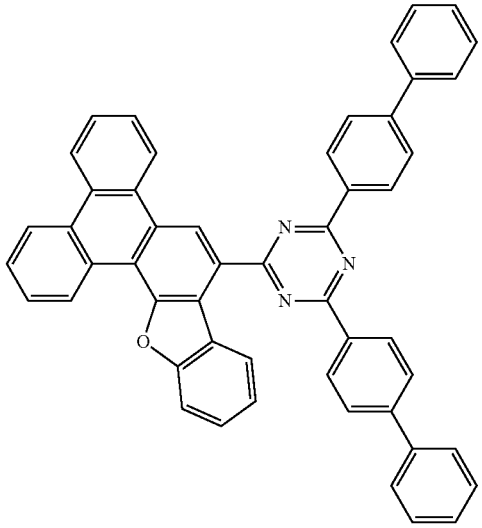
[A-17]
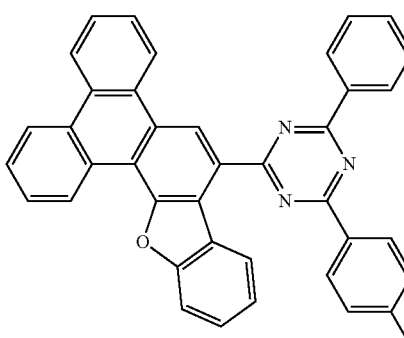
[A-18]
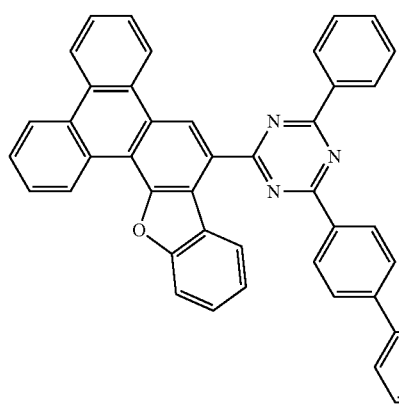

-continued
[A-19]
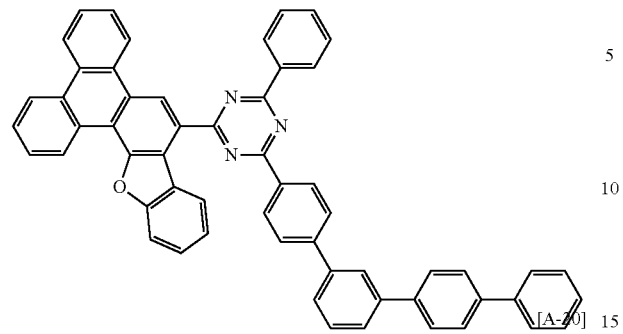
[A-20]
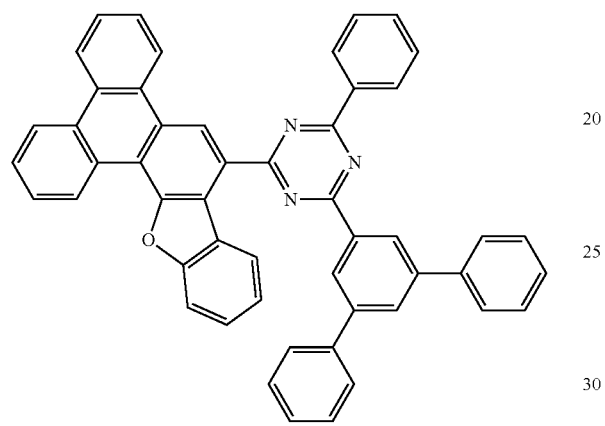
[A-21]
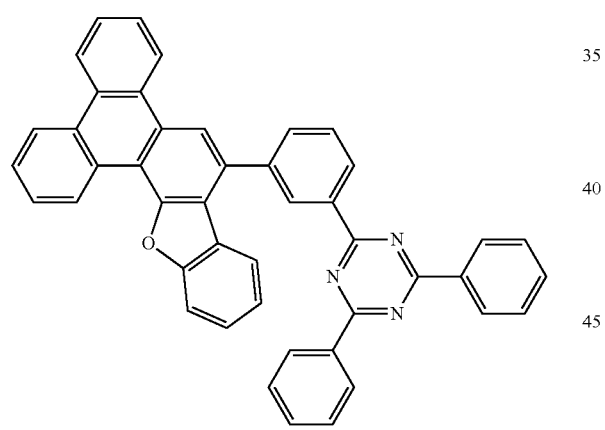
[A-22]
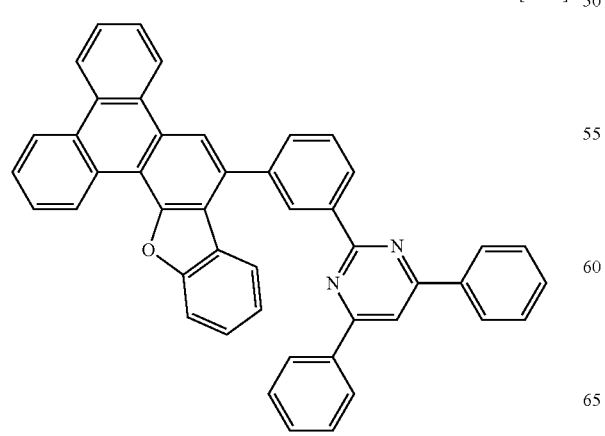
-continued
[A-23]
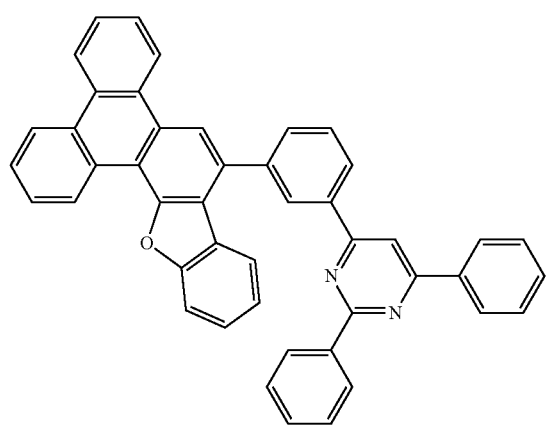
[A-24]
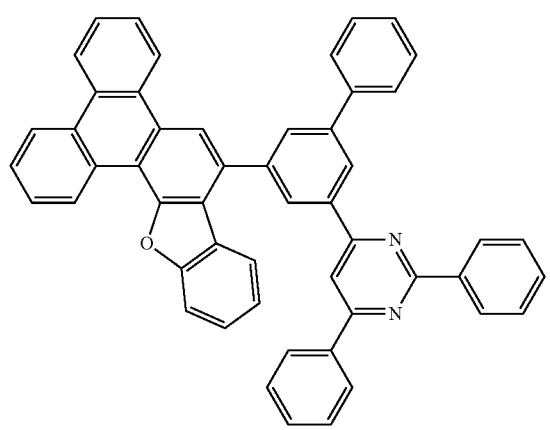
[A-25]

-continued
[A-26]
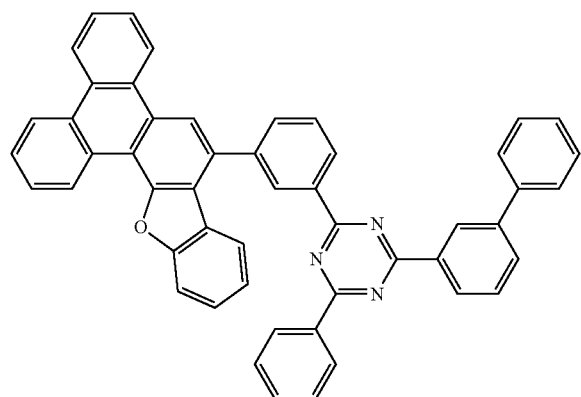
[A-27]
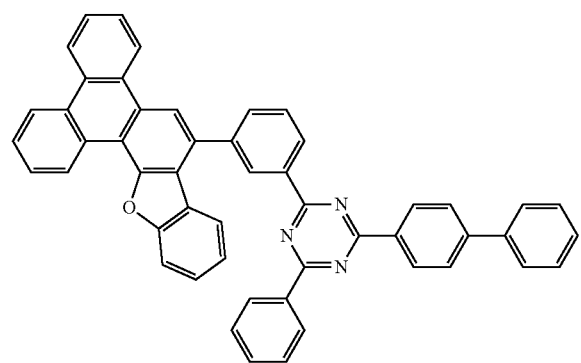
[A-28]
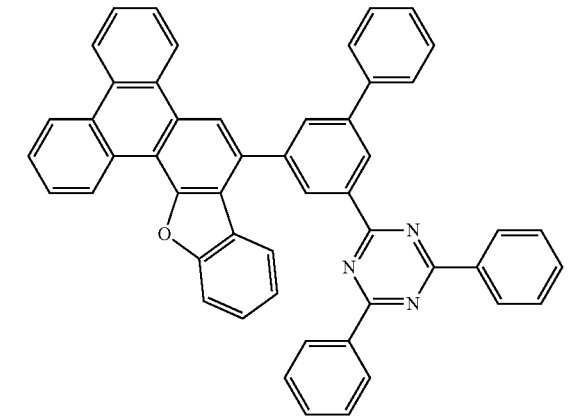
[A-29]
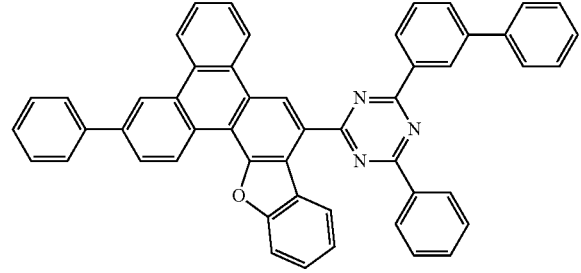
[A-30]
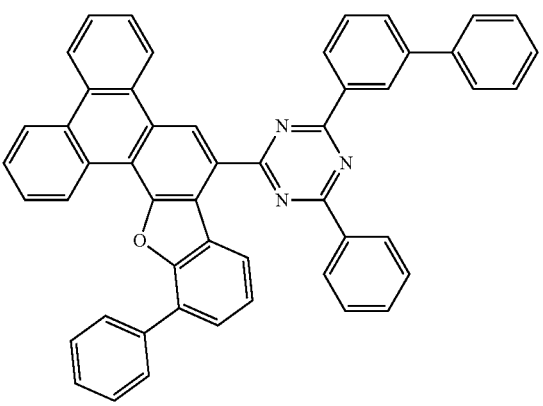
[A-31]
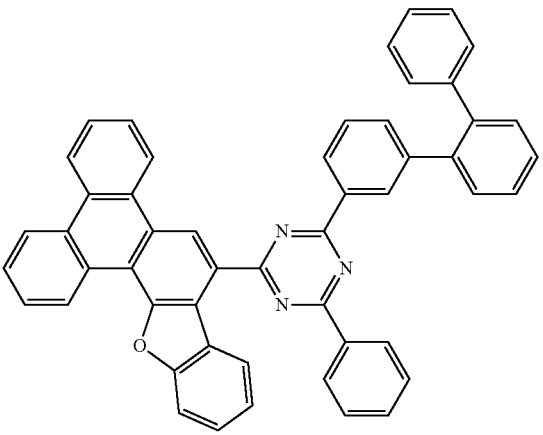
[A-32]
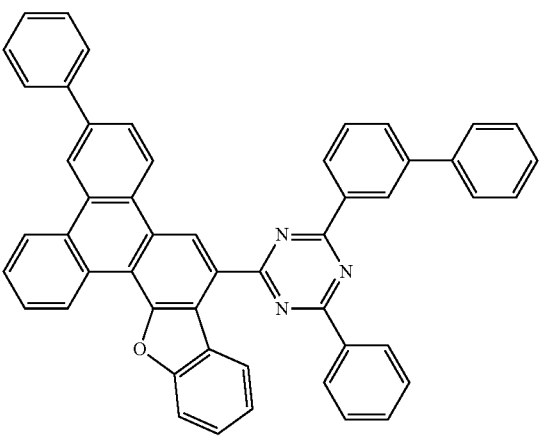
[A-33]
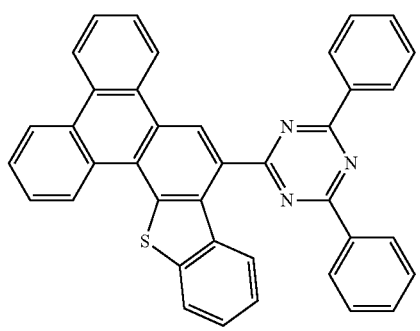

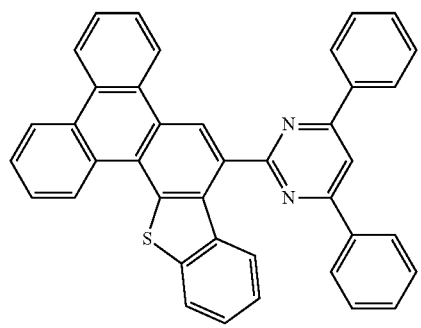
[A-34]
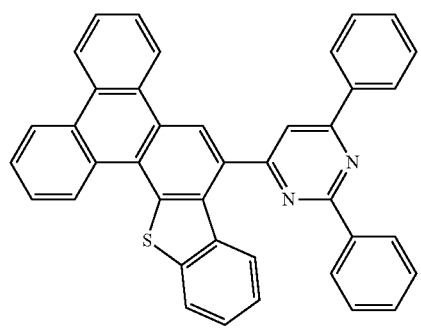
[A-35]
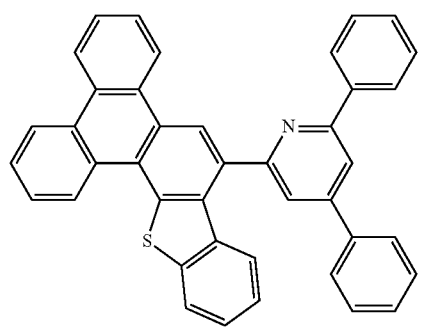
[A-36]
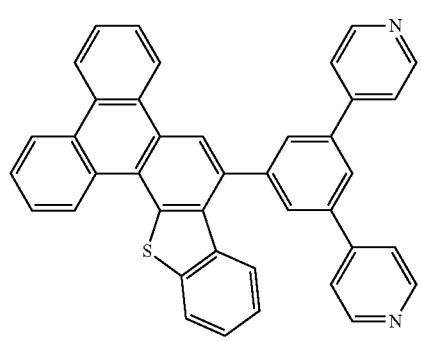
[A-37]
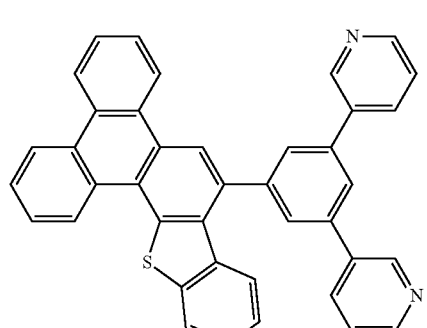
[A-38]
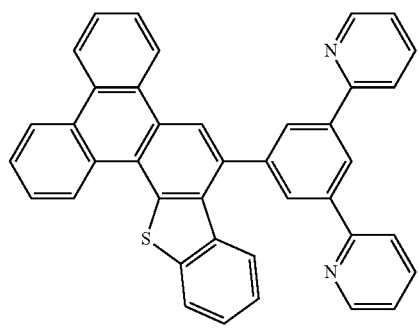
[A-39]
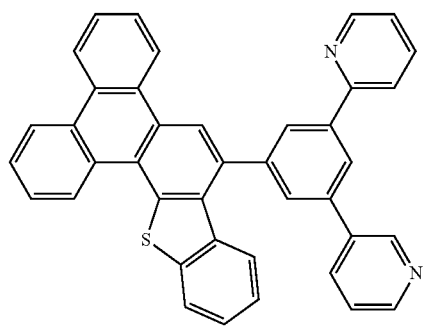
[A-40]
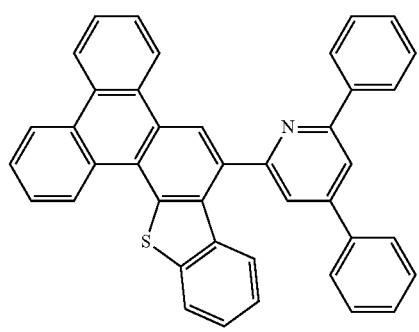
[A41]
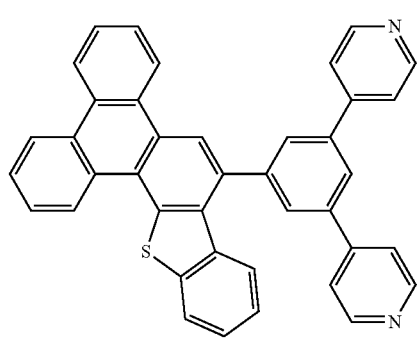
[A42]
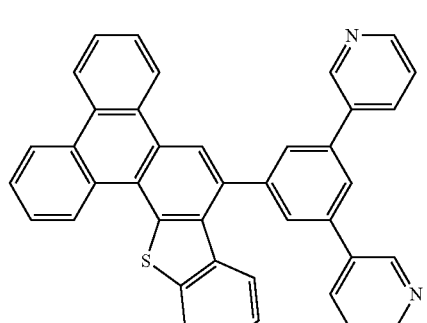
[A-43]

[A-44]
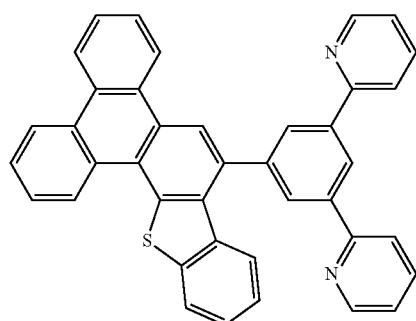
[A-48]
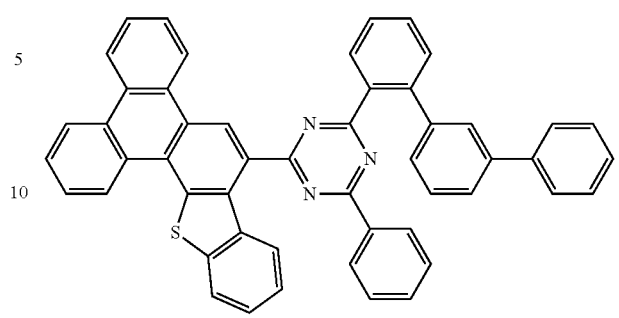
[A-45]
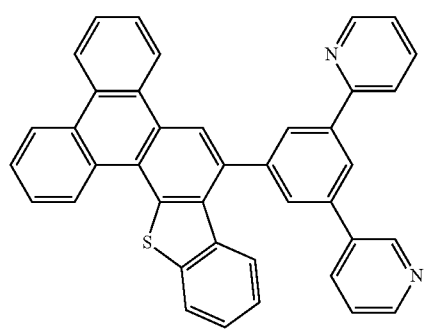
[A-49]
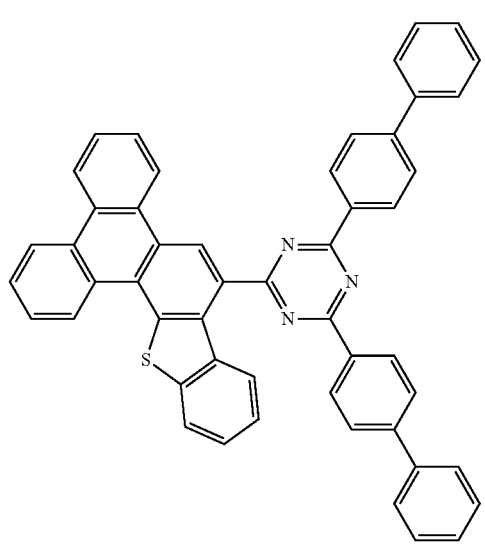
[A-46]
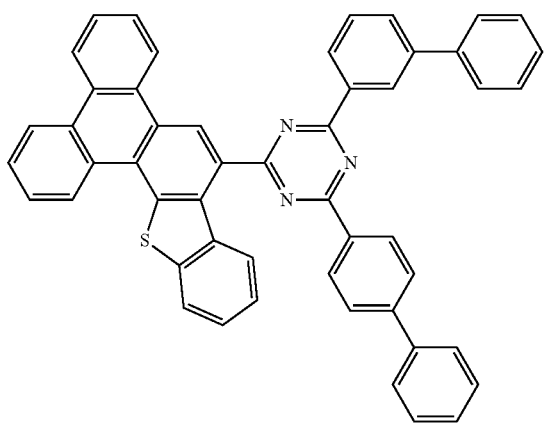
[A-50]
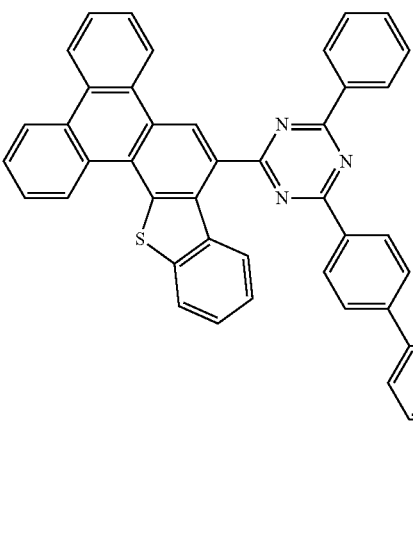
[A-47]
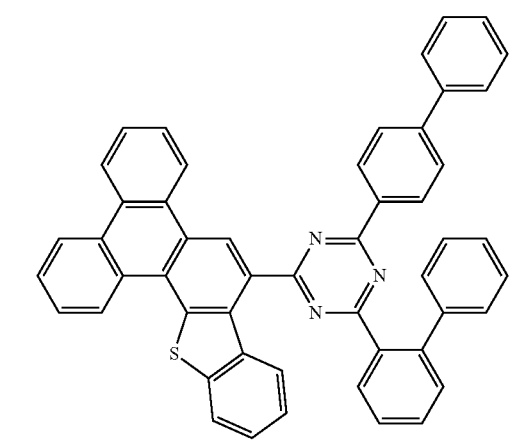

-continued
[A-51]
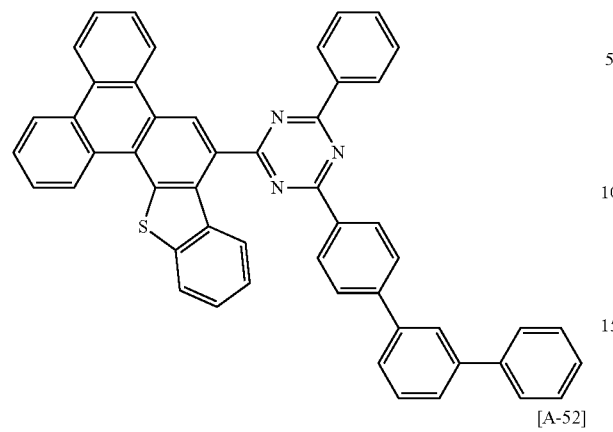
[A-52]
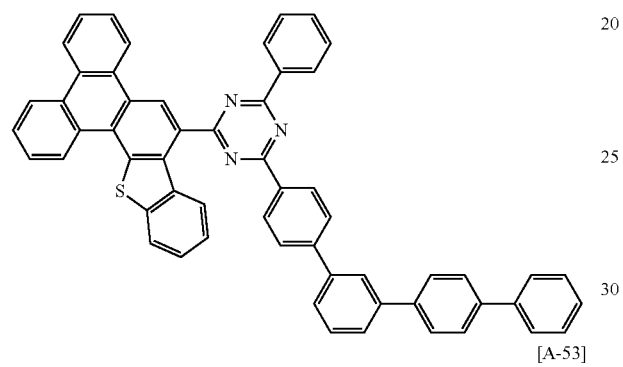
[A-53]
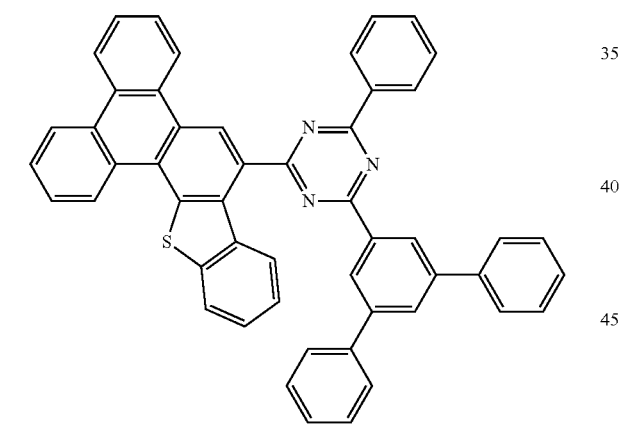
[A-54]
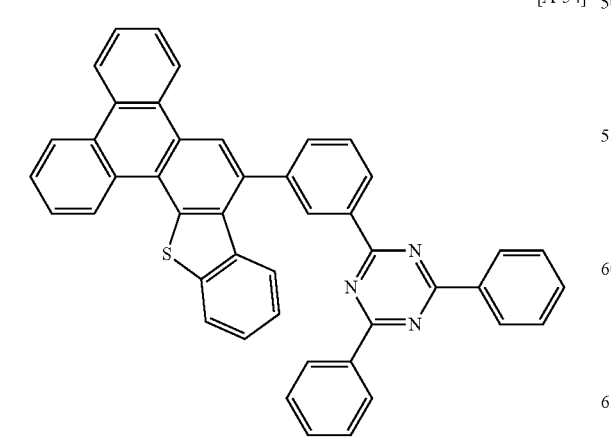
-continued
[A-55]
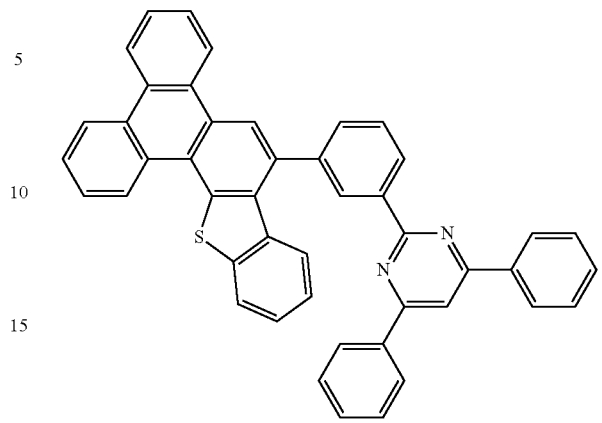
[A-56]
[A-57]
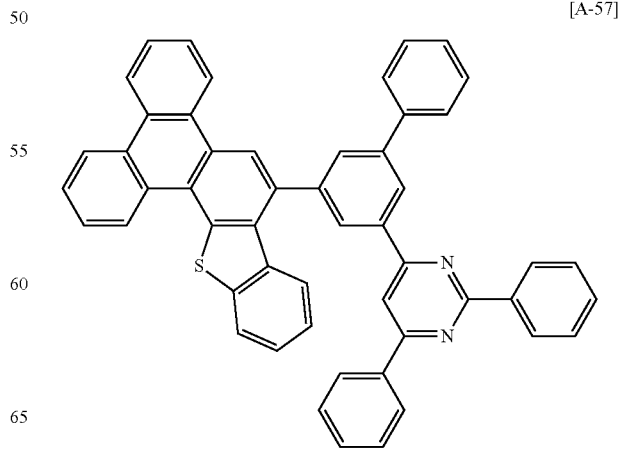

[A-58]
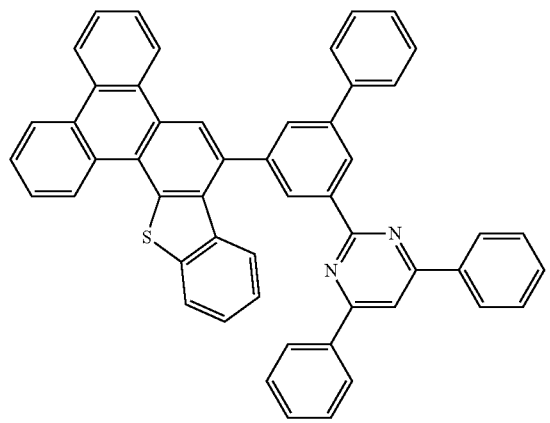
[A-61]
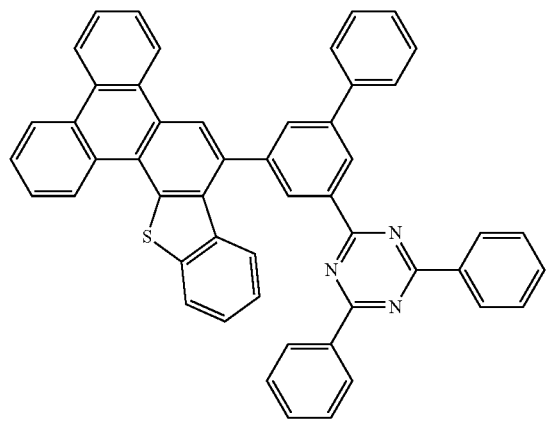
[A-62]
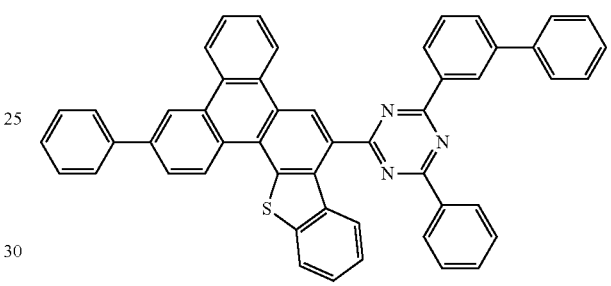
[A-59]
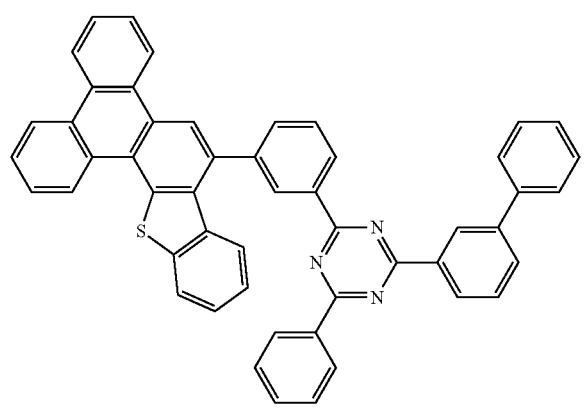
[A-63]
[A-60]
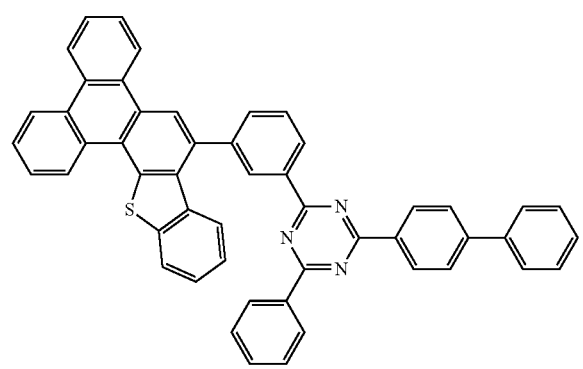
[A-64]
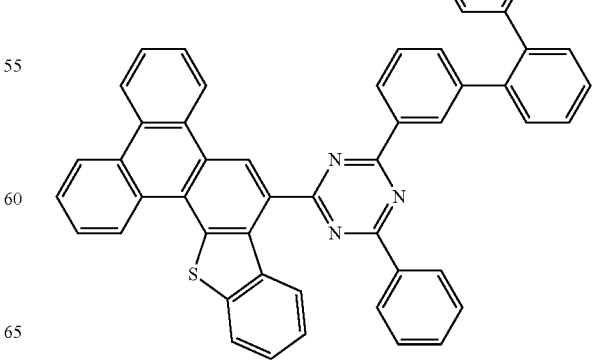

[A-65]
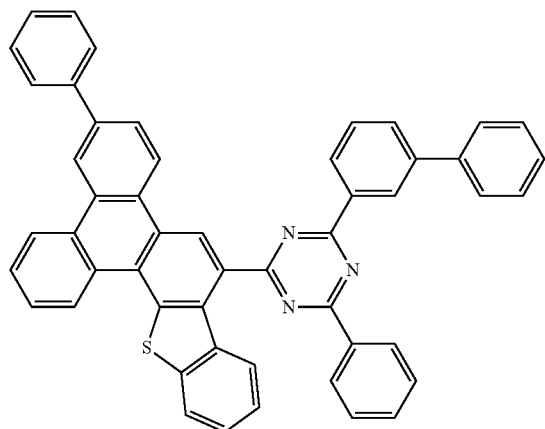
[A-69]
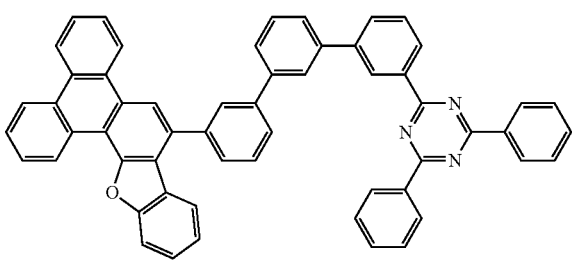
[A-66]
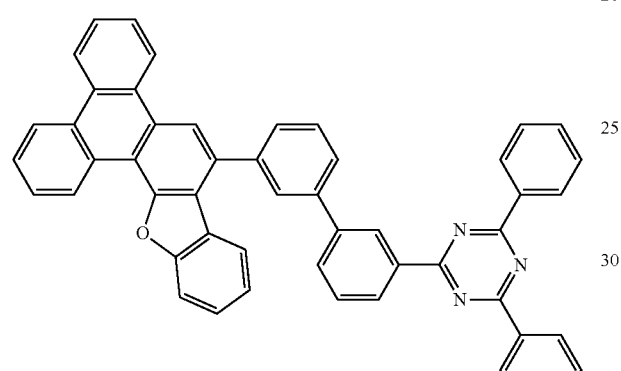
[A-70]
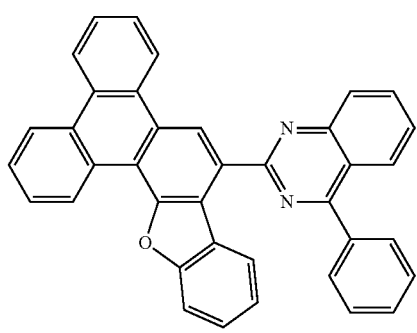
[A-67]
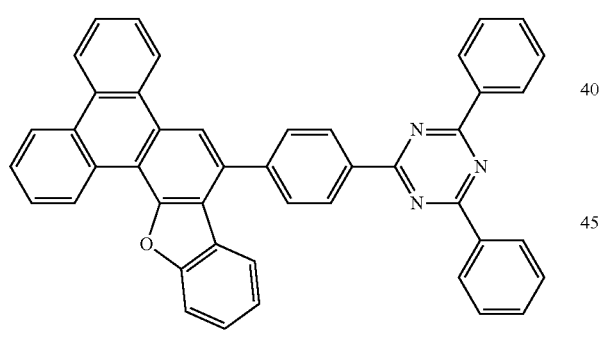
[A-71]
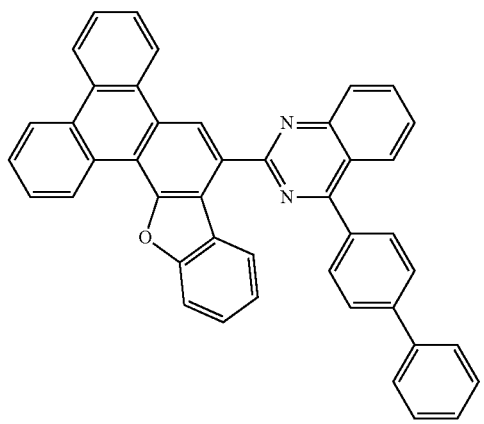
[A-68]
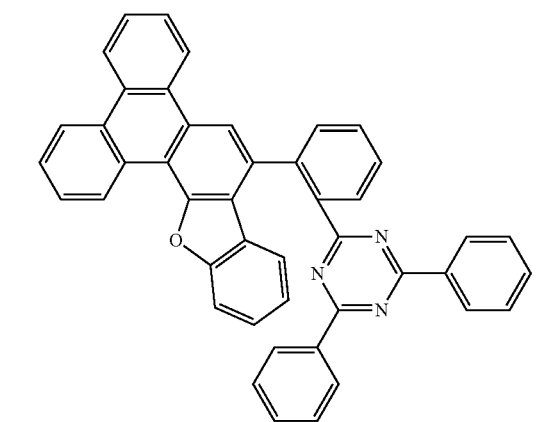
[A-72]
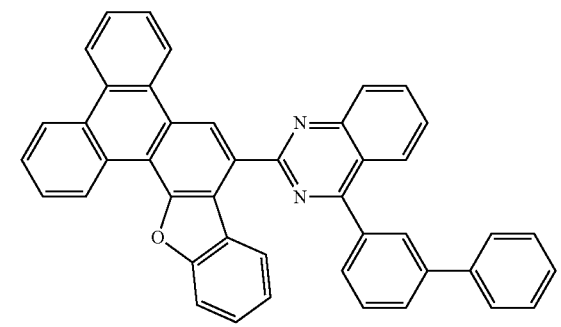

[A-73]
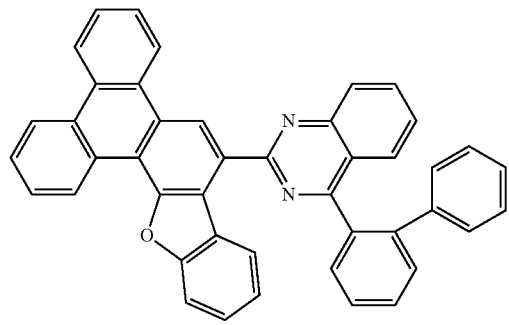
[A-74]
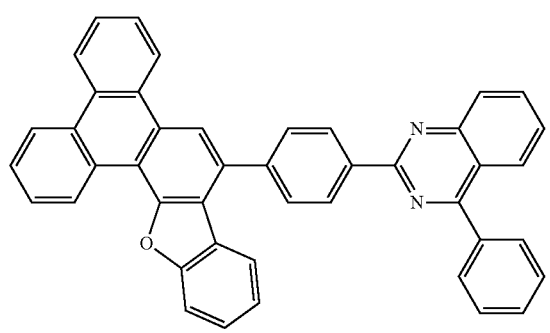
[A-75]
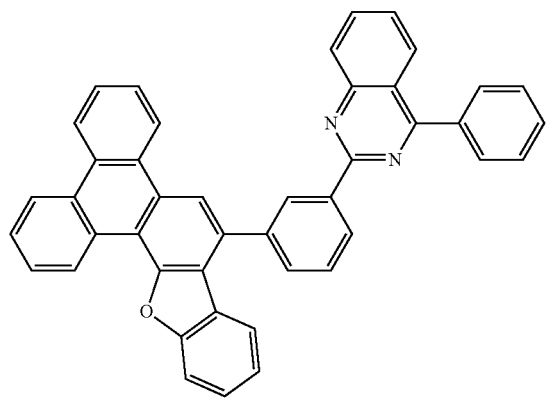
[A-76]
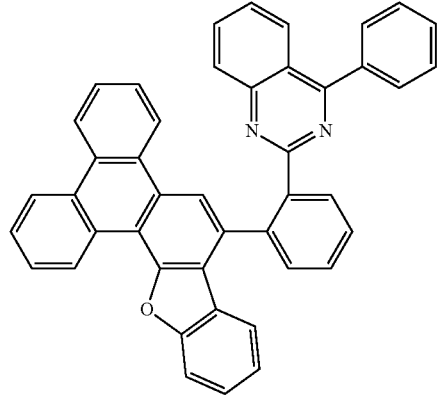
[A-77]
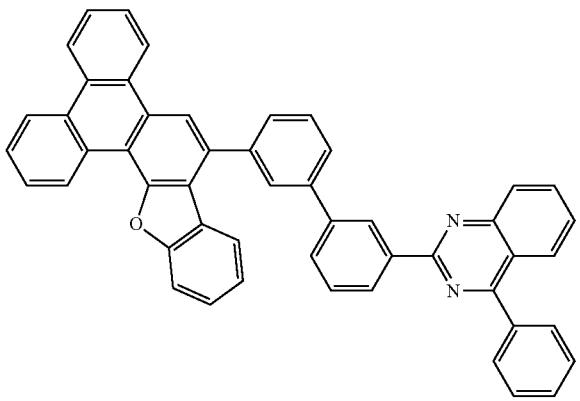
[A-78]
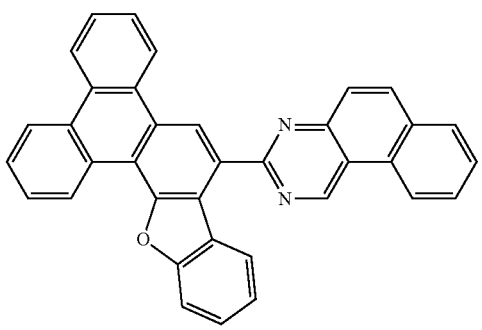
[A-79]
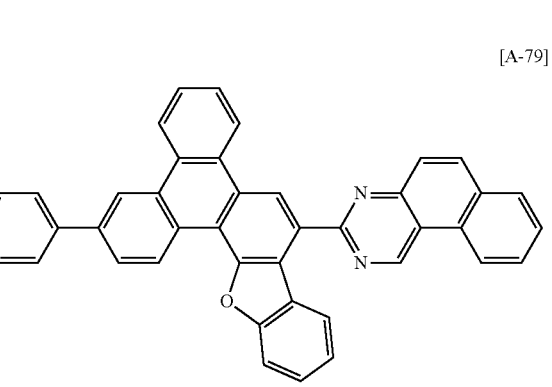
[A-80]
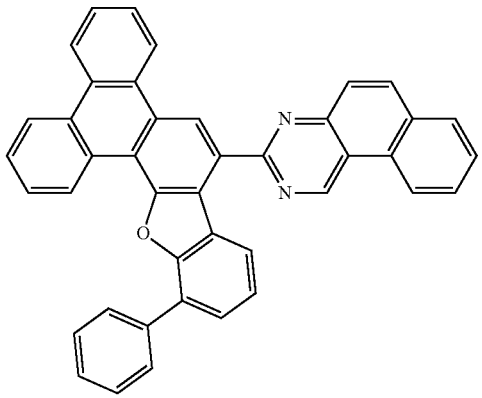

-continued
[A-81]
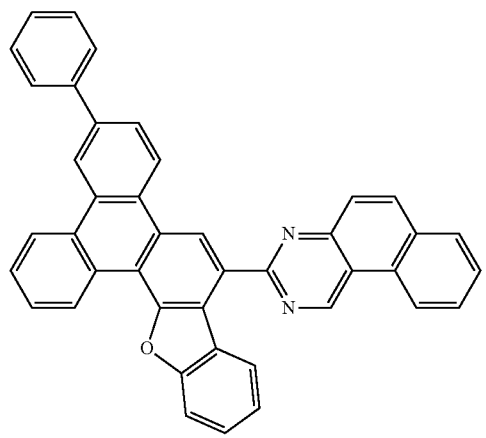
[A-82]
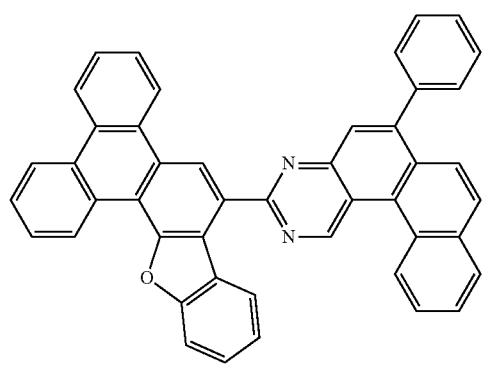
[A-83]
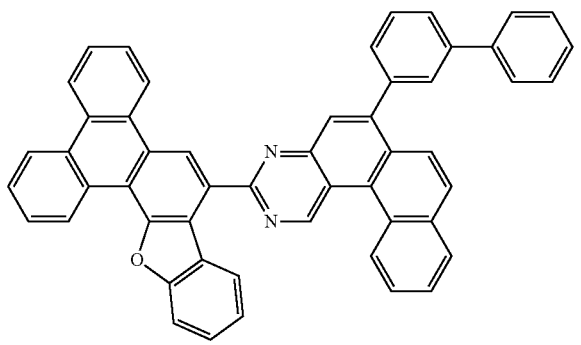
[A-84]
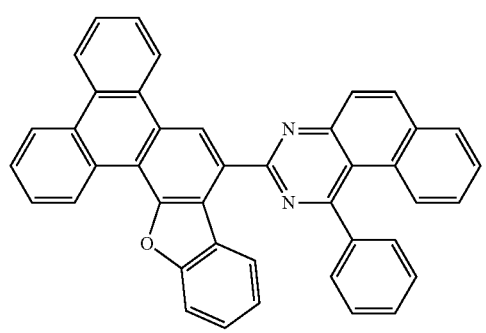
-continued
[A-85]
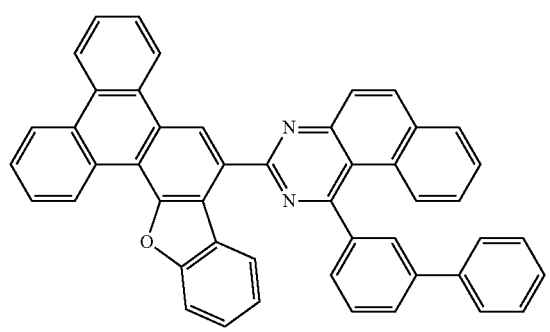
[A-86]
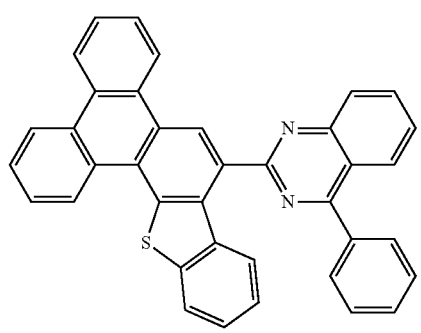
[A-87]
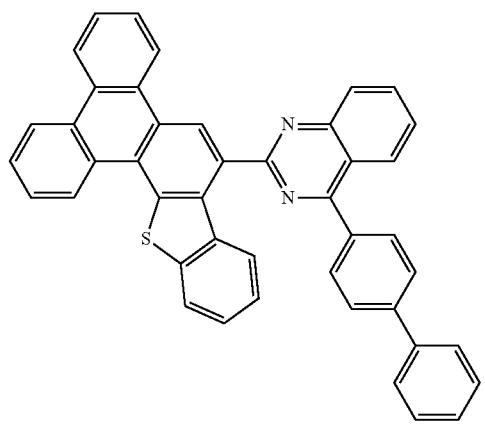
[A-88]
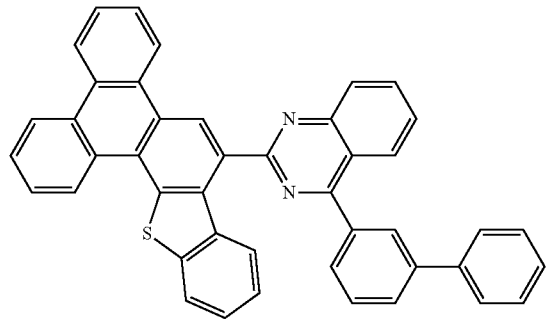

[A-89]
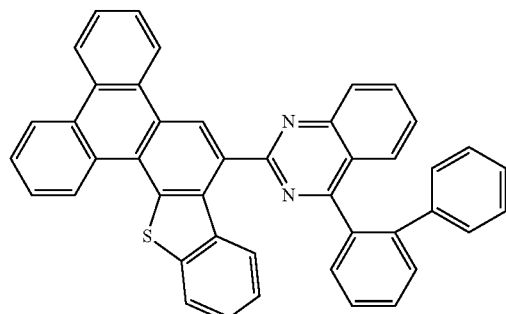
[A-90]
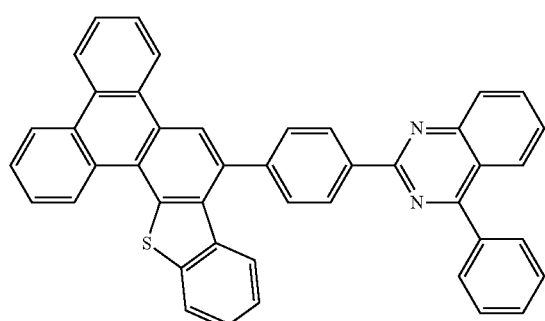
[A-91]
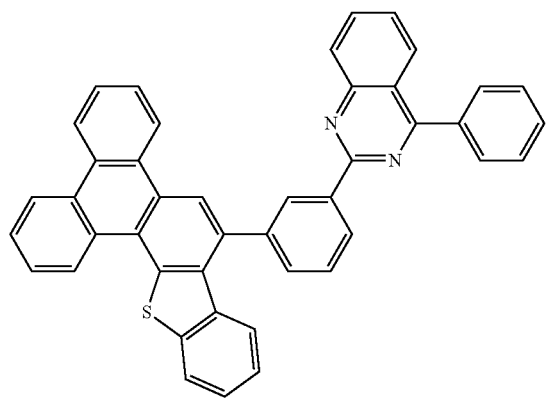
[A-92]
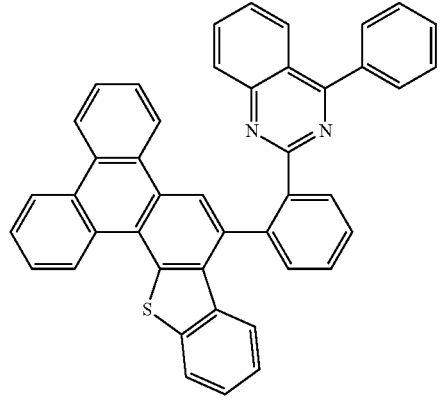
[A-93]
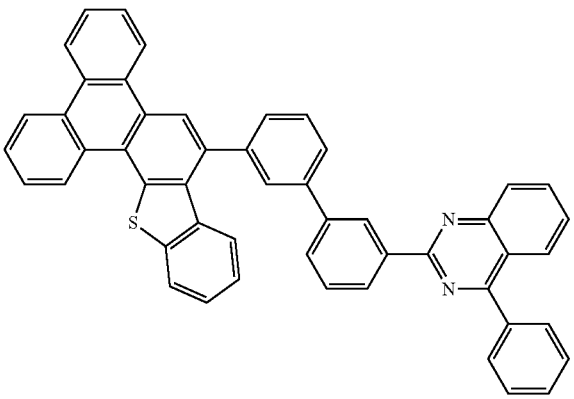
[A-94]
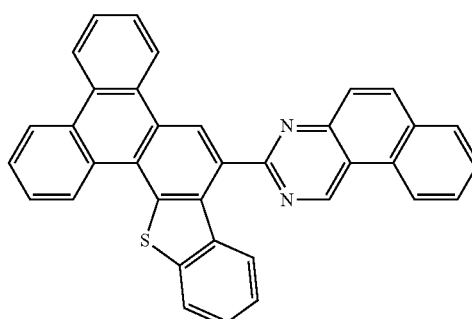
[A-95]
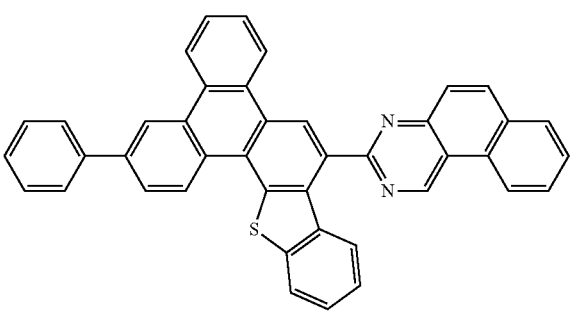
[A-96]
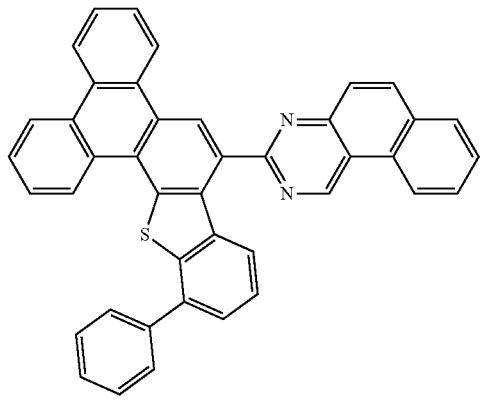

[A-97]
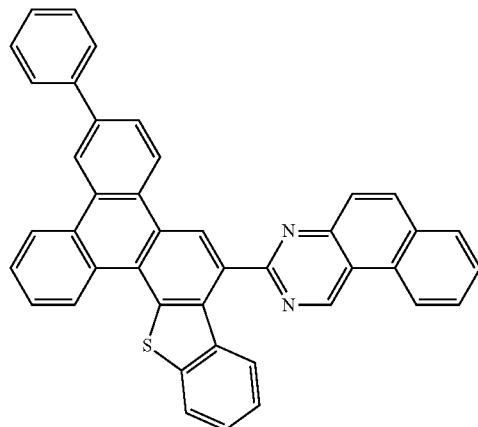
[A-101]
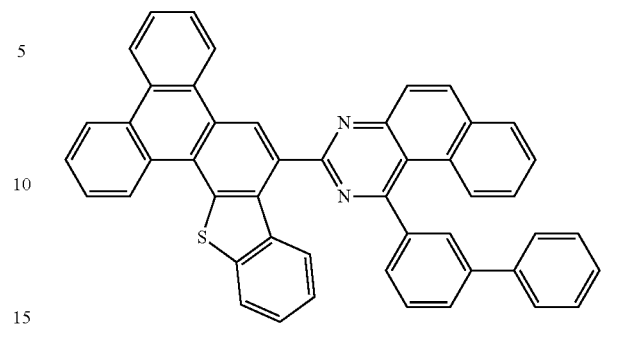
[A-98]
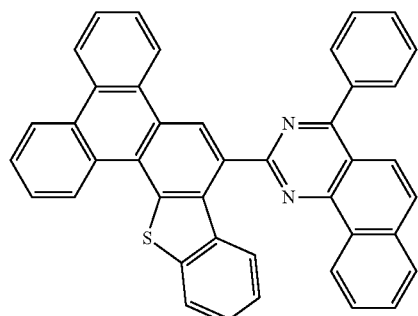
[A-102]
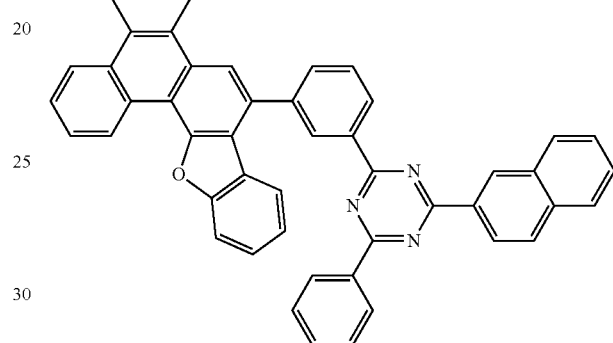
[A-99]
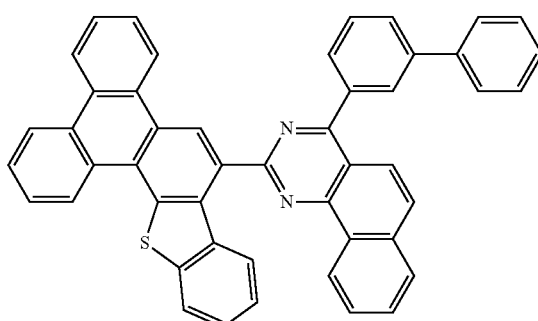
[A-103]
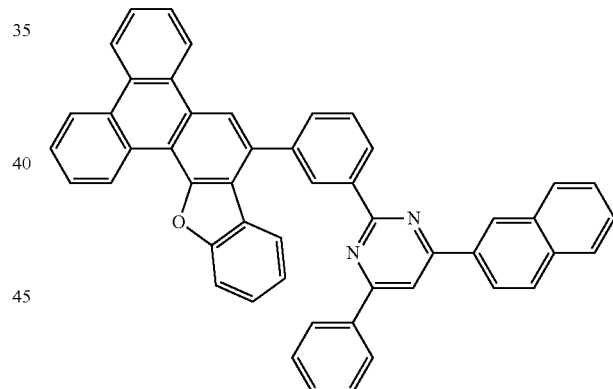
[A-100]
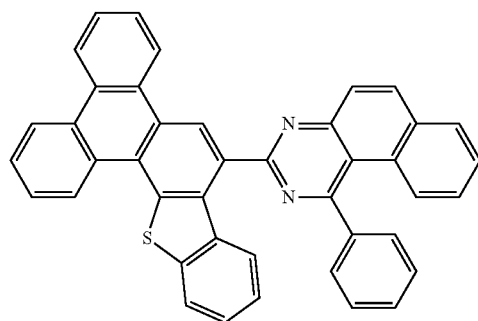
[A-104]
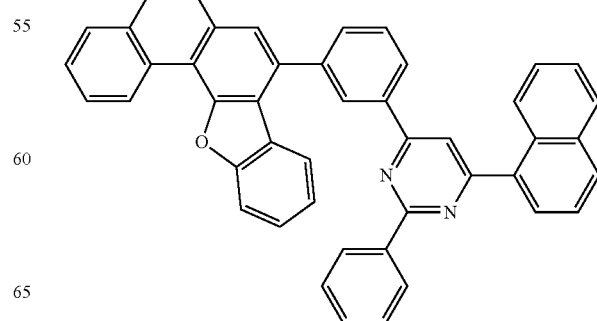

[A-105]
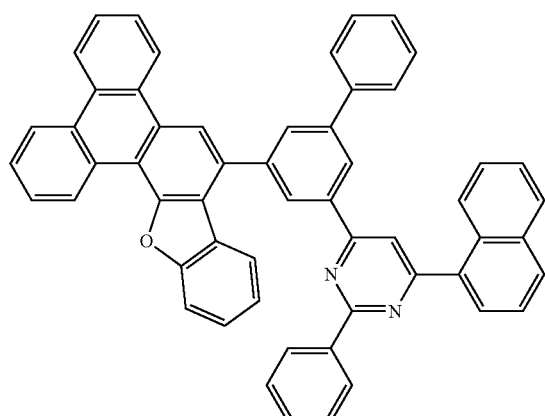
[A-106]
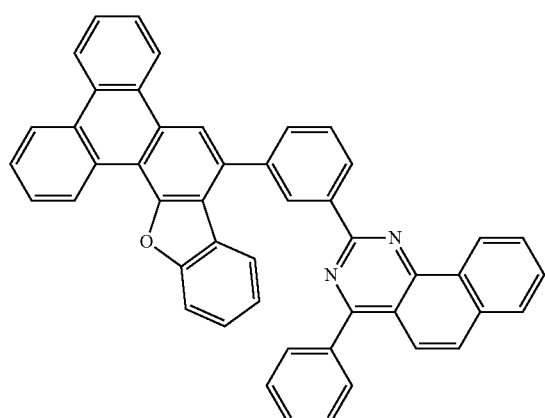
[A-107]
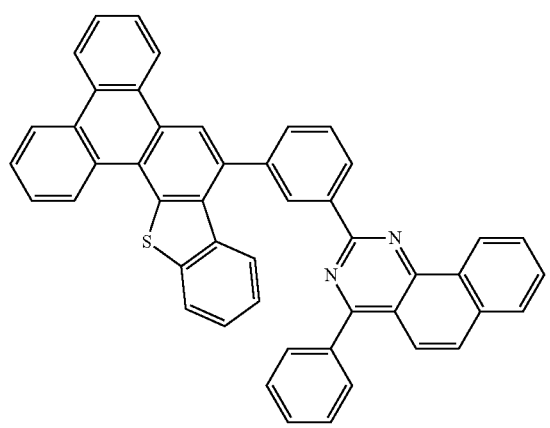
[B-1]
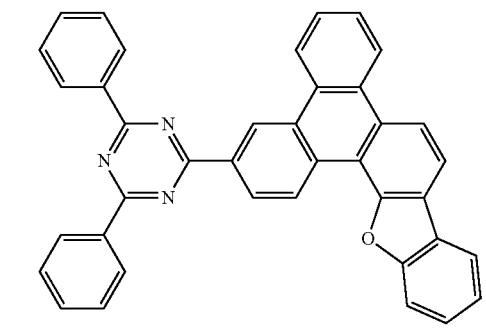
[B-2]
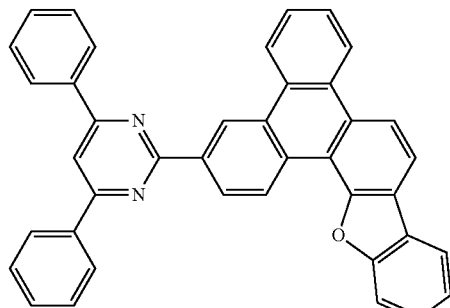
[B-3]
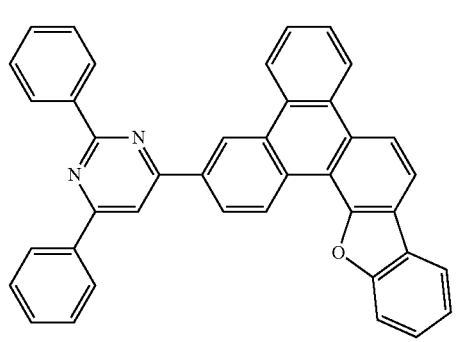
[B-4]
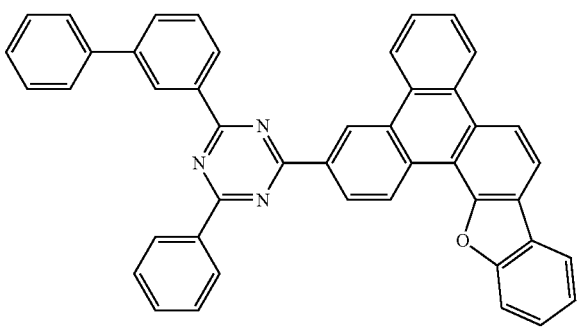
[B-5]
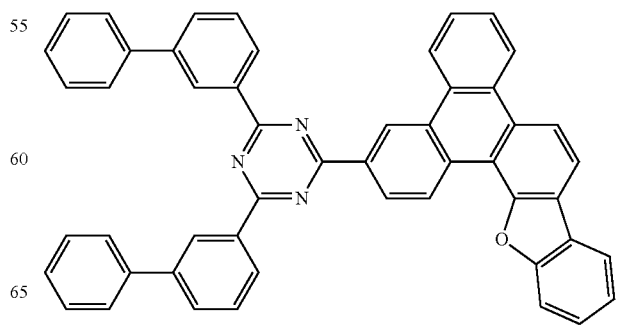

[B-6]
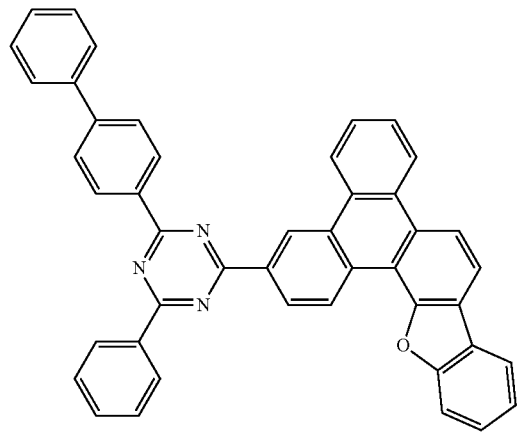
[B-7]
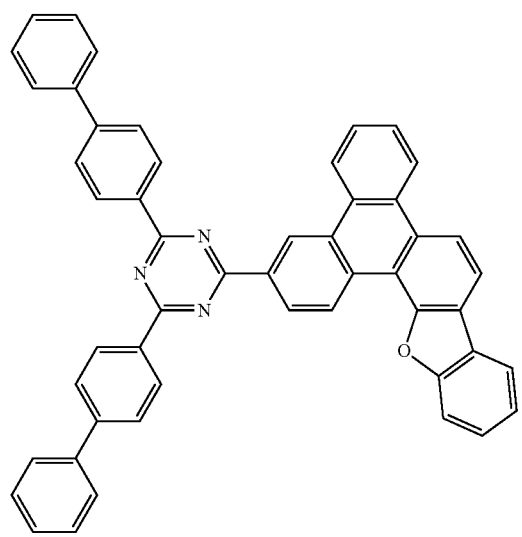
[B-8]
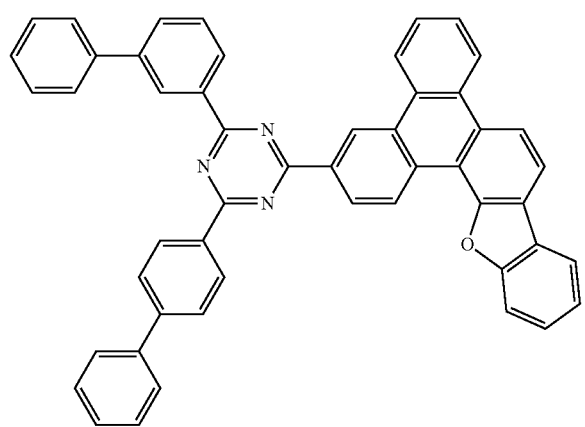
[B-9]
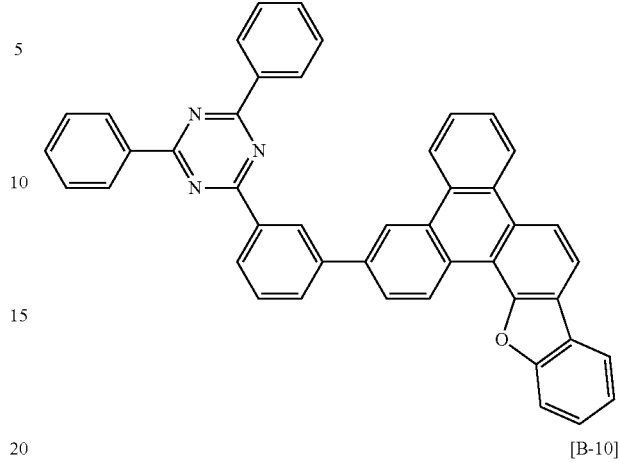
[B-10]
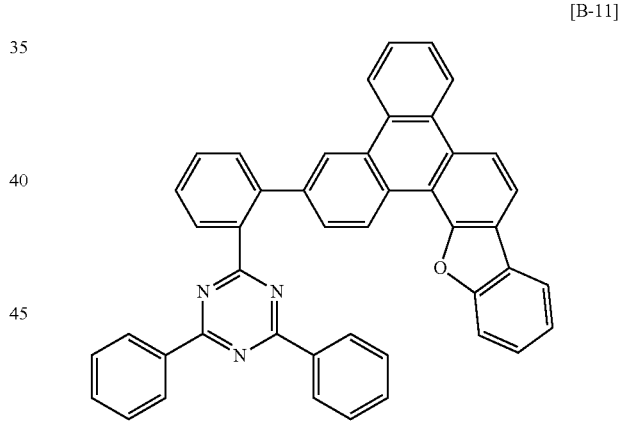
[B-11]
[B-12]
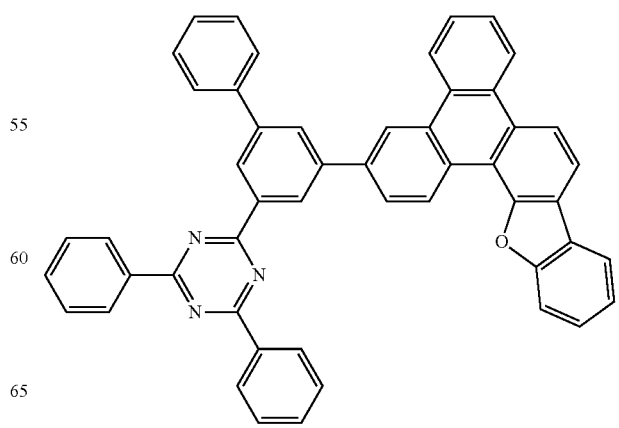

[B-13]

[B-14]

[B-15]

[B-16]

[B-17]

[B-18]

[B-19]

[B-20]
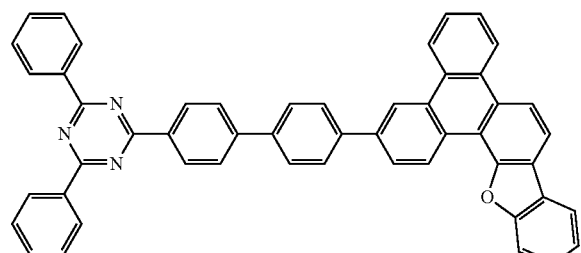
[B-21]
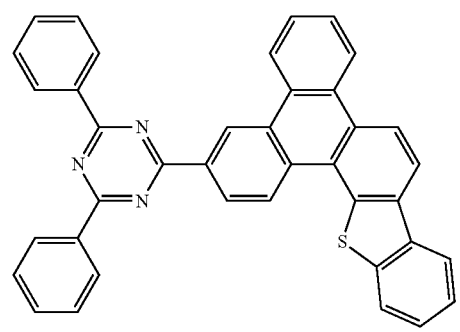
[B-22]
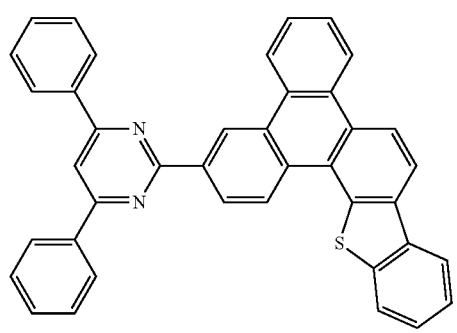
[B-23]
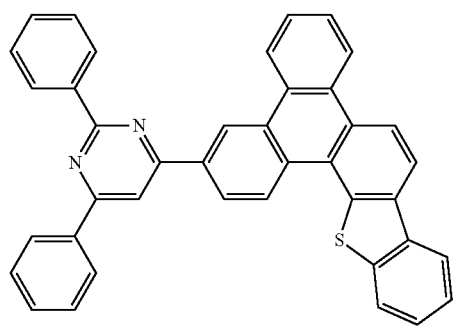
[B-24]
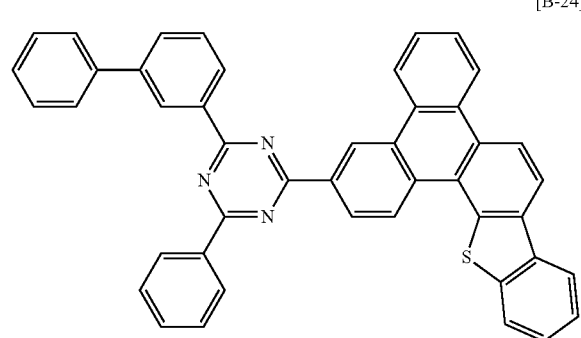
[B-25]
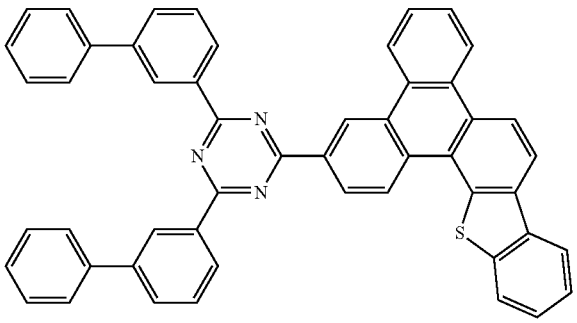
[B-26]
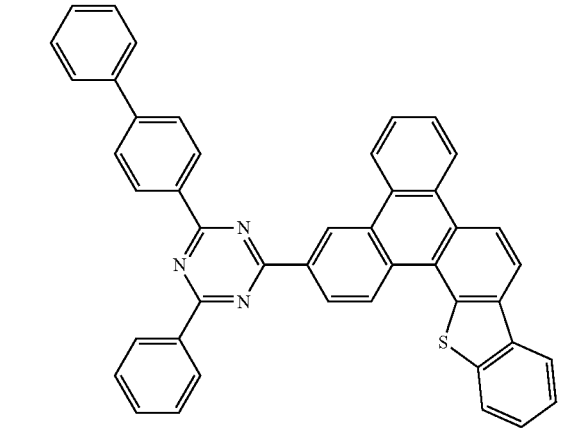
[B-27]
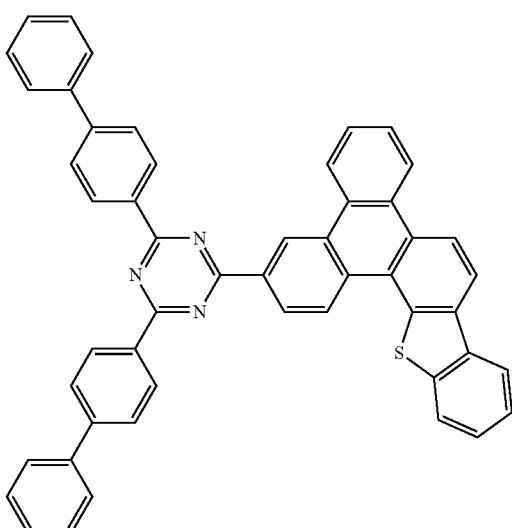

[B-28]
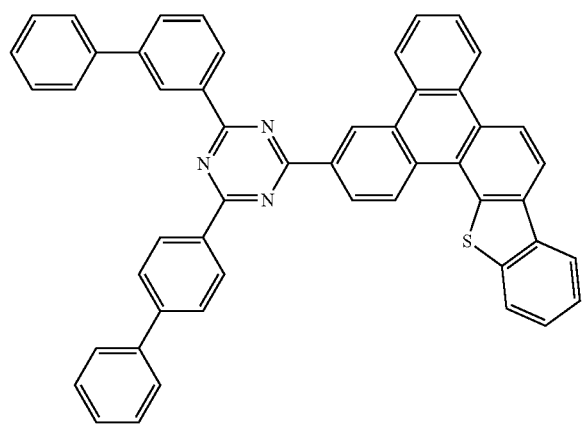
[B-29]
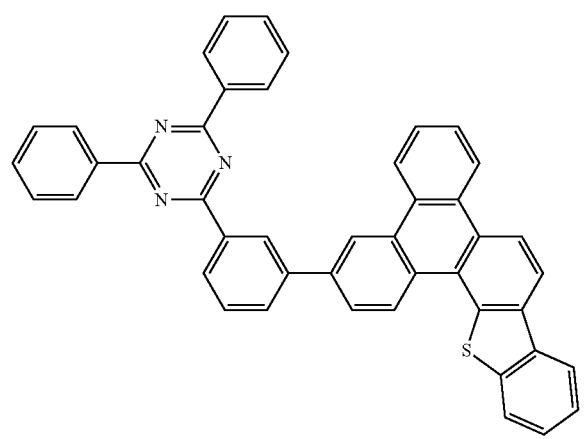
[B-30]
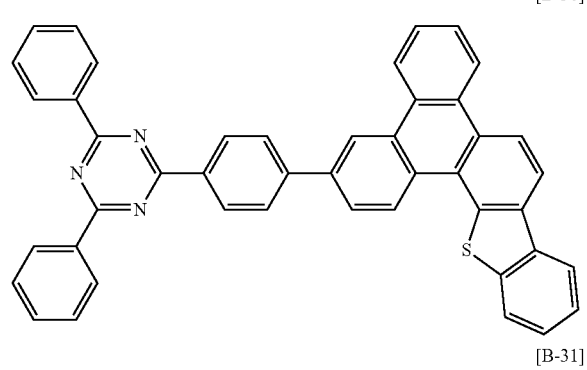
[B-31]
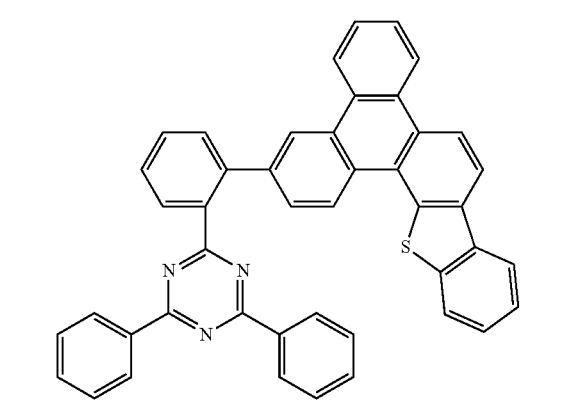
[B-32]
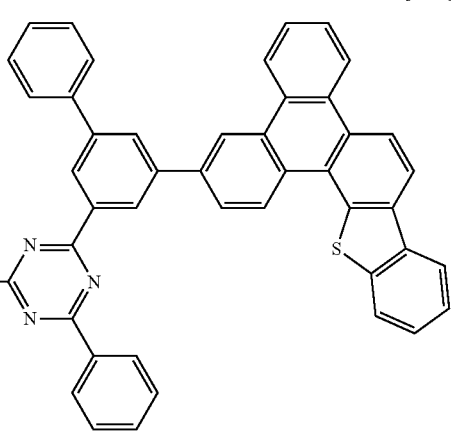
[B-33]
[B-34]

[B-35]
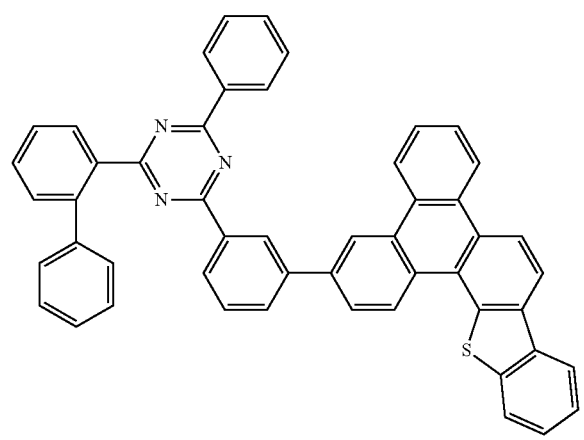
[B-36]
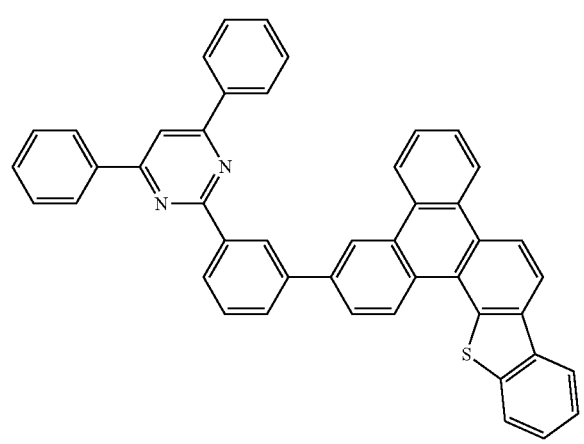
[B-37]
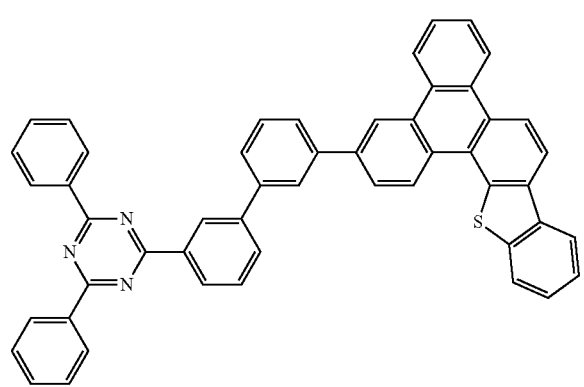
[B-38]
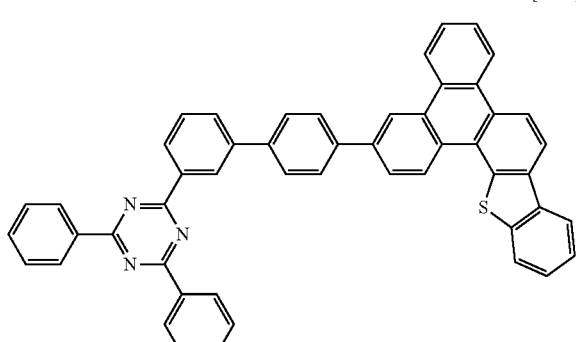
[B-39]
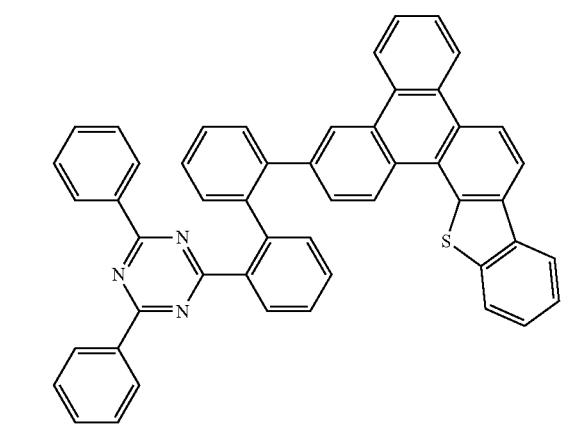
[B-40]
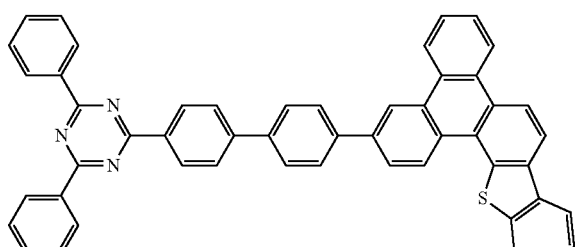
[B-41]
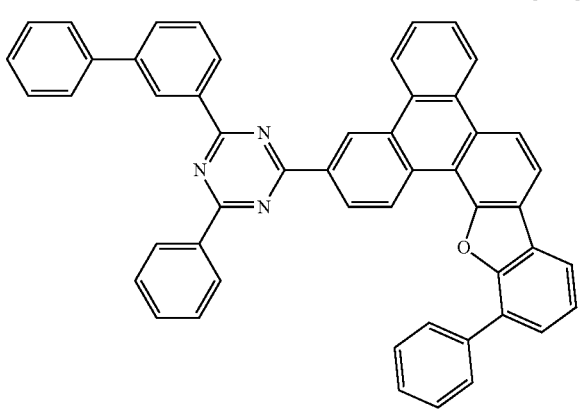

-continued
[B-42]
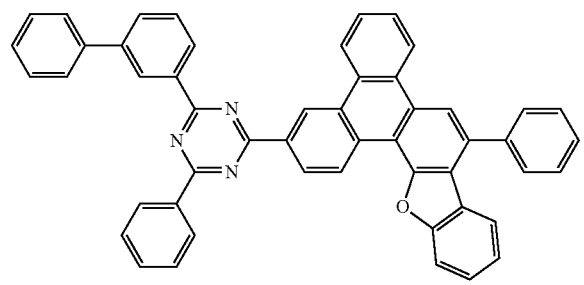
[B-43]
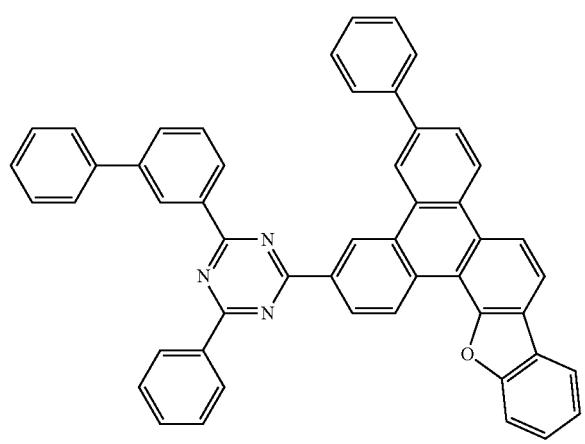
[B-44]
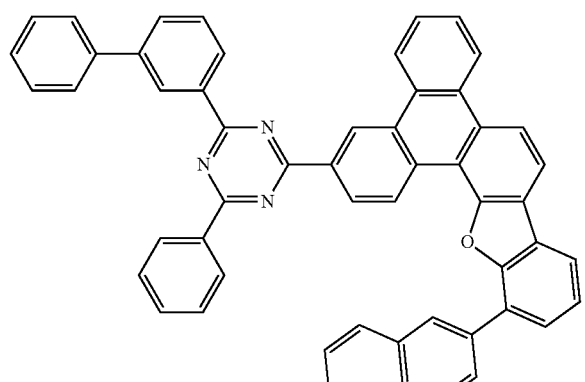
[B-45]
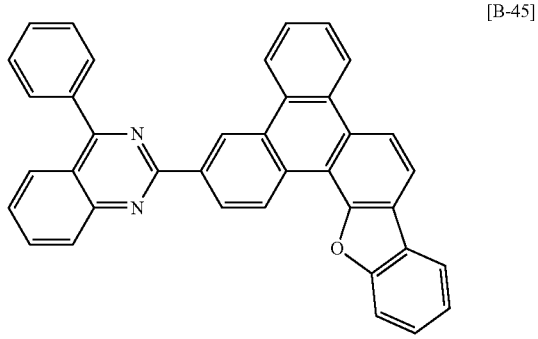
-continued
[B-46]
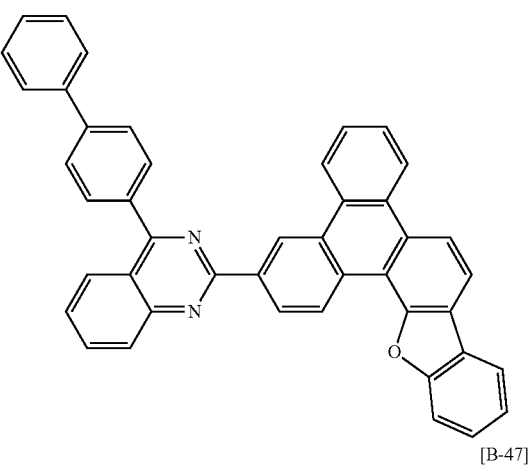
[B-47]
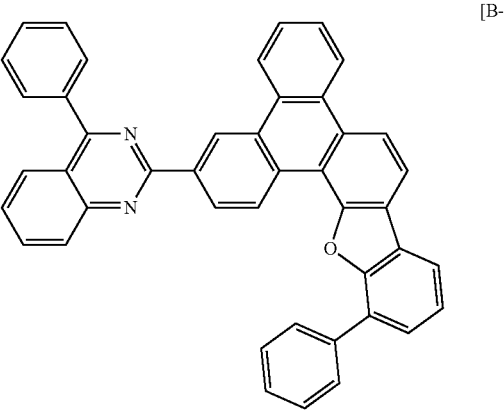
[B-48]
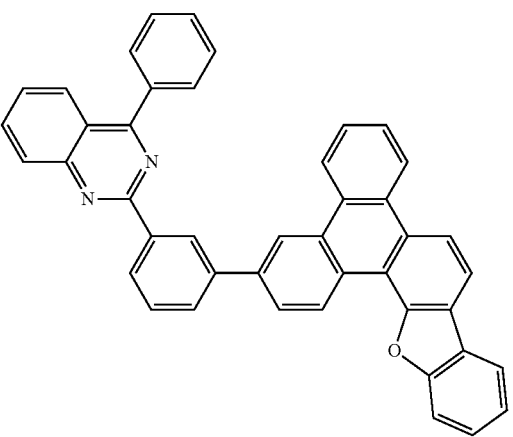
[B-49]

[B-50]
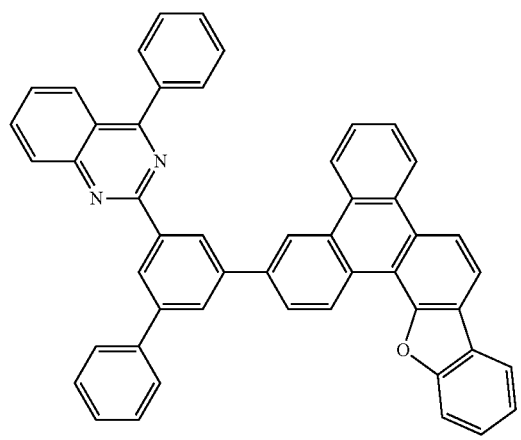
[B-51]
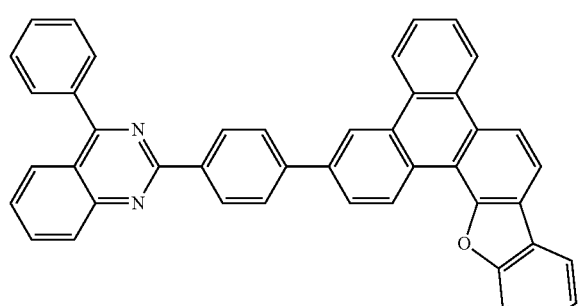
[B-52]
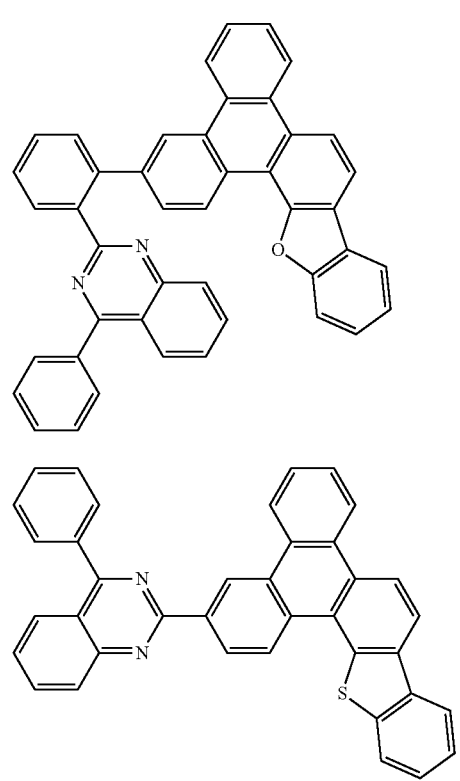
[B-53]
[B-54]
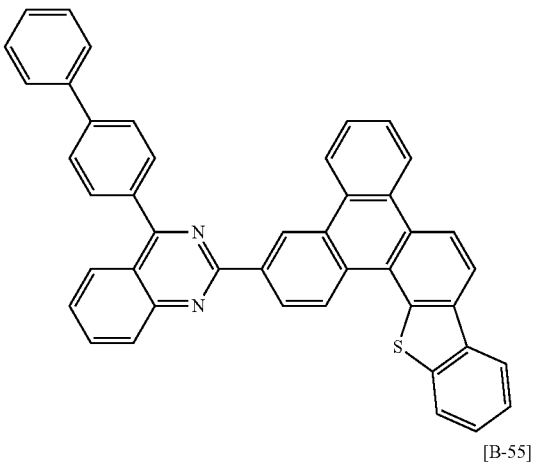
[B-55]
[B-56]
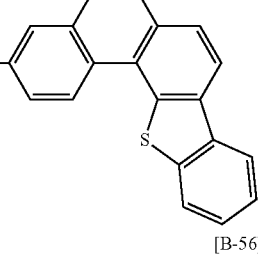
[B-57]
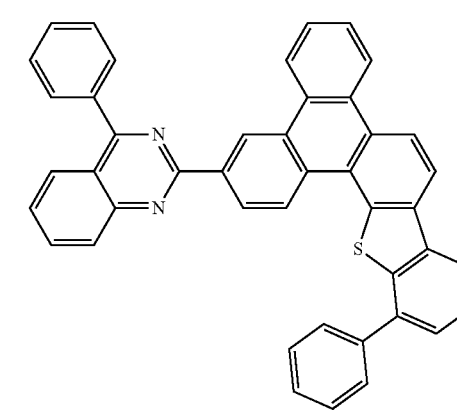

-continued

[B-58]
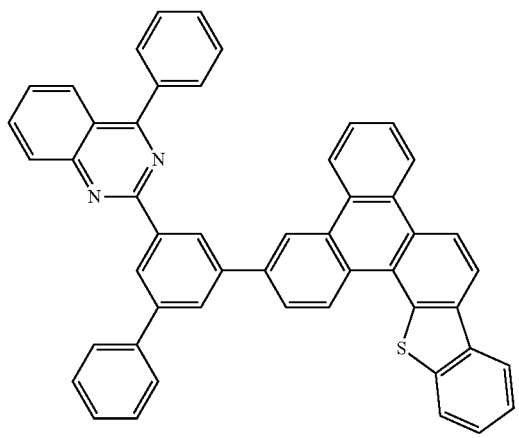

[B-59]
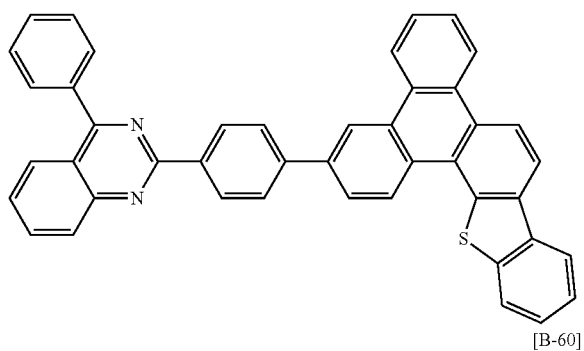

[B-60]
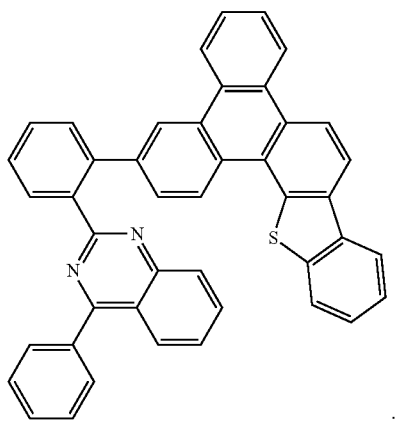

The first compound for an organic optoelectronic device may be applied to an organic optoelectronic device and may be applied to an organic optoelectronic device, alone or together with a compound for an organic optoelectronic device. When the compound for an organic optoelectronic device is used with the other compound for an organic optoelectronic device, they may be applied in a form of a composition.

The compound for an organic optoelectronic device may further include a dopant. The dopant may be a red, green, or blue dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more types thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$L_2MX$ [Chemical Formula Z]

In Chemical Formula Z, M is a metal, and $L_2$ and X are the same or different, and are a ligand to form a complex compound with M.

The M may be for example Ir, Pt, Os, Ti, Zr, Hf, Eu, Th, Tm, Fe, Co, Ni, Ru, Rh, Pd, or a combination thereof and the L and X may be for example a bidendate ligand.

Hereinafter, an organic optoelectronic device including the aforementioned compound for an organic optoelectronic device is described.

An organic optoelectronic device according to another embodiment includes an anode and a cathode facing each other and at least one organic layer disposed between the anode and the cathode, wherein the organic layer includes the aforementioned compound for an organic optoelectronic device.

For example, the organic layer may include a light emitting layer and the light emitting layer may include the compound for an organic optoelectronic device as a host, for example a green host of the light emitting layer.

In addition, the organic layer may include a light emitting layer and at least one auxiliary layer selected from a hole injection layer, a hole transport layer, an electron blocking layer, an electron transport layer, an electron injection layer, and a hole blocking layer and the auxiliary layer may include the compound for an organic optoelectronic device.

The auxiliary layer may further include an electron transport auxiliary layer that is adjacent to the light emitting layer and the electron transport auxiliary layer may include the compound for an organic optoelectronic device.

The organic optoelectronic device may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectronic device is described referring to drawings.

FIGS. 1 and 2 are cross-sectional views of an organic light emitting diode according to embodiments.

Referring to FIG. 1, an organic light emitting diode 100 according to an embodiment includes an anode 120 and a cathode 110 facing each other and an organic layer 105 interposed between the anode 120 and cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like: a combination of a metal and an oxide such as ZnO and Al or $SnO_2$ and Sb, a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a small work function to help electron injection, and may be for example a metal, a metal oxide, and/or a conductive polymer. The cathode 110 may be for example a metal such as magnesium, calcium, sodium, potassium, titanium, indium, yttrium, lithium, gadolinium, aluminum silver, tin, lead, cesium, barium, and the like or an alloy thereof; a multi-layer structure material such as LiF/Al, LiO₂/Al, LiF/Ca, LiF/Al, and BaF₂/Ca, but is not limited thereto.

The organic layer 105 includes a light emitting layer 130 including the aforementioned compound for an organic optoelectronic device.

FIG. 2 is a cross-sectional view showing an organic light emitting diode according to another embodiment.

Referring to FIG. 2, an organic light emitting diode 200 further includes a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound for an organic optoelectronic device of the present invention may be included in the organic layer. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode (OLED) display.

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there are no particular descriptions or were synthesized by known methods.

(Preparation of Compound for Organic Optoelectronic Device)

The compound as one specific examples of the present invention was synthesized through the following steps.

(First Compound for Organic Optoelectronic Device)

Synthesis Example 1: Synthesis of Intermediate I-1

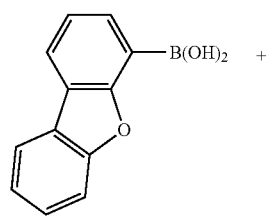

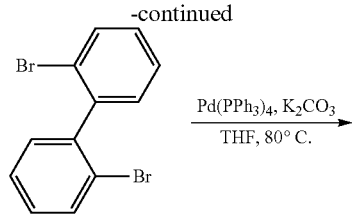

-continued

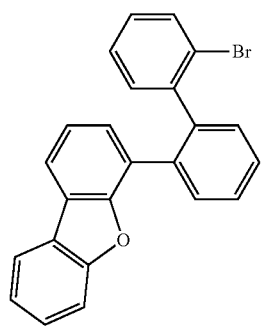

I-1

Dibenzofuran-4-boronic acid (50 g, 236 mmol) purchased from Tokyo Chemical Industry Co., Ltd. (http://www.tci-chemicals.com/) was dissolved in 0.8 L of tetrahydrofuran (THF) under a nitrogen environment, 2,2'-dibromobiphenyl (110 g, 354 mmol) purchased from Mascot (Asia) Co. Ltd. and tetrakis(triphenylphosphine)palladium (2.72 g, 2.86 mmol) were added thereto, and the obtained mixture was stirred. Potassium carbonate saturated in water (81.5 g, 59.0 mmol) was added thereto, and the obtained mixture was heated and refluxed at 80° C. for 12 hours. When a reaction was complete, water was added to the reaction solution, and the resultant was extracted with dichloromethane (DCM) and treated with anhydrous MgSO₄ to remove moisture, filtered, and concentrated under a reduced pressure. The obtained residue was separated and purified through flash column chromatography to obtain Intermediate I-1 (49.7 g, 53%).

HRMS (70 eV, EI+): m/z calcd for C24H15BrO: 398.0306, found: 398.

Elemental Analysis: C, 72%; H, 4%

Synthesis Example 2: Synthesis of Intermediate I-2

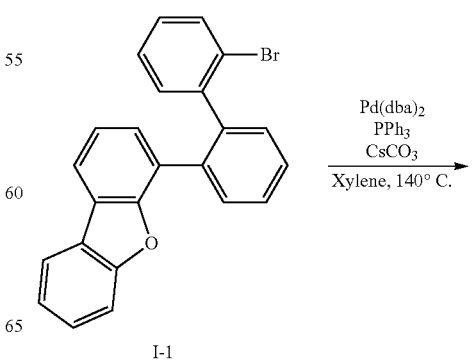

I-1

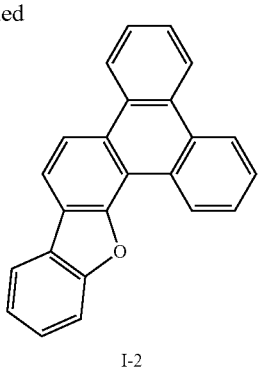

I-2

Intermediate I-1 (50 g, 236 mmol) was dissolved in 0.5 L of xylene under a nitrogen environment, bis(dibenzylideneacetone)palladium (0) (3.48 g, 6.05 mmol), triphenylphosphine (6.35 g, 2.42 mmol), and cesium carbonate (47.3 g, 145 mmol) were added thereto, and the obtained mixture was heated and refluxed at 40° C. for 27 hours. When a reaction was complete, water was added to the reaction solution, and the resultant was treated with dichloromethane (DCM) to remove anhydrous $MgSO_4$ to remove moisture, filtered, and concentrated under a reduced pressure. The obtained residue was separated and purified through flash column chromatography to obtain Intermediate I-2 (27.6 g, 72%).

HRMS (70 eV, EI+): m/z calcd for $C_{24}H_{14}O$: 318.1045, found: 318.

Elemental Analysis: C, 91%; H, 4%

Synthesis Example 3: Synthesis of Intermediate I-3

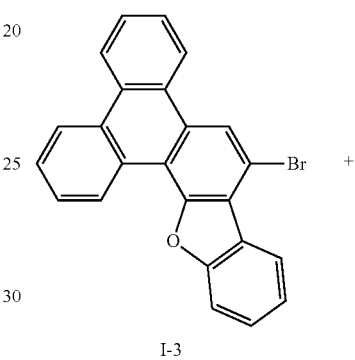

Intermediate I-2 (27 g, 84.8 mmol) was dissolved in 0.1 L of chloroform under a nitrogen environment, and bromine (3.01 g, 18.9 mmol) was added thereto and reacted therewith. When a reaction was complete, sodium thiosulfate saturated in water (6.62 g, 41.9 mmol) was added to the reaction solution, and the resultant was extracted dichloromethane (DCM), treated with anhydrous $MgSO_4$ to remove moisture, and then, filtered and concentrated under a reduced pressure. The obtained residue was separated and purified through flash column chromatography to obtain Intermediate I-3 (21.2 g, 63%).

HRMS (70 eV, EI+): m/z calcd for $C_{24}H_{13}BrO$: 396.0150, found: 396.

Elemental Analysis: C, 73%; H, 3%

Synthesis Example 4: Synthesis of Intermediate I-4

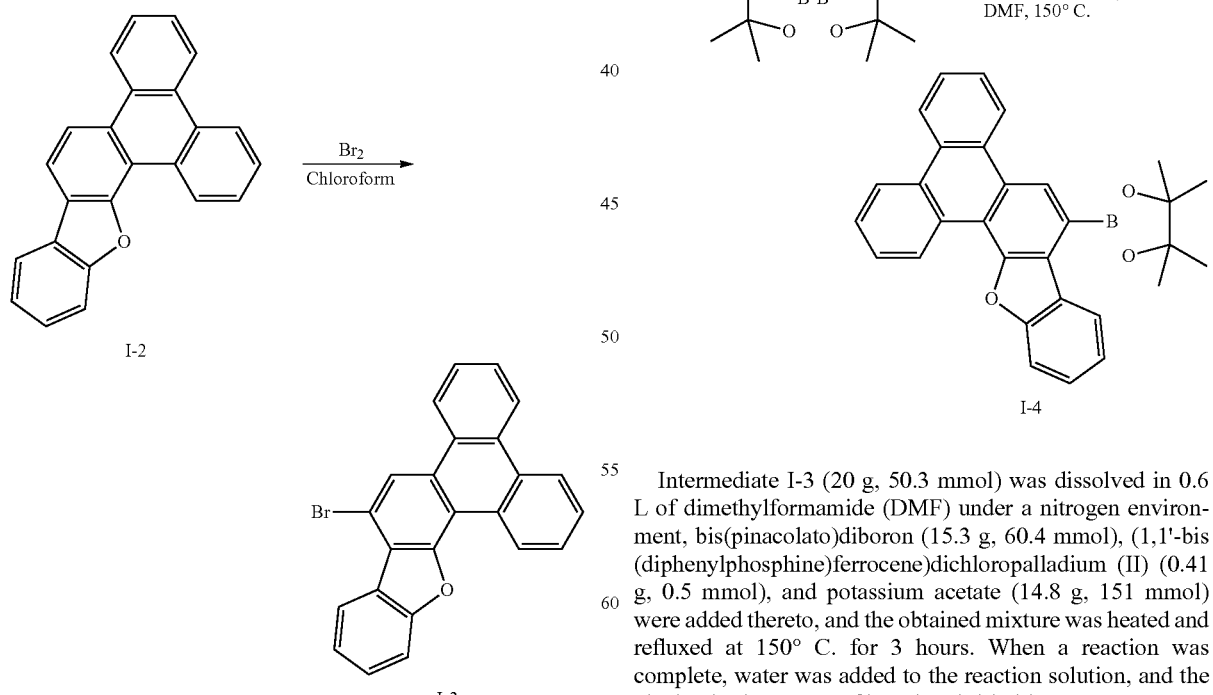

Intermediate I-3 (20 g, 50.3 mmol) was dissolved in 0.6 L of dimethylformamide (DMF) under a nitrogen environment, bis(pinacolato)diboron (15.3 g, 60.4 mmol), (1,1'-bis(diphenylphosphine)ferrocene)dichloropalladium (II) (0.41 g, 0.5 mmol), and potassium acetate (14.8 g, 151 mmol) were added thereto, and the obtained mixture was heated and refluxed at 150° C. for 3 hours. When a reaction was complete, water was added to the reaction solution, and the obtained mixture was filtered and dried in a vacuum oven. The obtained residue was separated and purified through flash column chromatography to obtain Intermediate 1-4 (19.9 g, 89%).

HRMS (70 eV, EI+): m/z calcd for C30H25BO3: 444.1897, found: 444.

Elemental Analysis: C, 81%; H, 6%

Synthesis Example 5: Synthesis of Intermediate I-5

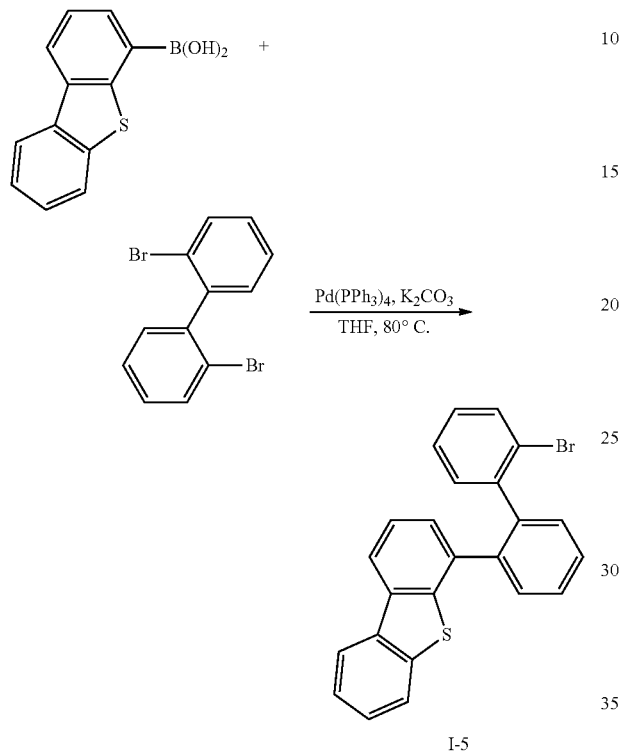

I-5

Intermediate I-5 (54.6 g, 60%) was obtained according to the same method as Synthesis Example 1 by using dibenzothiophene-4-boronic acid (50 g, 219 mmol) purchased from Tokyo Chemical Industry Co., Ltd. (http://www.tci-chemicals.com/) and 2,2'-dibromobiphenyl (102 g, 329 mmol) purchased from Mascot (Asia) Company Limited.

HRMS (70 eV, EI+): m/z calcd for C24H15BrS: 414.0078, found: 414.

Elemental Analysis: C, 69%; H, 4%

Synthesis Example 6: Synthesis of Intermediate I-6

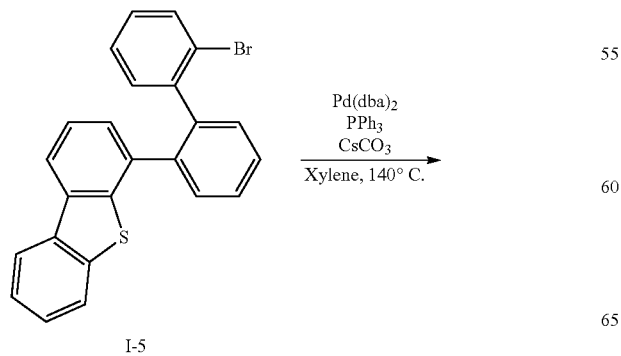

I-5

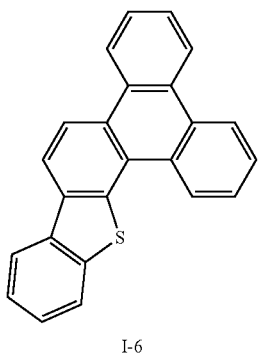

I-6

Intermediate I-6 (34.2 g, 85%) was obtained according to the same method as Synthesis Example 2 by using Intermediate I-5 (50 g, 120 mmol).

HRMS (70 eV, EI+): m/z calcd for C24H14S: 334.0816, found: 334.

Elemental Analysis: C, 86%; H, 4%

Synthesis Example 7: Synthesis of Intermediate I-7

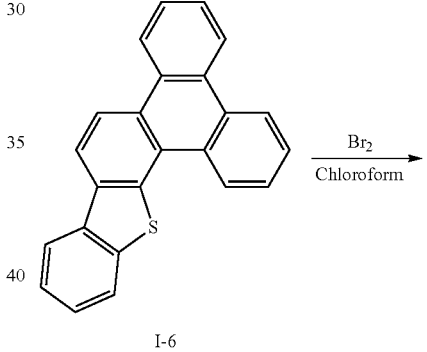

I-6

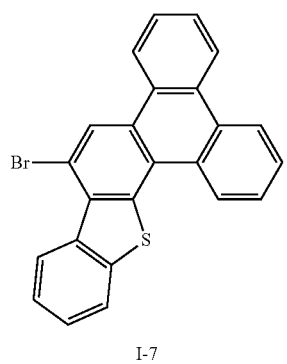

I-7

Intermediate I-7 (28.5 g, 72%) was obtained according to the same method as Synthesis Example 3 by using Intermediate I-6 (32 g, 95.7 mmol).

HRMS (70 eV, EI+): m/z calcd for C24H13BrS: 411.9921, found: 412.
Elemental Analysis: C, 70%; H, 3%

Synthesis Example 8: Synthesis of Intermediate I-8

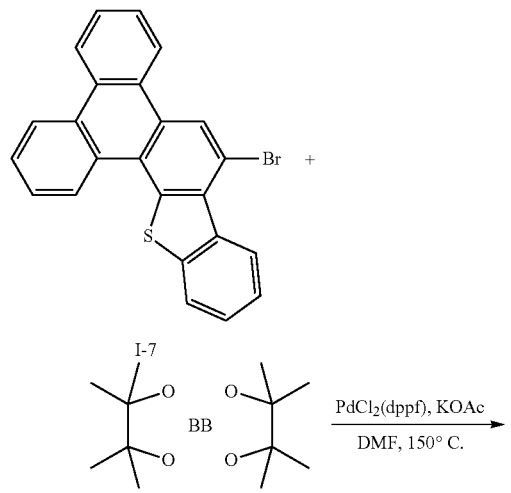

Intermediate I-8 (29.6 g, 95%) was obtained according to the same method as Synthesis Example 3 by using Intermediate I-7 (28 g, 67.7 mmol).

HRMS (70 eV, EI+): m/z calcd for C30H25BO2S: 460.1668, found: 460.
Elemental Analysis: C, 78%; H, 5%

Synthesis Example 9: Synthesis of Intermediate I-9

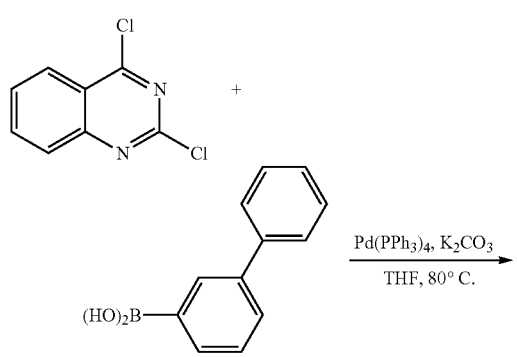

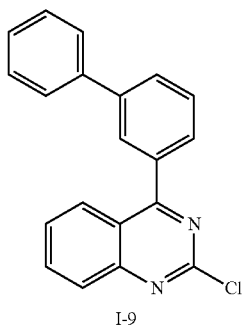

Intermediate I-9 (77.3 g, 54%) was obtained according to the same method as Synthesis Example 1 by using 2,4-dichloroquinazoline (100 g, 502 mmol) purchased from P&H Tech Co., Ltd. (http://www.phtech.co.kr/) and biphenyl-3-boronic acid (89.5 g, 452 mmol).

HRMS (70 eV, EI+): m/z calcd for C20H13ClN2: 316.0767, found: 316.
Elemental Analysis: C, 76%; H, 4%

Synthesis Example 10: Synthesis of Intermediate I-10

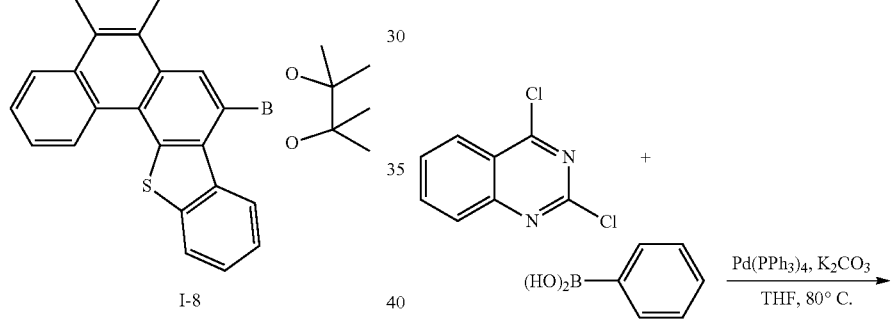

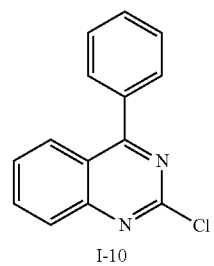

Intermediate I-10 (65.3 g, 60%) was obtained according to the same method as Synthesis Example 1 by using 2,4-dichloroquinazoline (100 g, 502 mmol) purchased from P&H Tech Co., Ltd. (http://www.phtech.co.kr/) and phenylboronic acid (55.1 g, 452 mmol).

HRMS (70 eV, EI+): m/z calcd for C14H9ClN2: 240.0454, found: 240.
Elemental Analysis: C, 70%; H, 4%

Synthesis Example 11: Synthesis of Intermediate I-11

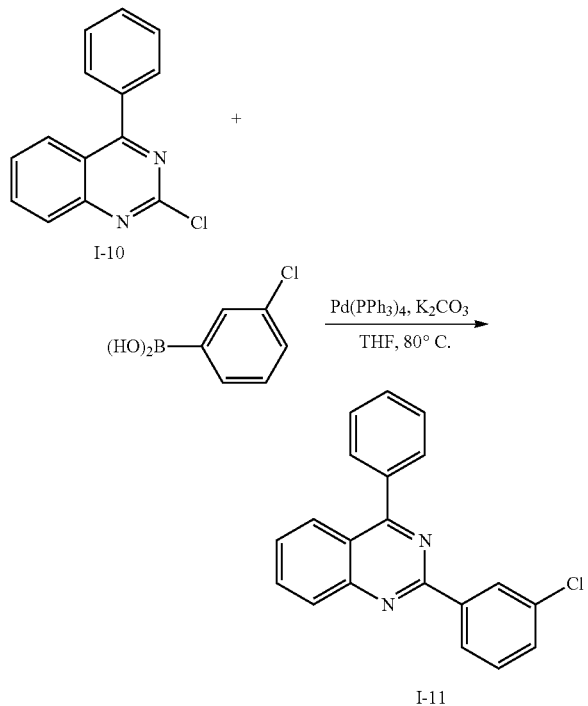

Intermediate I-11 (74.9 g, 95%) was obtained according to the same method as Synthesis Example 1 by using Intermediate I-10 (60 g, 249 mmol) and 3-chlorophenylboronic acid (42.8 g, 274 mmol).
HRMS (70 eV, EI+): m/z calcd for C20H13ClN2: 316.0767, found: 316.
Elemental Analysis: C, 76%; H, 4%

Synthesis Example 12: Synthesis of Intermediate I-12

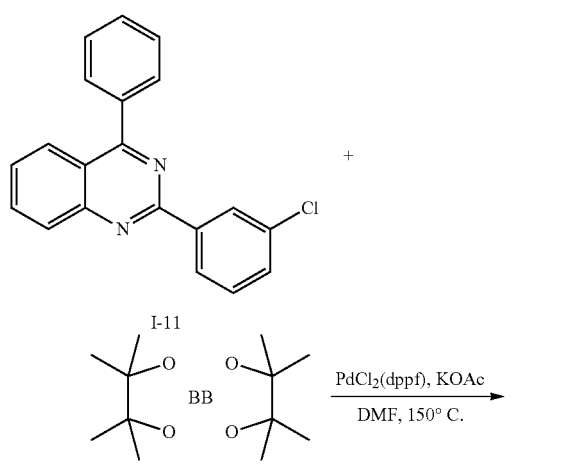

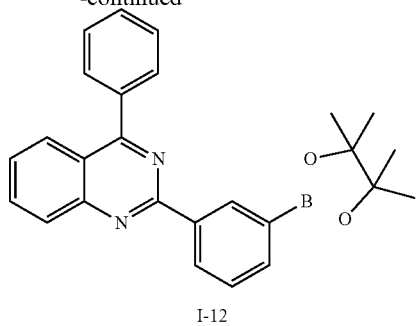

Intermediate I-12 (60.5 g, 67%) was obtained according to the same method as Synthesis Example 1 by using Intermediate I-11 (70 g, 221 mmol).
HRMS (70 eV, EI+): m/z calcd for C26H25BN2O2: 408.2009, found: 408.
Elemental Analysis: C, 76%; H, 6%

Synthesis Example 13: Synthesis of Intermediate I-13

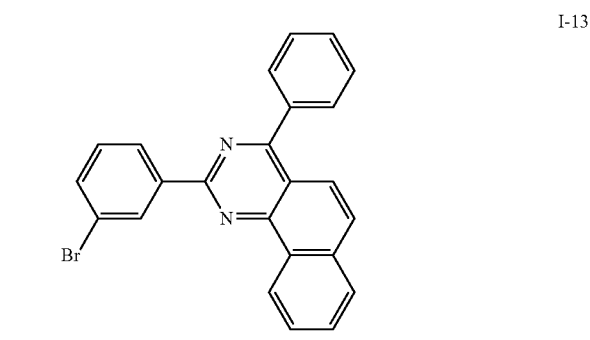 [SMILES: Brc1cccc(-c2nc(-c3ccccc3)c3ccc4ccccc4c3n2)c1]

Intermediate I-13 was synthesized by referring to a synthesis method of Korean Laid-open publication KR10-2015-0140127.
HRMS (70 eV, EI+): m/z calcd for C24H15BrN2: 410.0419, found: 410.
Elemental Analysis: C, 70%; H, 4%

Synthesis Example 14: Synthesis of Intermediate I-14

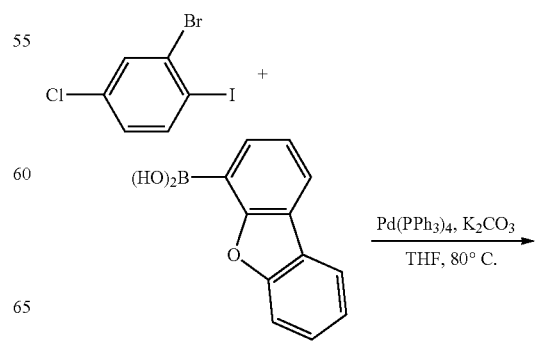

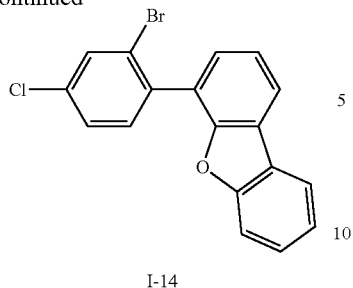

I-14

Intermediate I-14 (22.8 g, 40%) was obtained according to the same method as Synthesis Example 1 by using 2-bromo-4-chloro-1-iodobenzene (50 g, 158 mmol) purchased from Sigma Aldrich Co., Ltd. (http://www.sigmaaldrich.com/) and dibenzofuran-4-boronic acid (40.1 g, 189 mmol).

HRMS (70 eV, EI+): m/z calcd for C18H10BrClO: 355.9604, found: 356.

Elemental Analysis: C, 60%; H, 3%

Synthesis Example 15: Synthesis of Intermediate I-15

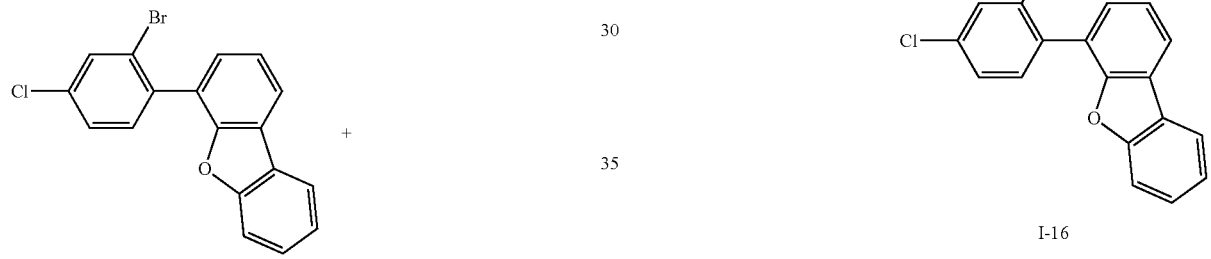

Intermediate I-15 (6.7 g, 26%) was obtained according to the same method as Synthesis Example 4 by using Intermediate I-14 (22.8 g, 63.8 mmol).

HRMS (70 eV, EI+): m/z calcd for C24H22BClO3: 404.1351, found: 404.

Elemental Analysis: C, 71%; H, 5%

Synthesis Example 16: Synthesis of Intermediate I-16

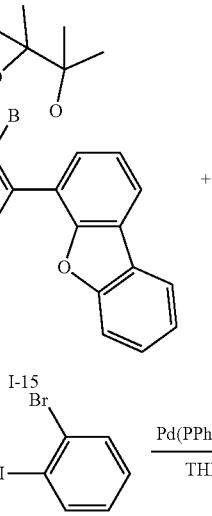

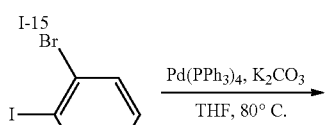

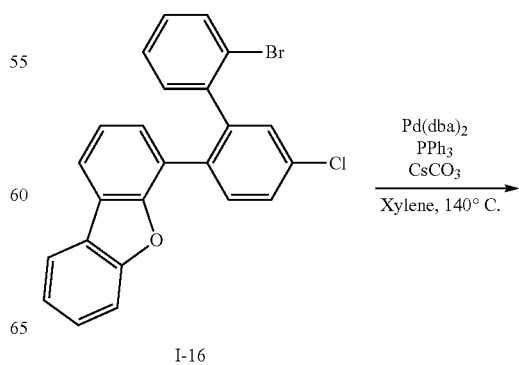

I-16

Intermediate I-16 (7.06 g, 98%) was obtained according to the same method as Synthesis Example 1 by using intermediate 1-15 (6.7 g, 16.6 mmol) and 1-bromo-2-iodobenzene (5.62 g, 19.9 mmol).

HRMS (70 eV, EI+): m/z calcd for C24H14BrClO: 431.9917, found: 432.

Elemental Analysis: C, 66%; H, 3%

Synthesis Example 17: Synthesis of Intermediate I-17

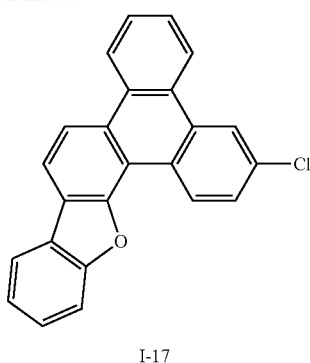

I-17

Intermediate I-17 (4.73 g, 83%) was obtained according to the same method as Synthesis Example 2 by using Intermediate I-16 (7 g, 16.1 mmol).

HRMS (70 eV, EI+): m/z calcd for C24H13C10: 352.0655, found: 352.

Elemental Analysis: C, 82%; H, 4%

Synthesis Example 18: Synthesis of Intermediate I-18

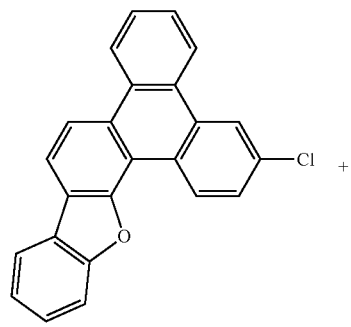

I-17

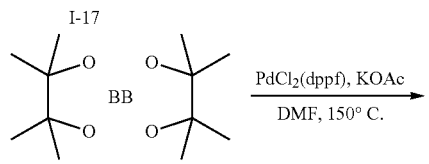

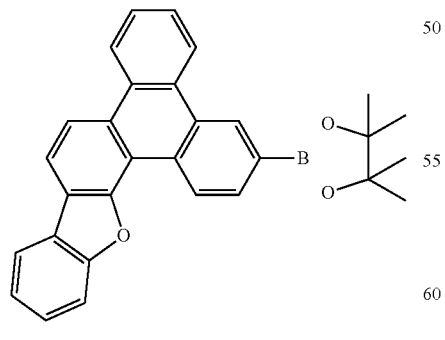

I-18

Intermediate I-18 (3.91 g, 69%) was obtained according to the same method as Synthesis Example 4 by using Intermediate I-17 (4.5 g, 12.8 mmol).

HRMS (70 eV. EI+): m/z calcd for C30H25BO3: 444.1897, found: 444.

Elemental Analysis: C, 81%; H, 6%

Synthesis Example 19: Synthesis of Intermediate I-19

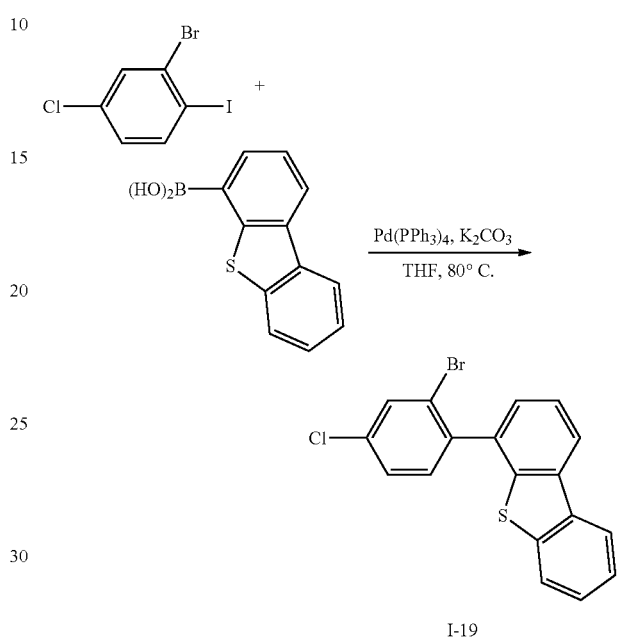

I-19

Intermediate I-19 (30.1 g, 51%) was obtained according to the same method as Synthesis Example 1 by using 2-bromo-4-chloro-1-iodobenzene (50 g, 158 mmol) purchased from Sigma Aldrich Co., Ltd. (http://www.sigmaaldrich.com/) and dibenzothiophene-4-boronic acid (43.1 g, 189 mmol).

HRMS (70 eV, EI+): m/z calcd for C18H10BrClS: 371.9375, found: 372.

Elemental Analysis: C, 58%; H, 3%

Synthesis Example 20: Synthesis of Intermediate I-20

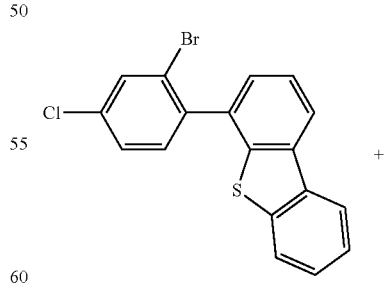

I-19

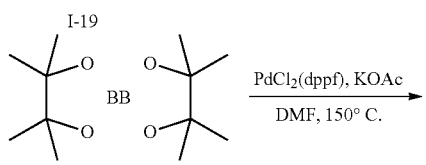

-continued

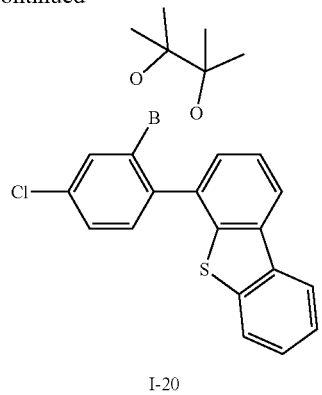

I-20

Intermediate I-20 (12.1 g, 37%) was obtained according to the same method as Synthesis Example 4 by using Intermediate I-19 (29 g, 77.6 mmol).

HRMS (70 eV, EI+): m/z calcd for $C_{24}H_{22}BClO_2S$: 420.1122, found: 420.

Elemental Analysis: C, 71%; H, 5%

Synthesis Example 21: Synthesis of Intermediate I-21

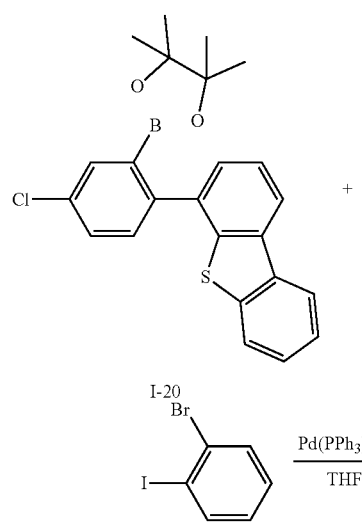

I-21

Intermediate I-21 (11.7 g, 95%) was obtained according to the same method as Synthesis Example 1 by using Intermediate I-20 (11.5 g, 27.3 mmol) and 1-bromo-2-iodobenzene (8.51 g, 30.1 mmol).

HRMS (70 eV, EI+): m/z calcd for $C_{24}H_{14}BrClS$: 447.9688, found: 448.

Elemental Analysis: C, 64%; H, 3%

Synthesis Example 22: Synthesis of Intermediate I-22

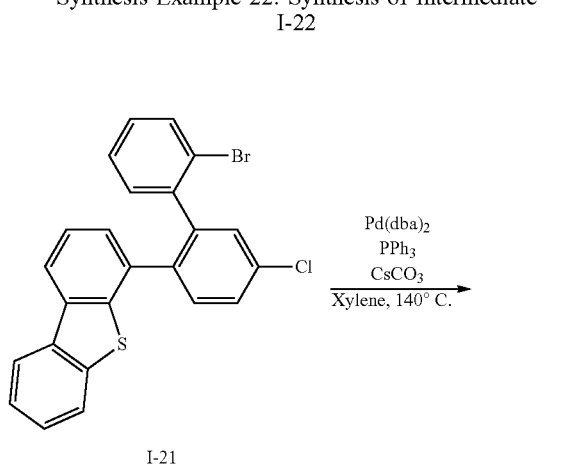

I-22

Intermediate I-22 (7.67 g, 85%) was obtained according to the same method as Synthesis Example 2 by using Intermediate I-21 (11 g, 24.5 mmol).

HRMS (70 eV, EI+): m/z calcd for $C_{24}H_{13}ClS$: 368.0426, found: 368.

Elemental Analysis: C, 78%; H, 4%

Synthesis Example 23: Synthesis of Intermediate I-23

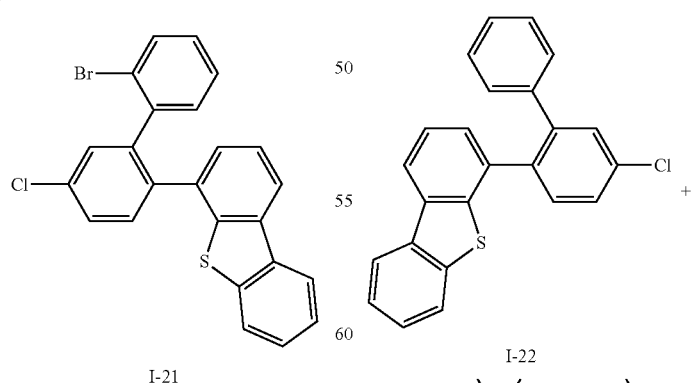

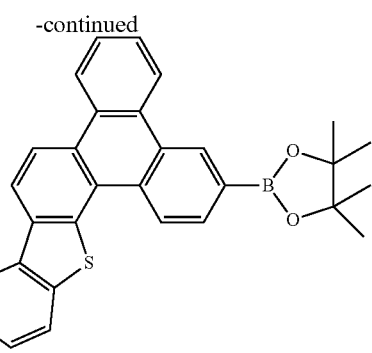

I-23

Intermediate I-23 (6.47 g, 74%) was obtained according to the same method as Synthesis Example 4 by using Intermediate I-22 (7 g, 19.0 mmol).

HRMS (70 eV, EI+): m/z calcd for C30H25BO2S: 460.1668, found: 460.

Elemental Analysis: C, 78%; H, 5%

Synthesis Example 24: Synthesis of Compound A-1

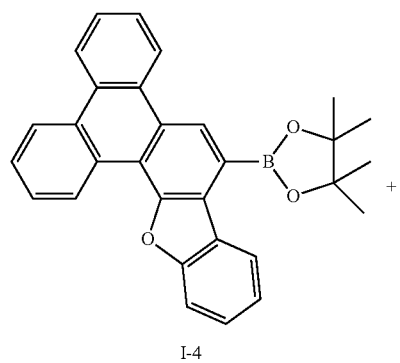

Compound A-1 (11.3 g, 91%) was obtained according to the same method as Synthesis Example 1 by using Intermediate I-4 (10 g, 22.5 mmol) and 2-chloro-4,6-diphenyl-1,3,5-triazine (6.02 g, 22.5 mmol) purchased from Tokyo Chemical Industry Co., Ltd. (http://www.tcichemicals.com/).

HRMS (70 eV, EI+): m/z calcd for $C_{39}H_{23}N_3O$: 549.1841, found: 549.

Elemental Analysis: C, 85%; H, 4%

Synthesis Example 25: Synthesis of Compound A-2

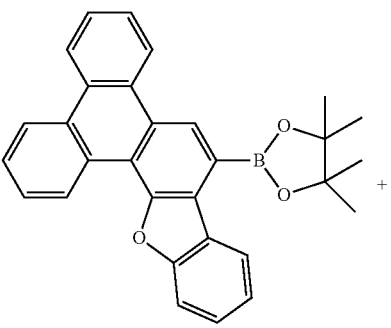

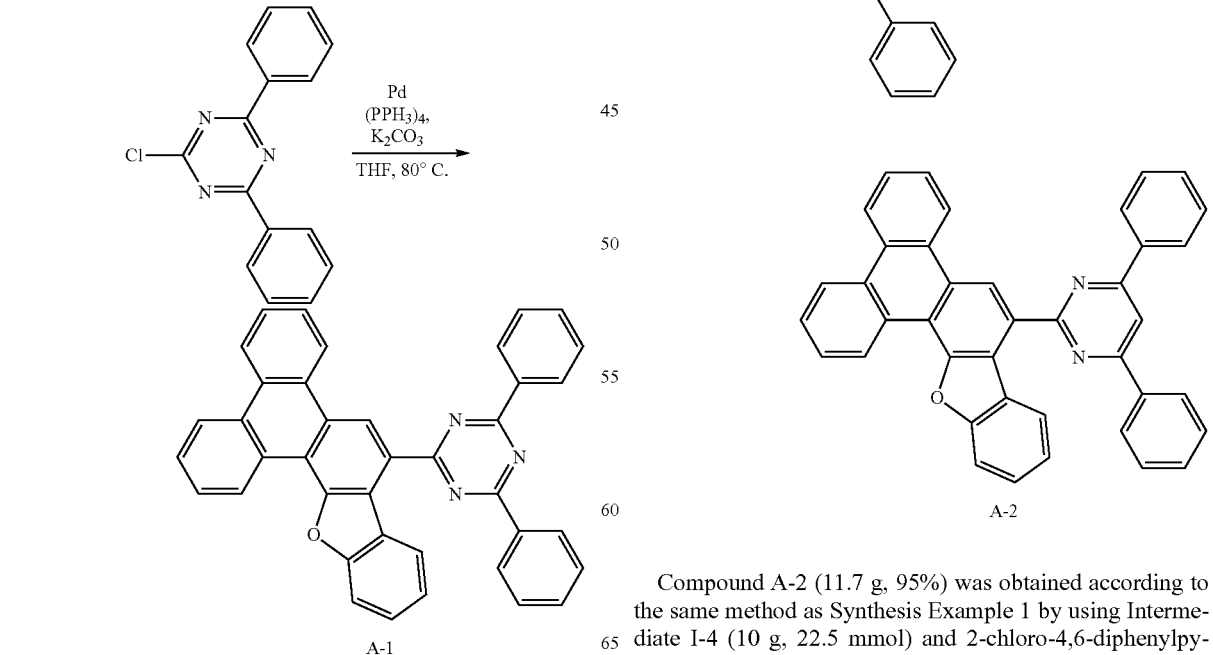

Compound A-2 (11.7 g, 95%) was obtained according to the same method as Synthesis Example 1 by using Intermediate I-4 (10 g, 22.5 mmol) and 2-chloro-4,6-diphenylpyrimidine (6.0 g, 22.5 mmol) purchased from Tokyo Chemical Industry Co., Ltd. (http://www.tcichemicals.com/).

HRMS (70 eV, EI+): m/z calcd for C40H24N2O: 548.1889, found: 548.

Elemental Analysis: C, 88%; H, 4%

Synthesis Example 26: Synthesis of Compound A-9

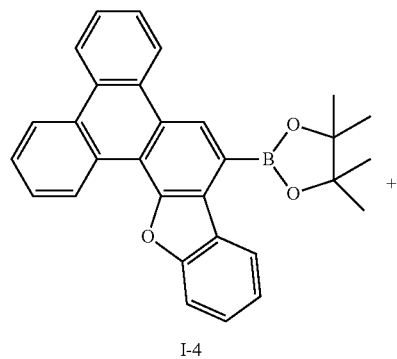

HRMS (70 eV, EI+): m/z calcd for $C_{45}H_{27}N_3O$: 625.2154, found: 625.

Elemental Analysis: C, 86%; H, 4%

Synthesis Example 27: Synthesis of Compound A-21

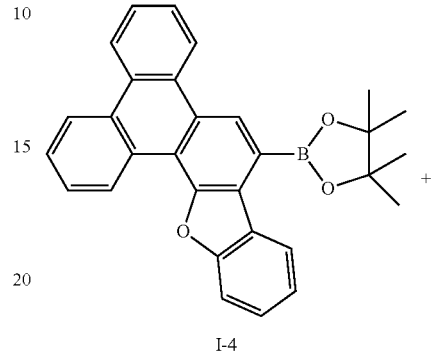

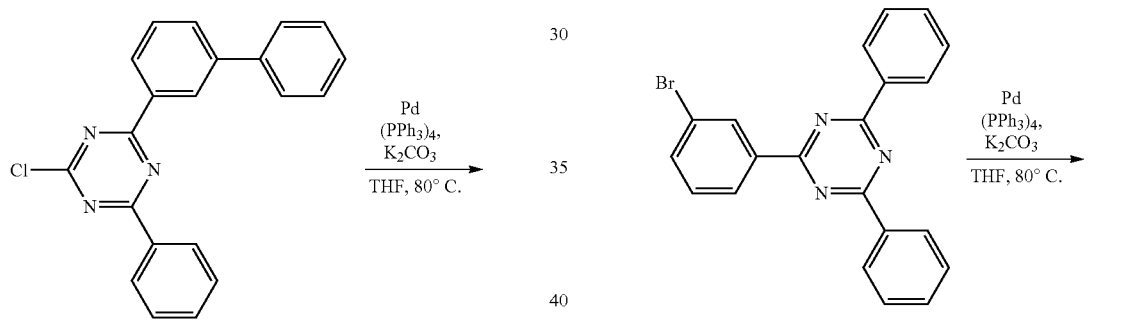

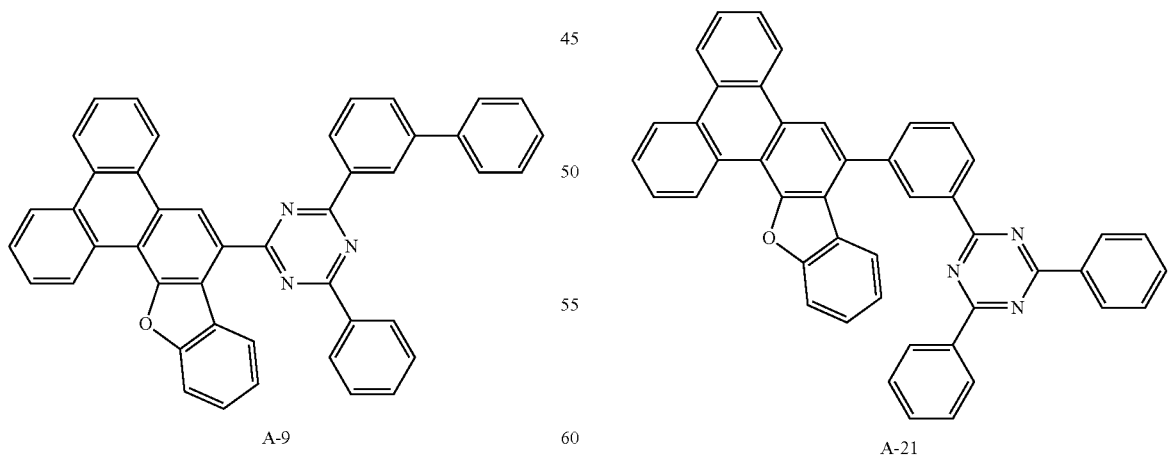

Compound A-9 (12.7 g, 90%) was obtained according to the same method as Synthesis Example 1 by using Intermediate I-4 (10 g, 22.5 mmol) and 2-(biphenyl-3-yl)-4-chloro-6-phenyl-1,3,5-triazine (7.74 g, 22.5 mmol) purchased from Richest Group Limited (http://www.richest-group.com/).

Compound A-21 (13.4 g, 95%) was obtained according to the same method as Synthesis Example 1 by using Intermediate I-4 (10 g, 22.5 mmol) and 2-(3-bromophenyl)-4,6-diphenyl-1,3,5-triazine (8.74 g, 22.5 mmol) purchased from Richest Group Limited (http://www.richest-group.com/).

HRMS (70 eV, EI+): m/z calcd for $C_{45}H_{27}N_3O$: 625.2154, found: 625.

Elemental Analysis: C, 86%; H, 4%

Synthesis Example 28: Synthesis of Compound A-54

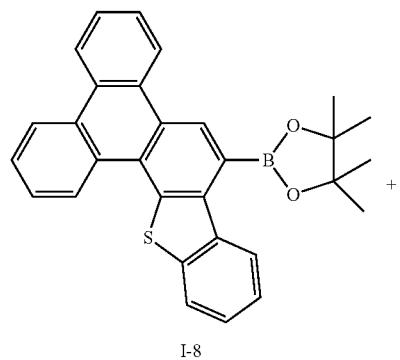

I-8

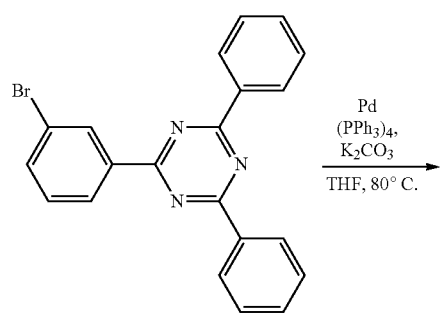

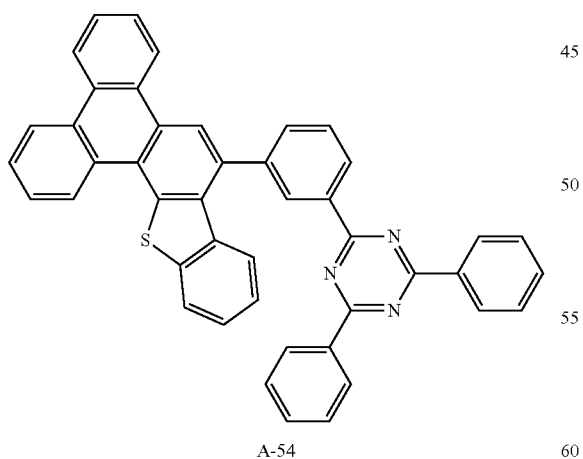

A-54

Compound A-54 (13.4 g, 96%) was obtained according to the same method as Synthesis Example 1 by using Intermediate I-8 (10 g, 21.7 mmol) and 2-(3-bromophenyl)-4,6-diphenyl-1,3,5-triazine (8.43 g, 21.7 mmol) purchased from Richest Group Limited (http://www.richest-group.com/).

HRMS (70 eV, EI+): m/z calcd for C45H27N3S: 641.1926, found: 641.

Elemental Analysis: C, 84%; H, 4%

Synthesis Example 29: Synthesis of Compound A-72

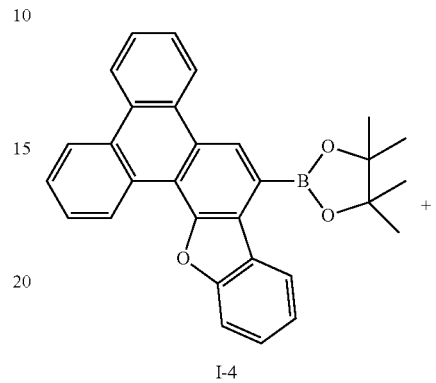

I-4

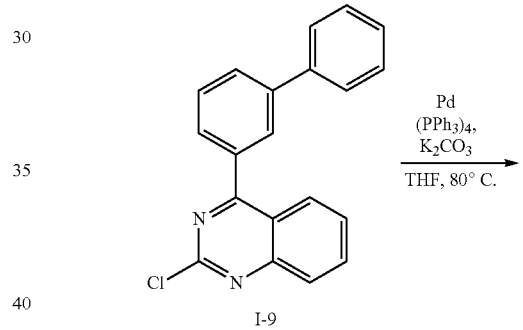

I-9

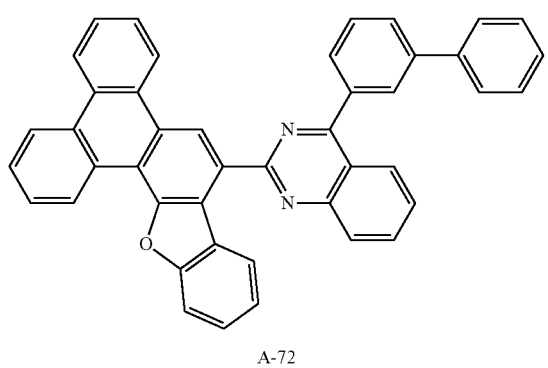

A-72

Compound A-72 (12.3 g, 91%) was obtained according to the same method as Synthesis Example 1 by using Intermediate I-4 (10 g, 22.5 mmol) and Intermediate I-9 (7.13 g, 22.5 mmol).

HRMS (70 eV, EI+): m/z calcd for $C_{44}H_{26}N_2O$: 598.2045, found: 598.

Elemental Analysis: C, 88%; H, 4%

Synthesis Example 30: Synthesis of Compound A-75

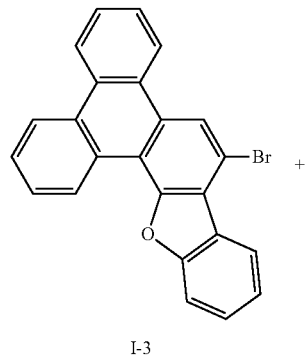
I-3

+

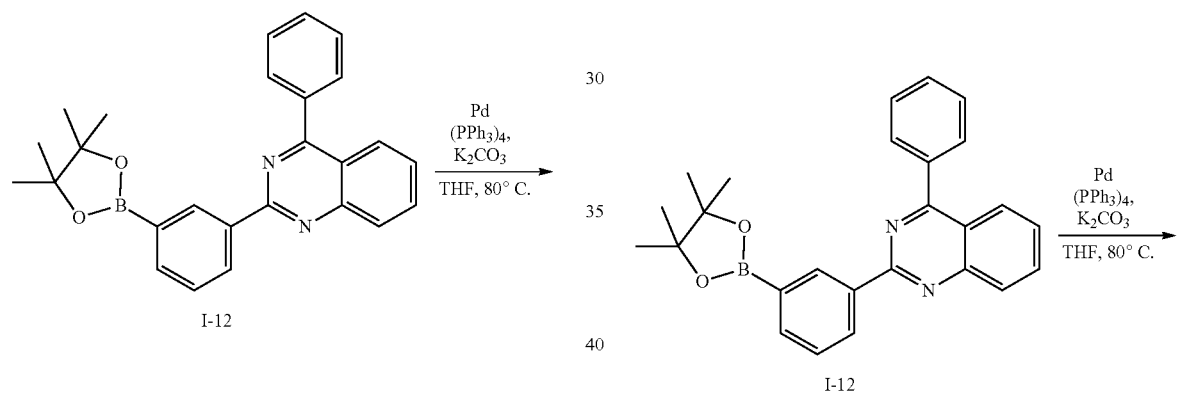

Compound A-75 (13.3 g, 88%) was obtained according to the same method as Synthesis Example 1 by using Intermediate I-3 (10 g, 25.2 mmol) and Intermediate I-12 (10.3 g, 25.2 mmol).

HRMS (70 eV, EI+): m/z calcd for $C_{44}H_{26}N_2O$: 598.2045, found: 598.

Elemental Analysis: C, 88%; H, 4%

Synthesis Example 31: Synthesis of Compound A-91

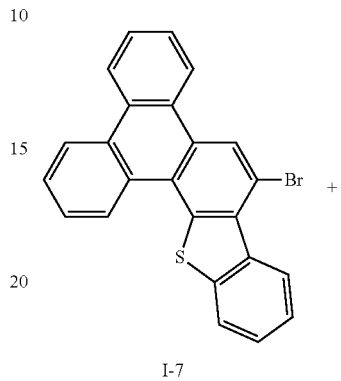
I-7

+

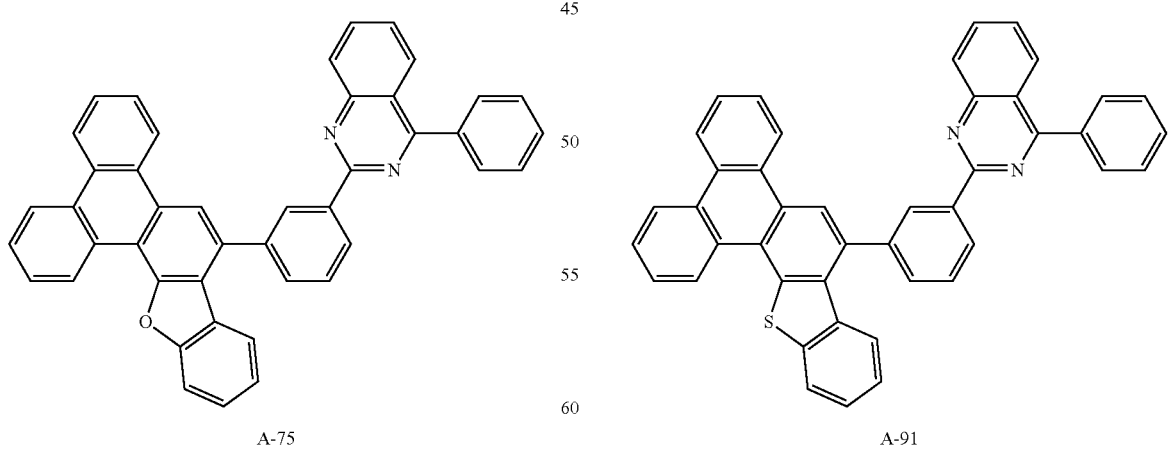

Compound A-91 (13.7 g, 92%) was obtained according to the same method as Synthesis Example 1 by using Intermediate I-7 (10 g, 24.2 mmol) and Intermediate I-12 (9.88 g, 24.2 mmol).

HRMS (70 eV, EI+): m/z calcd for C44H26N2S: 614.1817, found: 614.

Elemental Analysis: C, 86%; H, 4%

Synthesis Example 32: Synthesis of Compound A-106

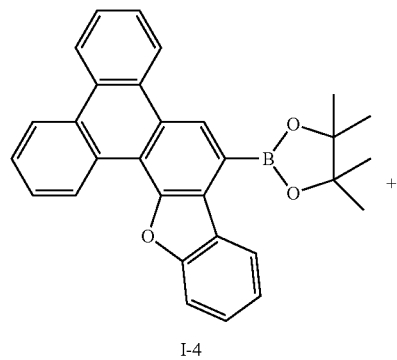

I-4

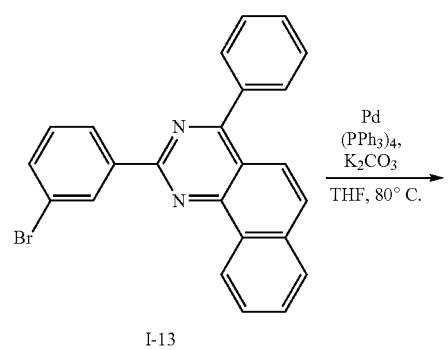

I-13

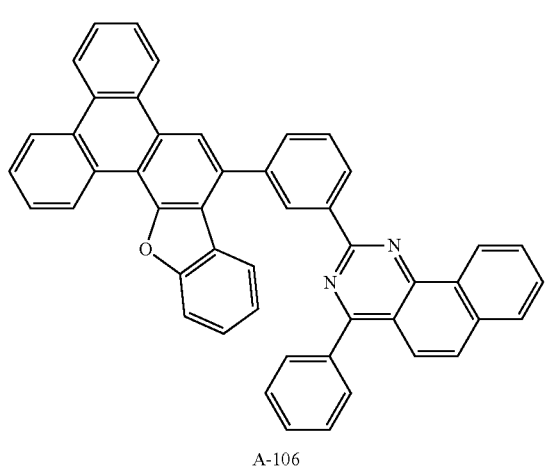

A-106

Compound A-106 (13.6 g, 93%) was obtained according to the same method as Synthesis Example 1 by using Intermediate I-4 (10 g, 22.5 mmol) and Intermediate I-13 (9.25 g, 22.5 mmol).

HRMS (70 eV, EI+): m/z calcd for C48H28N2O: 648.2202, found: 648.

Elemental Analysis: C, 89%; H, 4%

Synthesis Example 33: Synthesis of Compound B-9

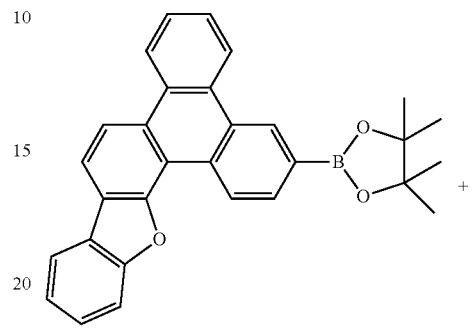

I-18

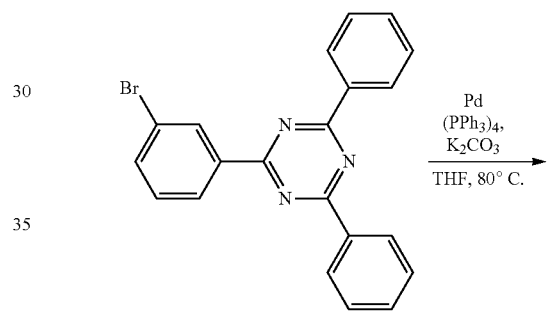

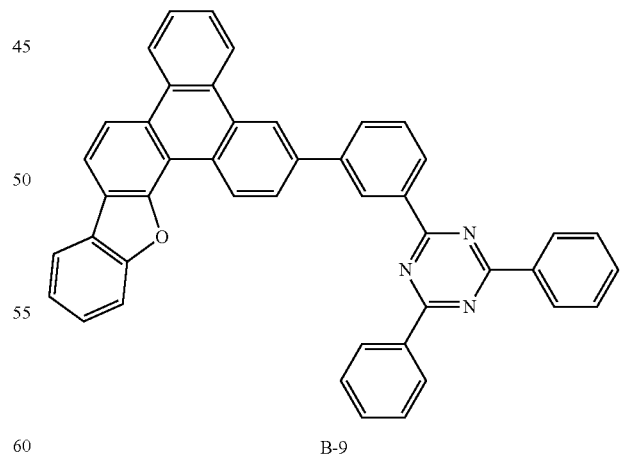

B-9

Compound B-9 (3.93 g, 93%) was obtained according to the same method as Synthesis Example 1 by using Intermediate I-18 (3 g, 6.75 mmol) and 2-(3-bromophenyl)-4,6-diphenyl-1,3,5-triazine (2.62 g, 6.75 mmol) purchased from Richest Group Limited (http://www.richest-group.com/).

HRMS (70 eV, EI+): m/z calcd for C45H27N3O: 625.2154, found: 625.
Elemental Analysis: C, 86%; H, 4%

Synthesis Example 34: Synthesis of Compound B-29

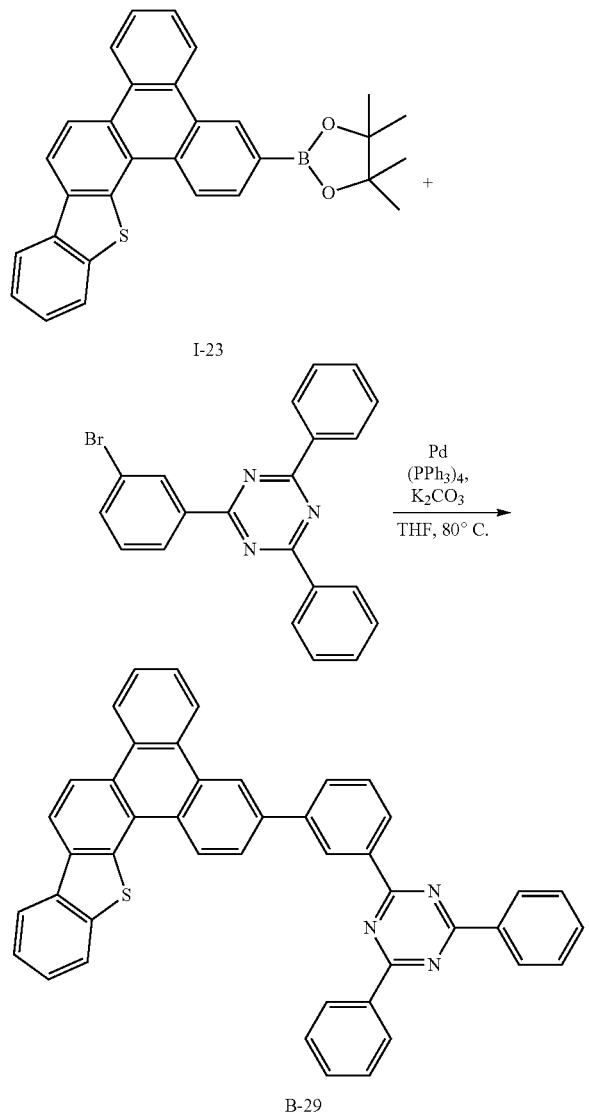

Compound B-29 (6.23 g, 89%) was obtained according to the same method as Synthesis Example 1 by using Intermediate I-23 (5 g, 10.9 mmol) and 2-(3-bromophenyl)-4,6-diphenyl-1,3,5-triazine (4.22 g, 10.9 mmol) purchased from Richest Group Limited (http://www.richest-group.com/).

HRMS (70 eV, EI+): m/z calcd for C45H27N3S: 641.1926, found: 641.
Elemental Analysis: C, 84%; H, 4%

Manufacture of Organic Light Emitting Diode (Green)

Example 1

An organic light emitting diode was manufactured by using Compound A-1 obtained in Synthesis Example 24 as a host and Ir(PPy)$_3$ as a dopant.

A 1000 Å-thick ITO was used as an anode, and a 1000 Å-thick aluminum (Al) as a cathode. Specifically, the organic light emitting diode was manufactured in a method of cutting an ITO glass substrate having sheet resistance of 15 Ω/cm$^2$ into a size of 50 mm×50 mm×0.7 mm, ultrasonic wave-cleaning it in acetone, isopropylalcohol, and pure water respectively for 15 minutes and UV ozone-cleaning it for 30 minutes.

On the substrate, an 800 Å-thick hole transport layer was formed by depositing N4,N4'-di(naphthalen-1-yl)-N4,N4'-diphenylbiphenyl-4,4'-diamine (NPB) (80 nm) under a vacuum degree of 650×10$^{-7}$ Pa at a deposition rate of 0.1 to 0.3 nm/s. Subsequently, a 300 Å-thick film as a light emitting layer was formed by using Compound A-1 according to Synthesis Example 24 under the same vacuum deposition condition as above, and herein, Ir(PPy)$_3$ as a phosphorescent dopant was simultaneously deposited. Herein, the phosphorescent dopant was deposited in an amount of 7 wt % based on 100 wt % of a total amount of the light emitting layer by adjusting deposition rates.

On the light emitting layer, a 50 Å-thick film as a hole blocking layer was formed by depositing bis(2-methyl-8-quinolinolate)-4-(phenylphenolato)aluminum (BAlq) under the same vacuum deposition condition as above. Subsequently, a 200 Å-thick film as an electron transport layer was formed by depositing Alq$_3$ under the same vacuum deposition condition as above. On the electron transport layer, LiF and Al were sequentially deposited as a cathode, manufacturing the organic photoelectric element.

A structure of the organic photoelectric element was ITO/NPB (80 nm)/EML (Compound A-1 (93 wt %)+Ir (PPy)$_3$ (7 wt %), (30 nm))/BAlq (5 nm)/Alq$_3$ (20 nm)/LiF (1 nm)/Al (100 nm).

Examples 2 to 7

Each organic light emitting diode according to Examples 2 to 7 was manufactured according to the same method as Example 1 except that the compounds of Table 1 were used instead of Compound A-1 of Example 1.

Comparative Examples 1 to 4

Each organic light emitting diode according to Comparative Example 1 to Comparative Example 4 was manufactured according to the same method as Example 1 except that 4,4'-di(9-carbazol-9-yl)biphenyl (CBP), or the following compounds of Host 1, Host 2, and Host 3 was used respectively instead of Compound A-1 according to Synthesis Example 24.

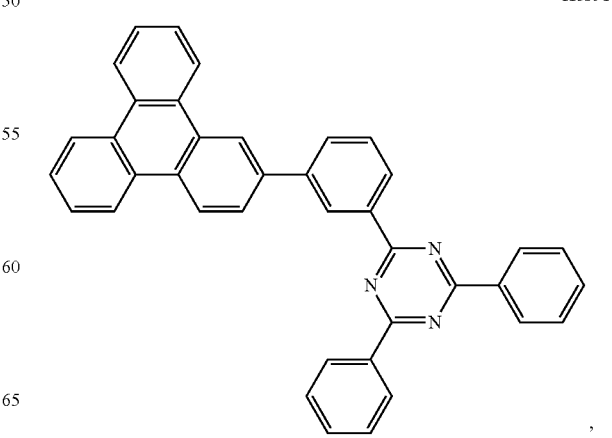

Host 1

-continued

Host 2

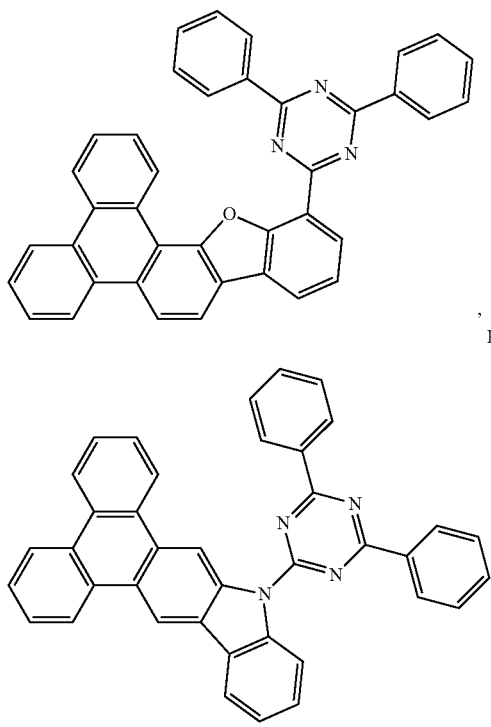

, Host 3

Evaluation I

Current density change, luminance change, and luminous efficiency depending on a voltage of each organic light emitting diode according to Examples 1 to 7 and Comparative Examples 1 to 4 were measured.

Specific measurement methods are as follows, and the results are shown in Table 1.

(1) Measurement of Current Density Change Depending on Voltage Change

The obtained organic light emitting diodes were measured regarding a current value flowing in the unit element, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Driving Voltage

A driving voltage of each diode was measured using a current-voltage meter (Keithley 2400) at 15 mA/cm$^2$.

TABLE 1

| No. | Compound | Driving voltage (V) | Color (EL color) | Efficiency (cd/A) |
|---|---|---|---|---|
| Example 1 | A-1 | 3.44 | Green | 89.5 |
| Example 2 | A-2 | 3.46 | Green | 89.9 |
| Example 3 | A-9 | 3.48 | Green | 90.0 |
| Example 4 | A-21 | 3.50 | Green | 90.1 |

TABLE 1-continued

| No. | Compound | Driving voltage (V) | Color (EL color) | Efficiency (cd/A) |
|---|---|---|---|---|
| Example 5 | A-54 | 3.52 | Green | 91.5 |
| Example 6 | B-9 | 3.51 | Green | 89.2 |
| Example 7 | B-29 | 3.49 | Green | 88.9 |
| Comparative Example 1 | CBP | 4.80 | Green | 31.4 |
| Comparative Example 2 | Host 1 | 3.65 | Green | 79.8 |
| Comparative Example 3 | Host 2 | 4.32 | Green | 80.2 |
| Comparative Example 4 | Host 3 | 4.10 | Green | 85.0 |

According to the results of Table 1, it may be confirmed that the driving voltages of Examples 1 to 7 are significantly lower than those of Comparative Examples 1 to 4 and efficiency thereof is improved to be equal to or more than that of Comparative Examples 1 to 4.

Manufacture of Organic Light Emitting Diode (Red)

Example 8

An organic light emitting diode was manufactured by using Compound A-72 according to Synthesis Example 29 as a host and acetylacetonatobis(2-phenylquinolinato) iridium (Ir(pq)$_2$acac) as a dopant.

As for an anode, 1500 Å-thick ITO was used, and as for a cathode, 1000 Å-thick aluminum (Al) was used. Specifically, illustrating a method of manufacturing the organic light emitting diode, the anode is manufactured by cutting an ITO glass substrate having 15 Ω/cm$^2$ of a sheet resistance into a size of 50 mm×50 mm×0.7 mm, ultrasonic wave-washing them in acetone, isopropylalcohol, and pure water for 15 minutes respectively, and UV ozone cleaning them for 30 minutes.

On the substrate, a 600 Å-thick hole transport layer (HTL) was formed by vacuum-depositing 4,4'-bis[N-[4-{N,N-bis (3-methylphenyl)amino}-phenyl]-N-phenylamino]biphenyl [DNTPD] under a vacuum degree of 650×10$^{-7}$ Pa at a deposition rate of 0.1 to 0.3 nm/s. Subsequently, a 300 Å-thick hole transport layer was formed by vacuum-depositing HT-1 (N-(biphenyl-4-yl)-N-(4-(9-phenyl-9H-carbazol-3-yl)phenyl)biphenyl-4-amine) under the same vacuum deposition condition. Then, a 300 Å-thick light emitting layer was formed by using Compound A-72 according to Synthesis Example 29 under the same vacuum deposition condition, and acetylacetonatobis(2-phenylquinolinato) iridium (Ir(pq)$_2$acac) that is a phosphorescent dopant was simultaneously deposited. Herein, the phosphorescent dopant was deposited to be 7 wt % based on 100 wt % of a total weight of the light emitting layer by adjusting a deposition rate of the phosphorescent dopant.

On the light emitting layer, a 50 Å-thick hole blocking layer was formed by depositing bis(2-methyl-8-quinolinolate)-4-(phenylphenolato)aluminum (BAlq) under the same vacuum deposition condition. Subsequently, a 250 Å-thick electron transport layer was formed by depositing tris(8-hydroxyquinolinato)aluminum (Alq$_3$) under the same vacuum deposition condition. On the electron transport layer, a cathode is formed by sequentially depositing LiF and Al to manufacture an organic light emitting diode.

A structure of the organic light emitting diode was ITO/DNTPD (60 nm)/HT-1 (30 nm)/EML (Compound A-72 (93 wt %)+Ir (pq)$_2$acac (7 wt %), 30 nm)/Balq (5 nm)/Alq$_3$ (25 nm)/LiF (1 nm)/Al (100 nm).

Examples 9 to 11

Each organic light emitting diode according to Example 9 to Example 11 was manufactured according to the same method as Example 8 except that the compounds of Table 2 were used instead of Compound A-72 according to Synthesis Example 29.

Comparative Example 5

Each organic light emitting diode according to Comparative Example 5 was manufactured according to the same method as Example 8 except that 4,4'-di (9-carbazol-9-yl) biphenyl (CBP) was used instead of Compound A-72 according to Synthesis Example 29.

Evaluation II

Current density change, luminance change, and luminous efficiency depending on a voltage of each organic light emitting diode according to Examples 8 to 11 and Comparative Example 5 were measured in the same method in Evaluation I and the results are shown in Table 2.

TABLE 2

| No. | Compound | Driving voltage (V) | Color (EL color) | Efficiency (cd/A) |
| --- | --- | --- | --- | --- |
| Example 8 | A-72 | 5.0 | Red | 46.3 |
| Example 9 | A-75 | 5.5 | Red | 45.8 |
| Example 10 | A-91 | 5.7 | Red | 47.0 |
| Example 11 | A-106 | 4.8 | Red | 45.1 |
| Comparative Example 5 | CBP | 7.4 | Red | 37.2 |

Referring to Table 2, the organic light emitting diodes according to Examples 8 to 11 exhibited greatly improved luminous efficiency and driving voltage characteristics compared with the organic light emitting diode according to Comparative Example 5.

While this invention has been described in connection with what is presently considered to be practical example embodiments, it is to be understood that the invention is not limited to the disclosed embodiments. On the contrary, it is intended to cover various modifications and equivalent arrangements included within the spirit and scope of the appended claims. Therefore, the aforementioned embodiments should be understood to be exemplary but not limiting the present invention in any way.

The invention claimed is:

1. A compound for an organic optoelectronic device represented by Chemical Formula 1:

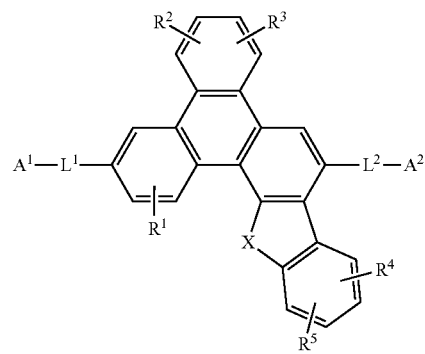

[Chemical Formula 1]

wherein, in Chemical Formula 1,

X is O or S,

R$^1$ to R$^5$ are independently hydrogen, deuterium, a substituted or unsubstituted C1 to C5 alkyl group, or a substituted or unsubstituted C6 to C18 aryl group, L$^1$ and L$^2$ are independently a single bond, a substituted or unsubstituted C6 to C20 arylene group, or a substituted or unsubstituted C2 to C30 heteroarylene group, A$^1$ and A$^2$ are independently hydrogen, deuterium, a substituted or unsubstituted C6 to C18 aryl group, or a substituted or unsubstituted C2 to C30 heterocyclic group, and at least one of A$^1$ and A$^2$ comprises a moiety represented by Chemical Formula A,

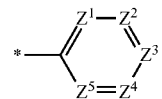

[Chemical Formula A]

wherein, in Chemical Formula A,

Z$^1$ to Z$^5$ are independently N or CR$^a$, at least one of Z$^1$ to Z$^5$ is N, R$^a$ is independently hydrogen, deuterium, a substituted or unsubstituted C1 to C5 alkyl group, or a substituted or unsubstituted C6 to C18 aryl group, R$^a$ is independently present or adjacent groups thereof are linked with each other to form a substituted or unsubstituted aliphatic, aromatic or heteroaromatic monocyclic or polycyclic ring, and

* is a linking point with L$^1$ or L$^2$ of Chemical Formula 1, wherein "substituted" refers to replacement of at least one hydrogen by deuterium, a cyano group, a C1 to C20 alkyl group, a C6 to C30 aryl group, or a C2 to C30 heteroaryl group.

2. The compound for an organic optoelectronic device of claim 1, wherein Chemical Formula A is represented by one of Chemical Formula A1, Chemical Formula A2, Chemical Formula A3, and Chemical Formula A4:

[Chemical Formula A1]

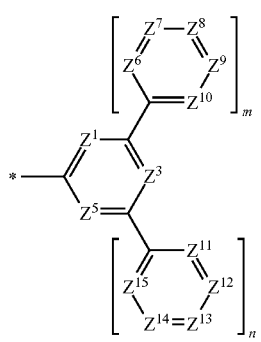

[Chemical Formula A2]

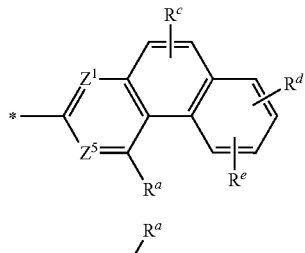

[Chemical Formula A3]

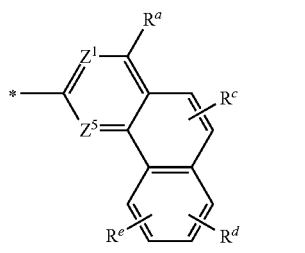

[Chemical Formula A4]

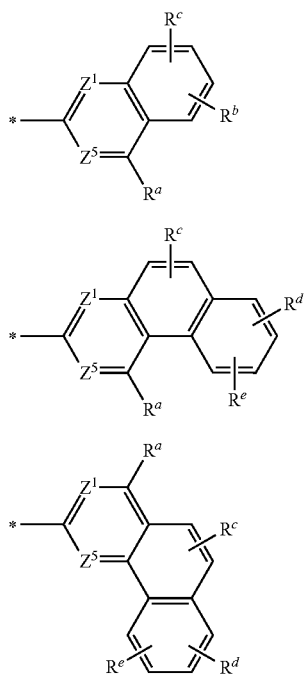

wherein, in Chemical Formula A1 to Chemical Formula A4, $Z^1$, $Z^3$, $Z^5$, and $Z^6$ to $Z^{15}$ are independently N or $CR^a$, at least one of $Z^1$, $Z^3$, $Z^5$, and $Z^6$ to $Z^{15}$ of Chemical Formula A1 is N, at least one of $Z^1$ and $Z^5$ of Chemical Formulae A2 to A4 is N, m and n are independently one of integers of 0 to 2, $R^a$ to $R^e$ are independently hydrogen, deuterium, a substituted or unsubstituted C1 to C5 alkyl group, or a substituted or unsubstituted C6 to C18 aryl group, and

* is a linking point with $L^1$ or $L^2$ of Chemical Formula 1.

3. The compound for an organic optoelectronic device of claim 1, wherein $A^1$ and $A^2$ are independently hydrogen, deuterium, a substituted or unsubstituted phenyl group, a substituted or unsubstituted biphenyl group, a substituted or unsubstituted naphthyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted benzoquinolinyl group, a substituted or unsubstituted benzoisoquinolinyl group, or a substituted or unsubstituted benzoquinazolinyl group, and at least one of $A^1$ and $A^2$ is a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolinyl group, a substituted or unsubstituted benzoquinolinyl group, a substituted or unsubstituted benzoisoquinolinyl group, or a substituted or unsubstituted benzoquinazolinyl group.

4. The compound for an organic optoelectronic device of claim 1, wherein Chemical Formula A is selected from substituents of Group I:

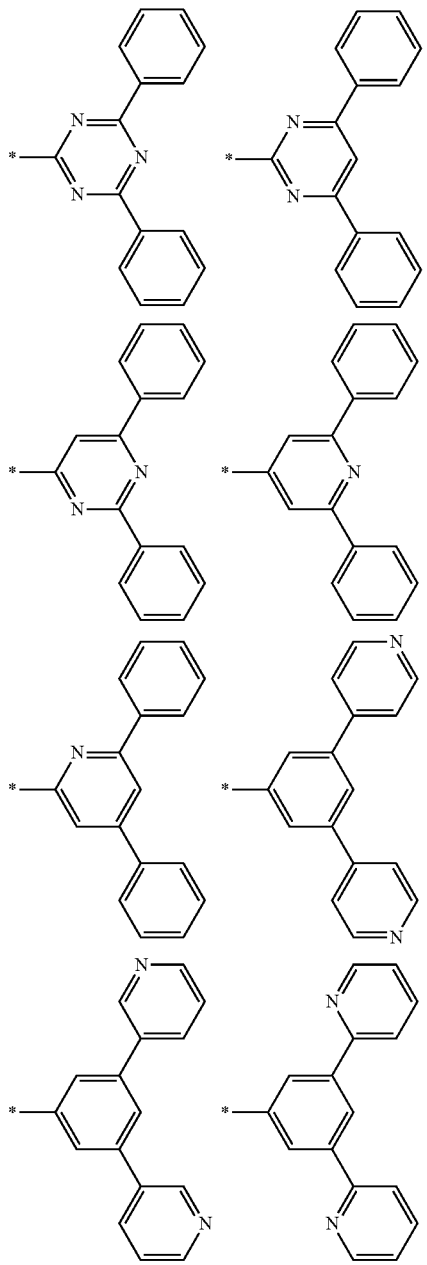

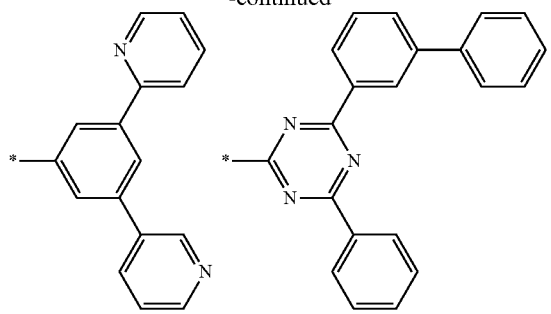
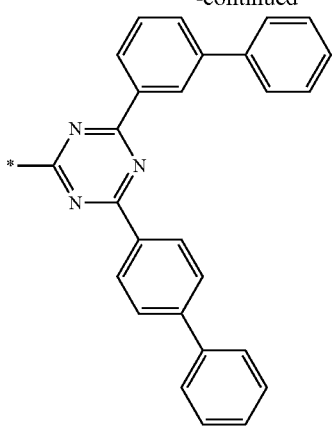
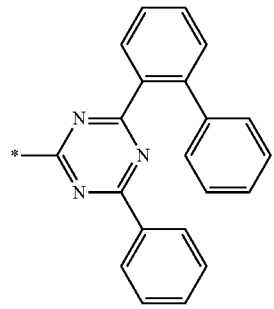
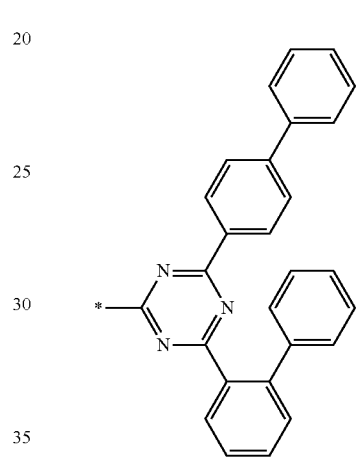
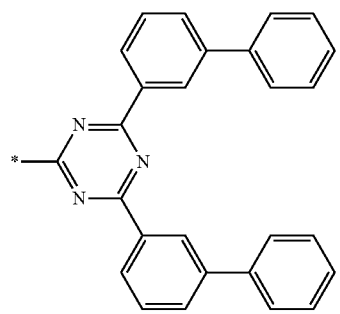
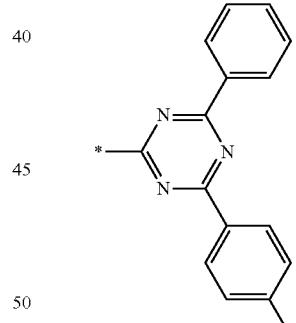
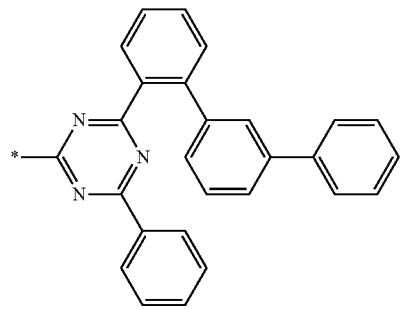
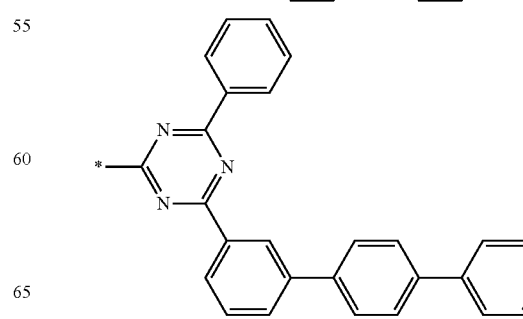
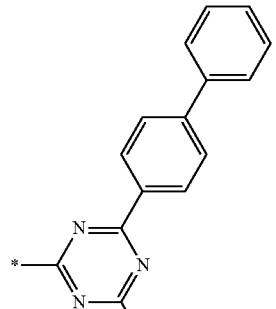
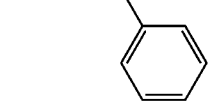

99
-continued
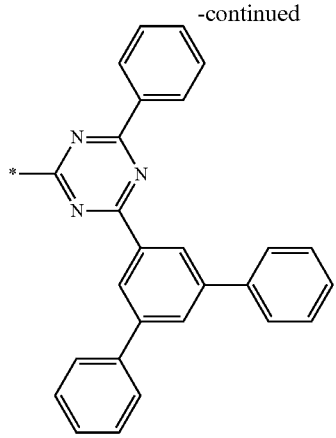
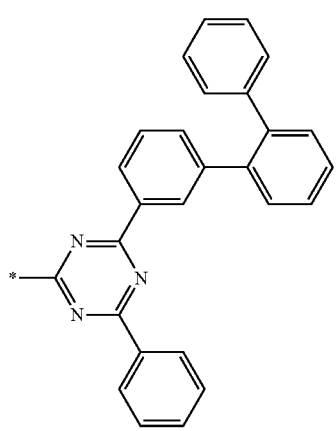
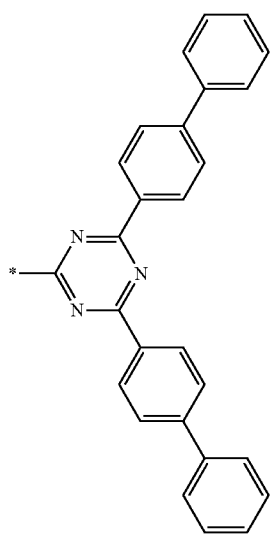
100
-continued
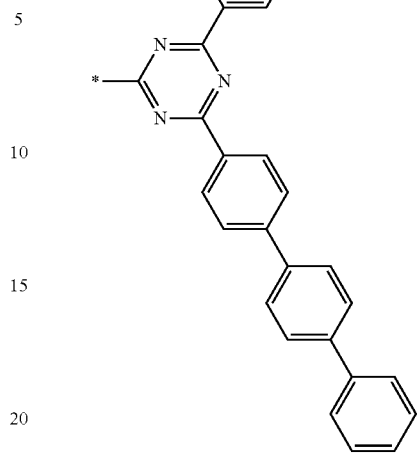
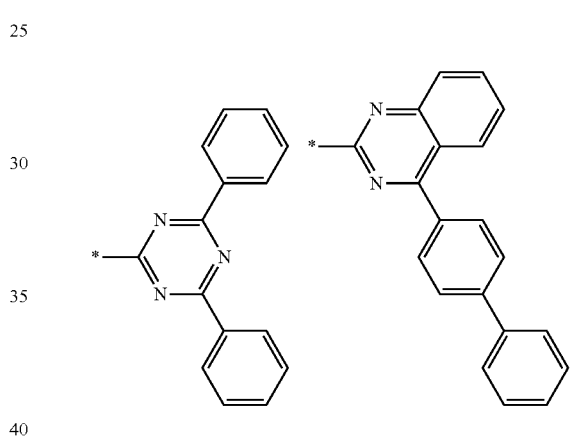
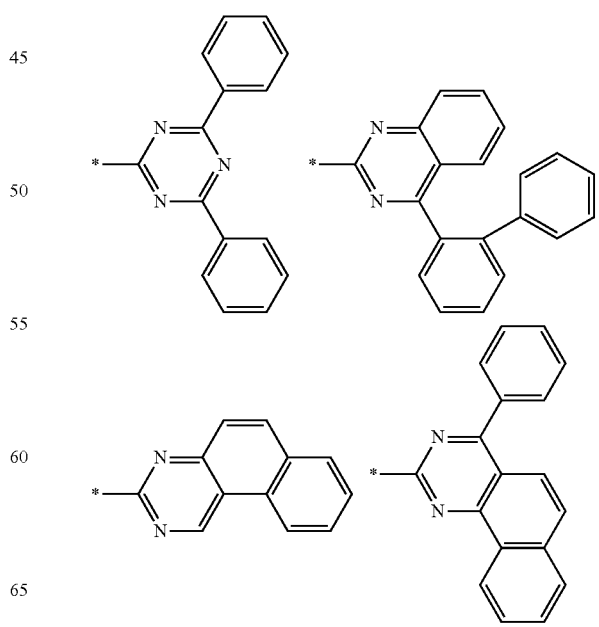

-continued

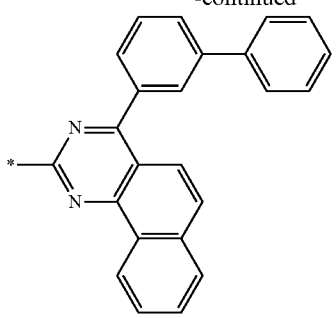

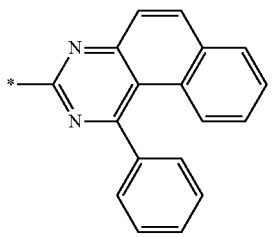

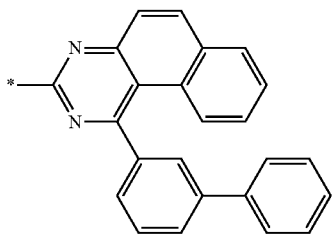

wherein, in Group I, * is a linking point with $L^1$ or $L^2$ of Chemical Formula 1.

5. The compound for an organic optoelectronic device of claim 1, which is represented by one of Chemical Formula 1-A1-a1, Chemical Formula 1-A1-a2, Chemical Formula 1-A1-b1, Chemical Formula 1-A1-b2, Chemical Formula 1-A2-a, Chemical Formula 1-A2-b, Chemical Formula 1-A3-a, Chemical Formula 1-A3-b, Chemical Formula 1-A4-a, and Chemical Formula 1-A4-b:

[Chemical Formula 1-A1-a1]

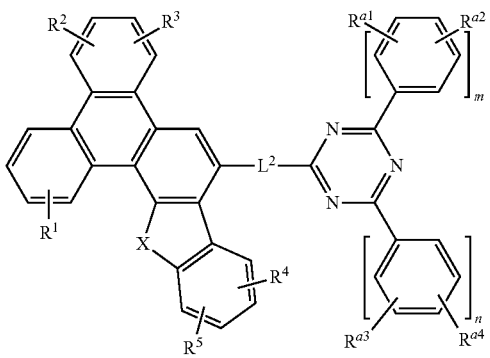

-continued

[Chemical Formula 1-A1-a2]

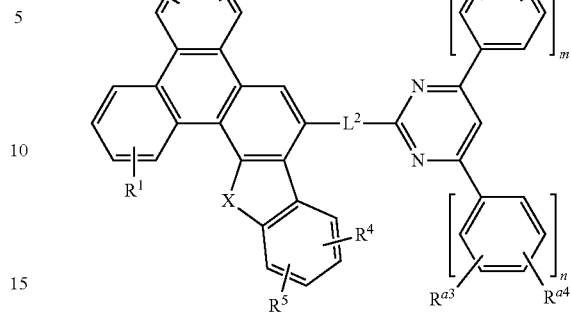

[Chemical Formula 1-A1-b1]

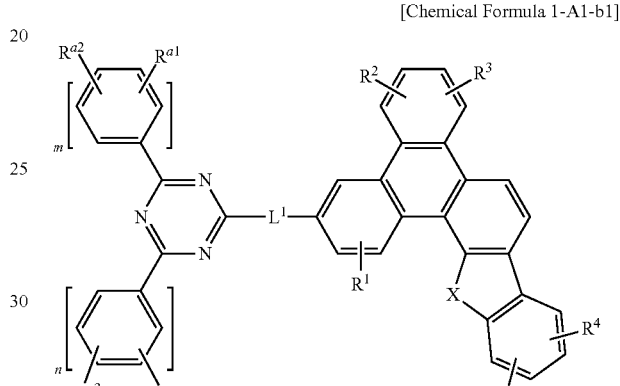

[Chemical Formula 1-A1-b2]

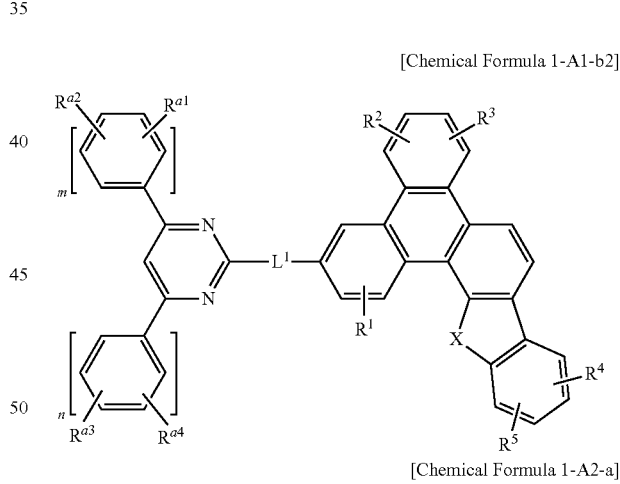

[Chemical Formula 1-A2-a]

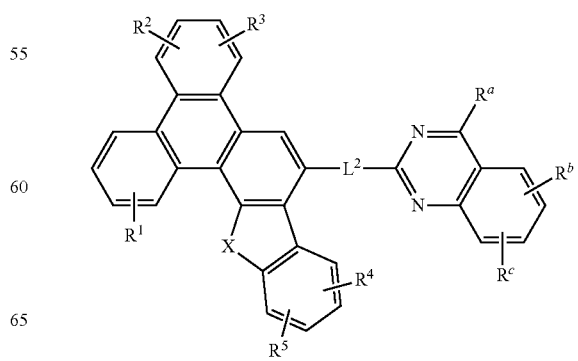

103
-continued

[Chemical Formula 1-A2-b]

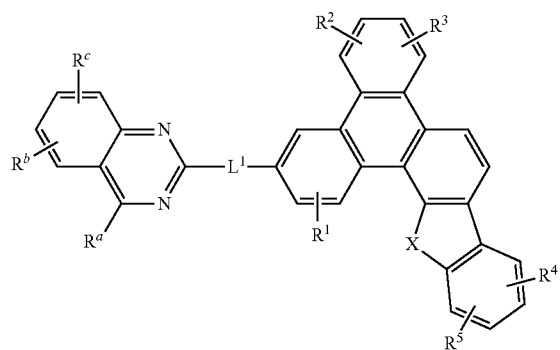

[Chemical Formula 1-A3-a]

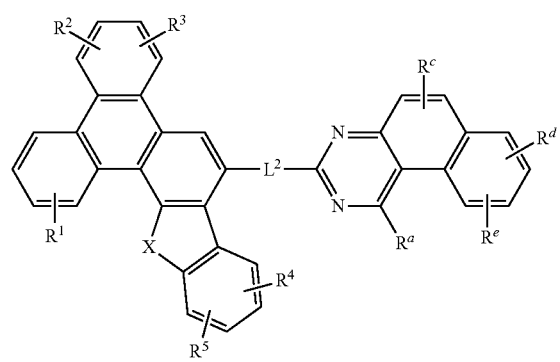

[Chemical Formula 1-A3-b]

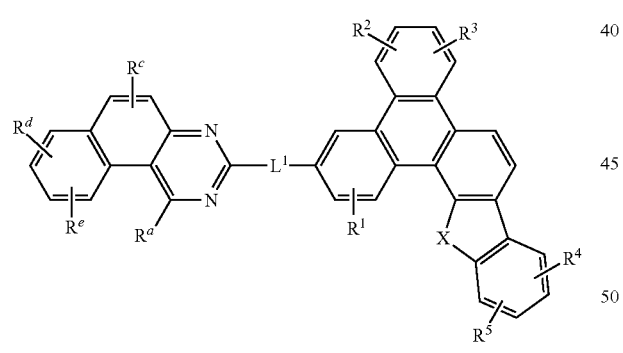

[Chemical Formula 1-A4-a]

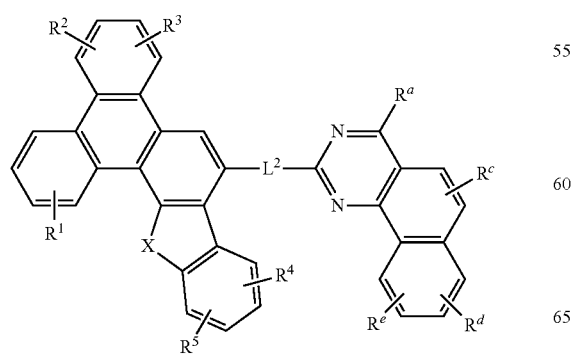

104
-continued

[Chemical Formula 1-A4-b]

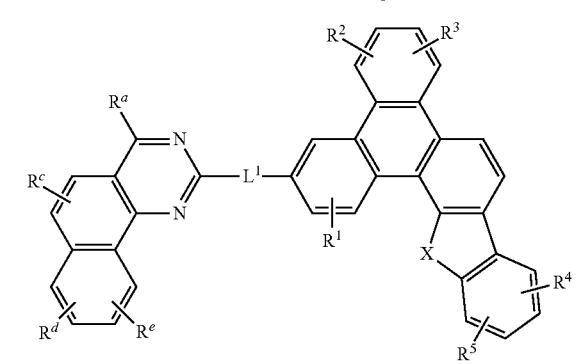

wherein, in Chemical Formula 1-A1-a1, Chemical Formula 1-A1-a2, Chemical Formula 1-A1-b1, Chemical Formula 1-A1-b2, Chemical Formula 1-A2-a, Chemical Formula 1-A2-b, Chemical Formula 1-A3-a, Chemical Formula 1-A3-b, Chemical Formula 1-A4-a and Chemical Formula 1-A4-b, X is O or S, $R^1$ to $R^5$, $R^a$, $R^{a1}$ to $R^{a4}$, $R^b$, $R^c$, $R^d$, and $R^e$ are independently hydrogen, deuterium, a substituted or unsubstituted C1 to C5 alkyl group, or a substituted or unsubstituted C6 to C12 aryl group, $L^1$ and $L^2$ are independently a single bond, or a substituted or unsubstituted C6 to C12 arylene group, and m and n are independently one of integers of 0 to 2.

6. The compound for an organic optoelectronic device of claim 1, which is selected from compounds of Group 1:

[Group 1]

[A-1]

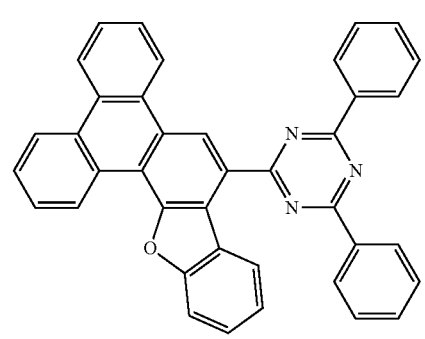

[A-2]

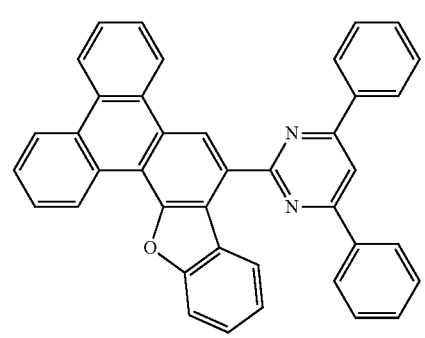

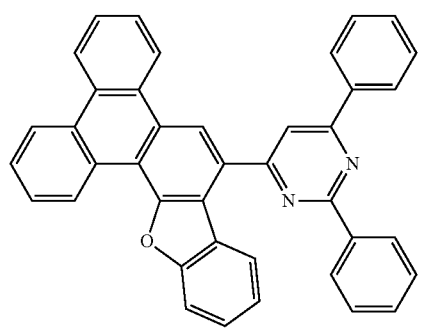 [A-3]
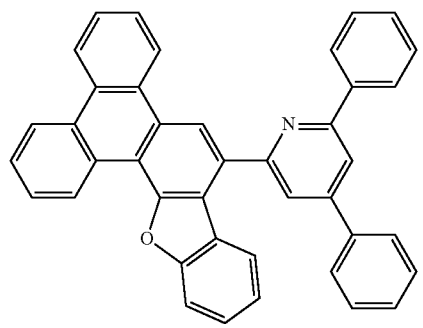 [A-4]
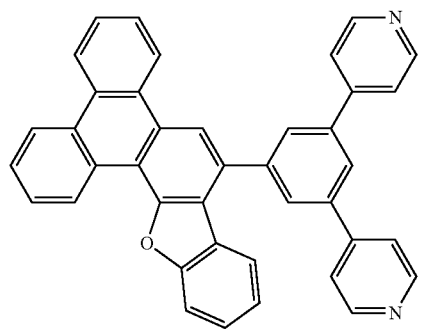 [A-5]
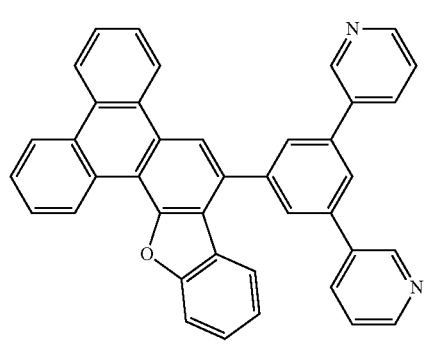 [A-6]
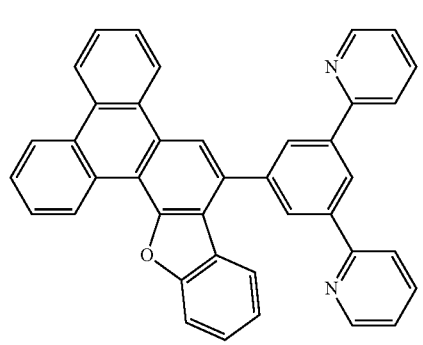 [A-7]
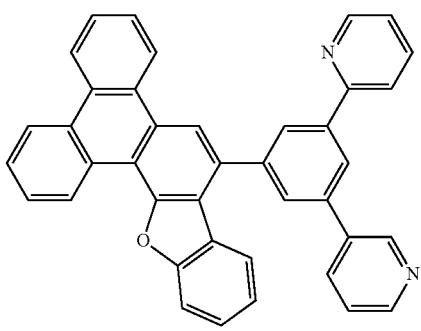 [A-8]
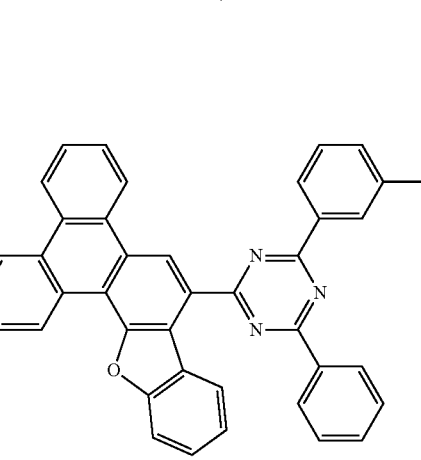 [A-9]
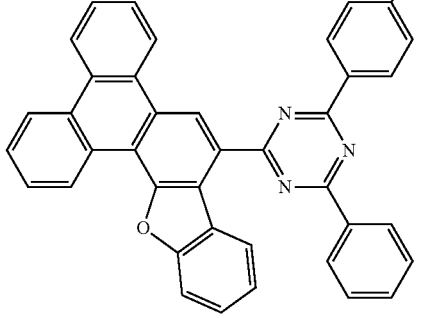 [A-10]
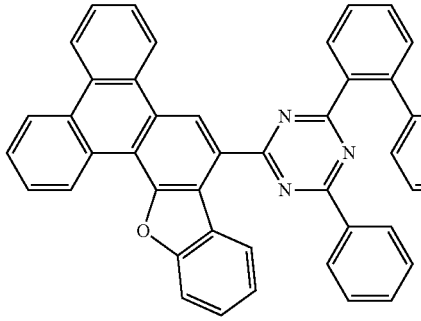 [A-11]

[A-12]
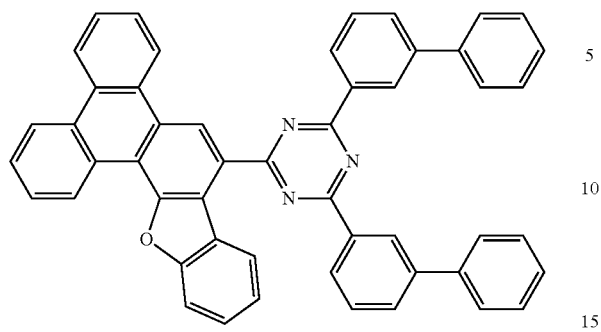
[A-13]
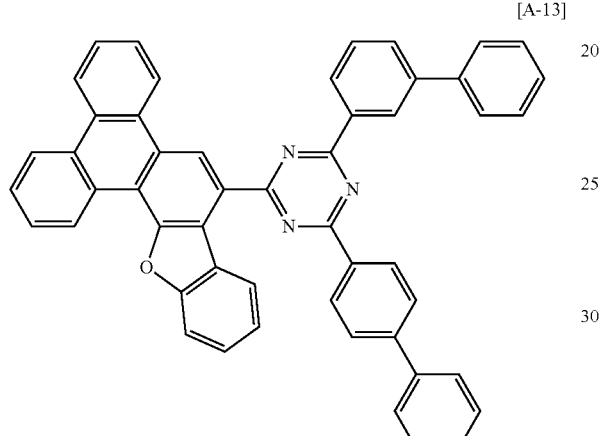
[A-14]
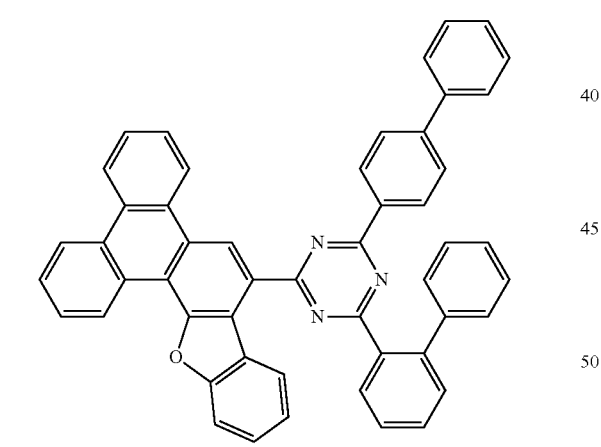
[A-15]
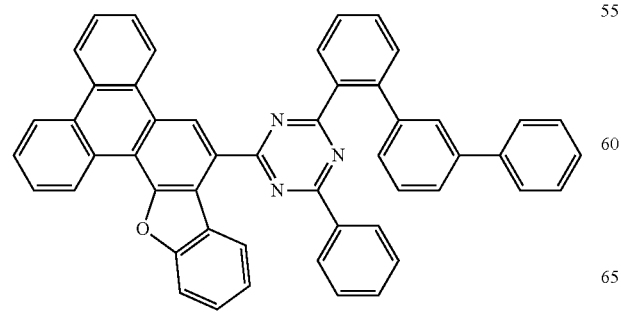
[A-16]
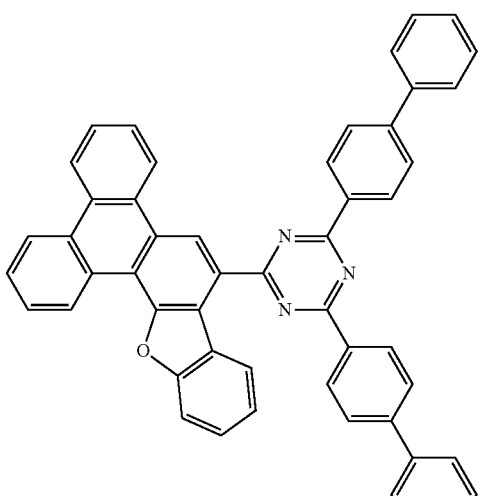
[A-17]
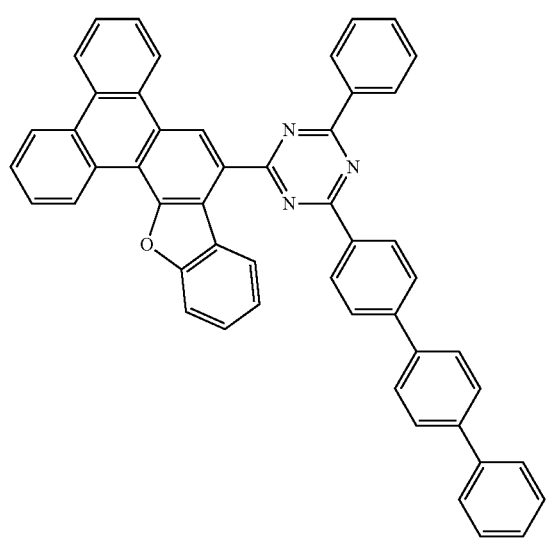
[A-18]
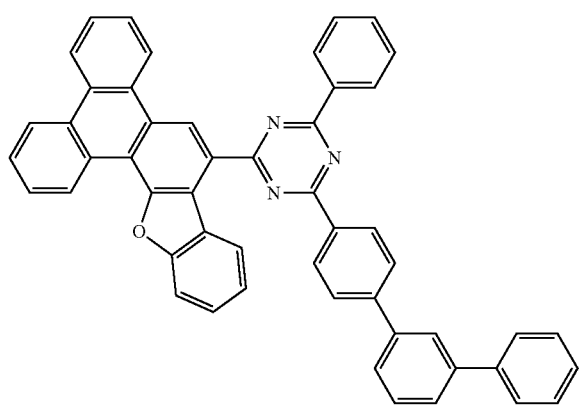

[A-19]
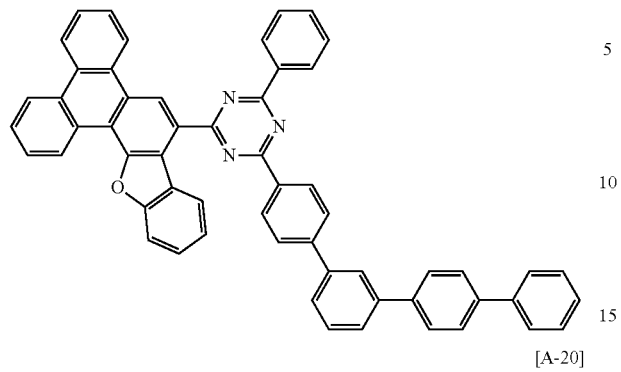
[A-23]
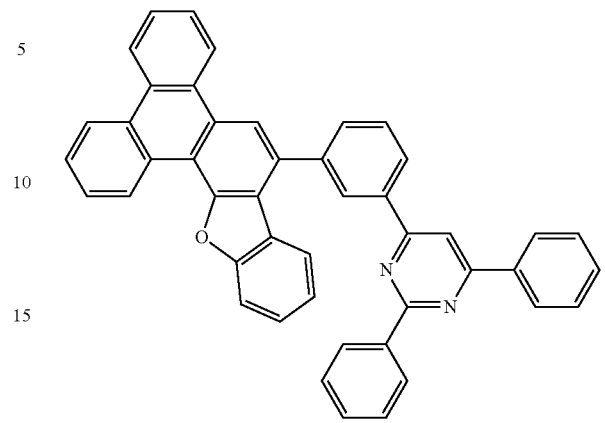
[A-20]
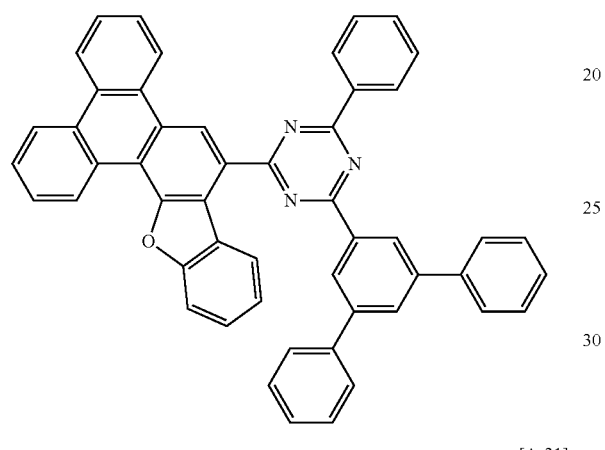
[A-24]
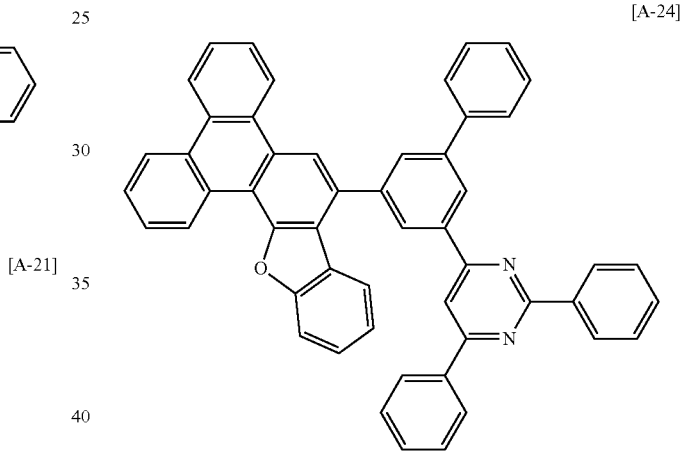
[A-21]
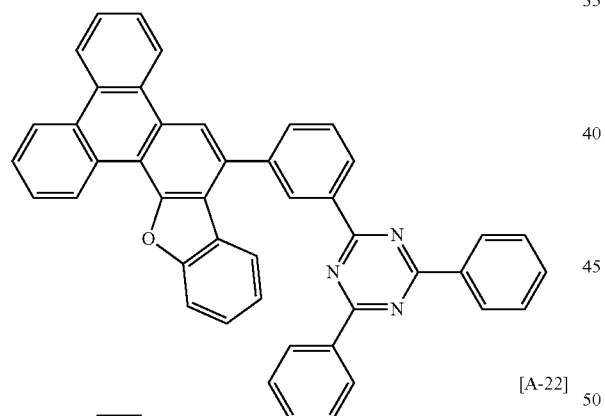
[A-22]
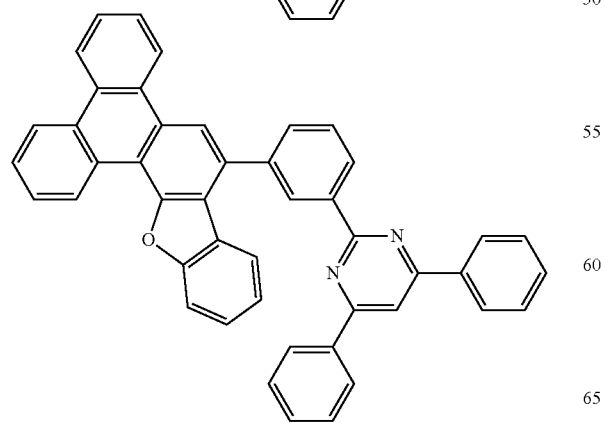
[A-25]
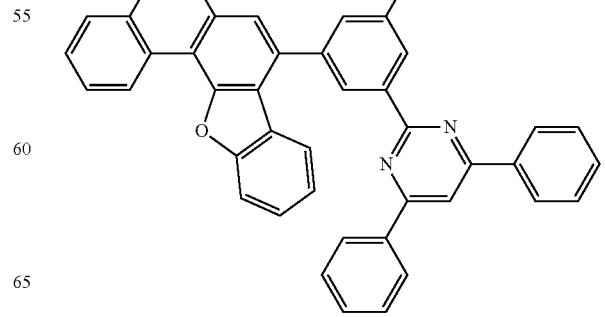

[A-26]
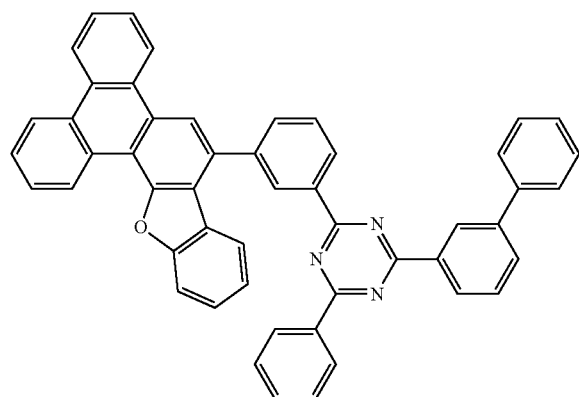
[A-27]
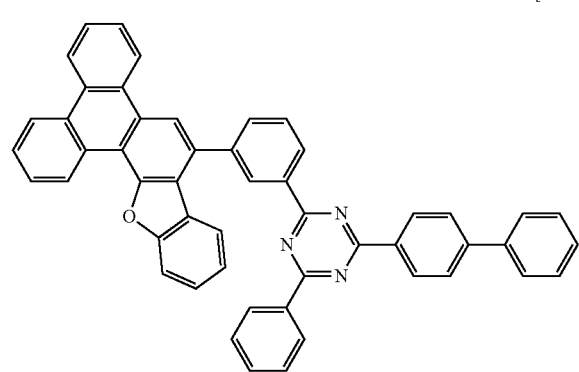
[A-28]
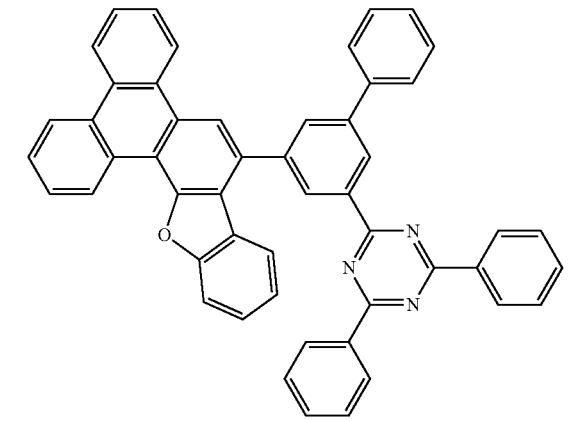
[A-29]
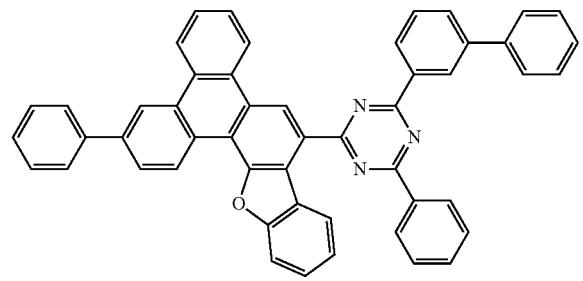
[A-30]
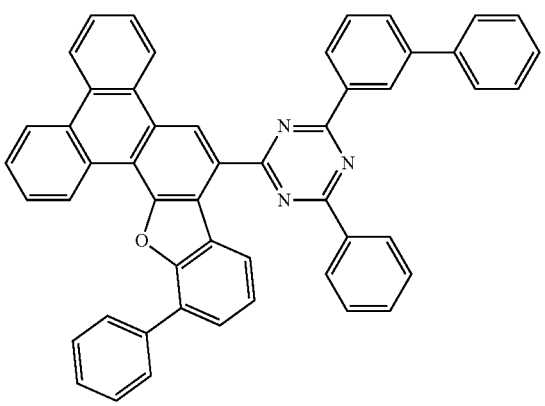
[A-31]
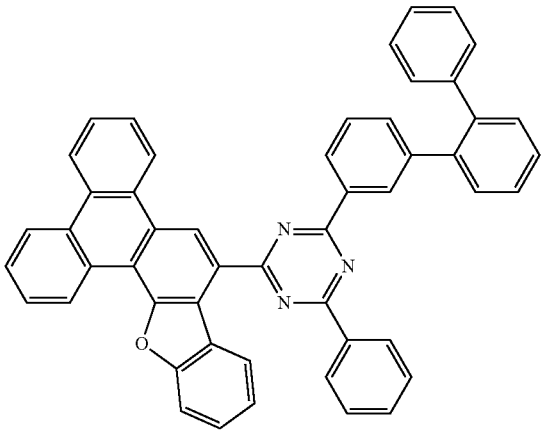
[A-32]
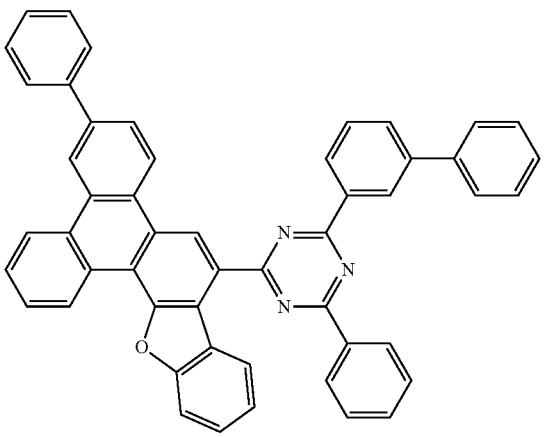
[A-33]
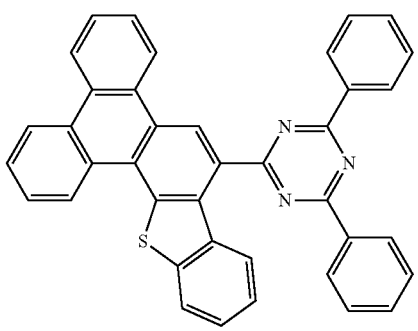

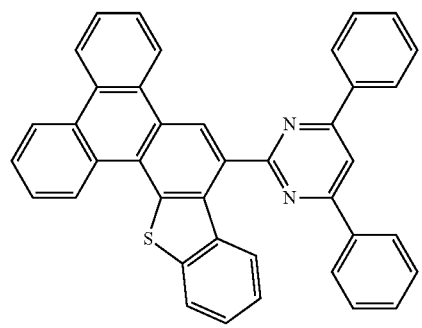 [A-34]
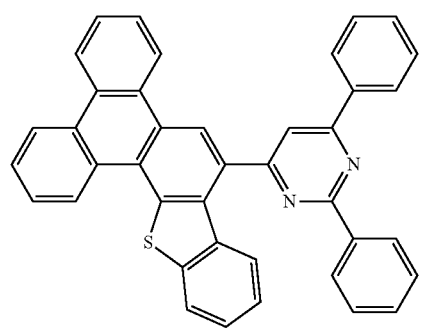 [A-35]
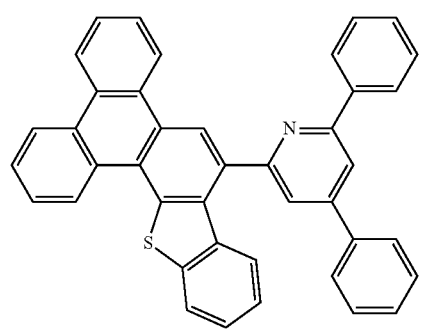 [A-36]
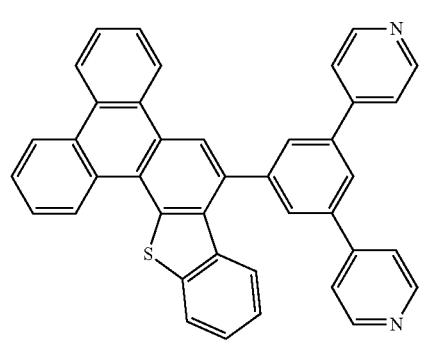 [A-37]
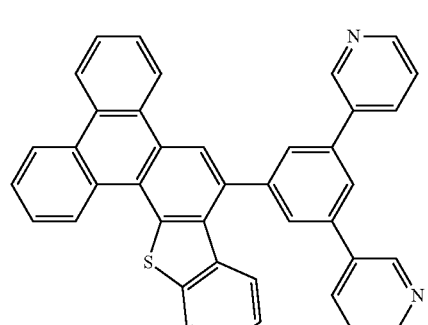 [A-38]
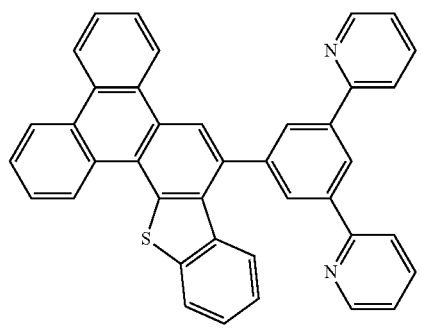 [A-39]
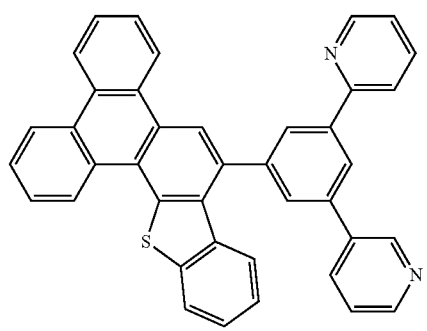 [A-40]
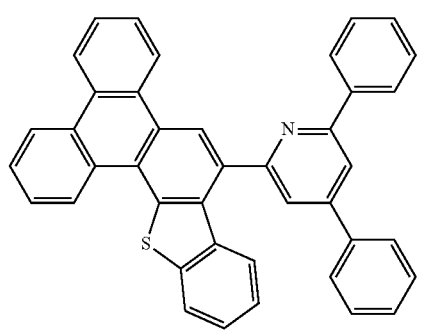 [A41]
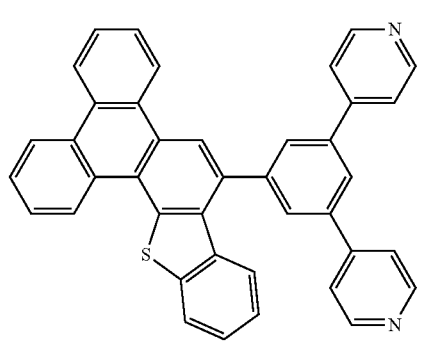 [A42]
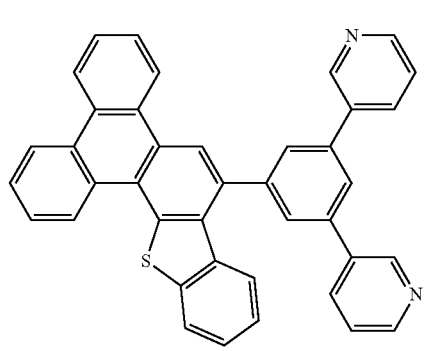 [A-43]

[A-44]
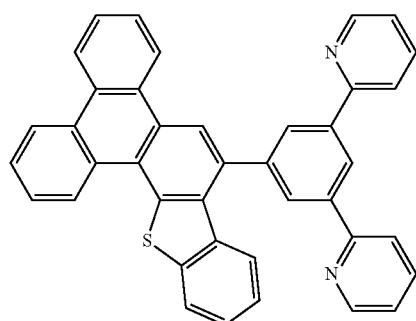
[A-48]
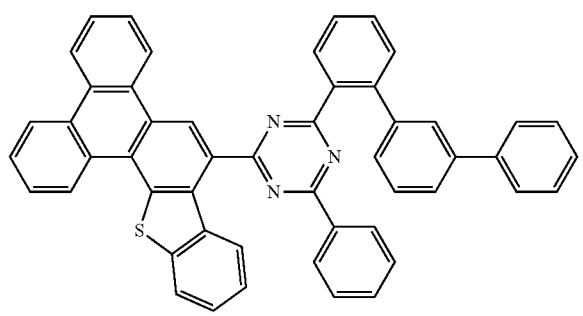
[A-45]
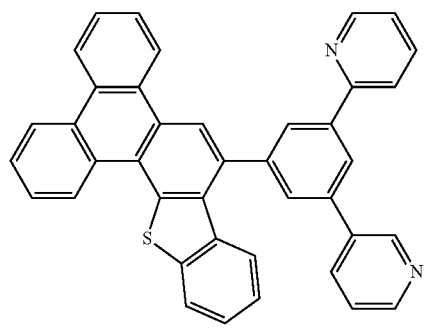
[A-49]
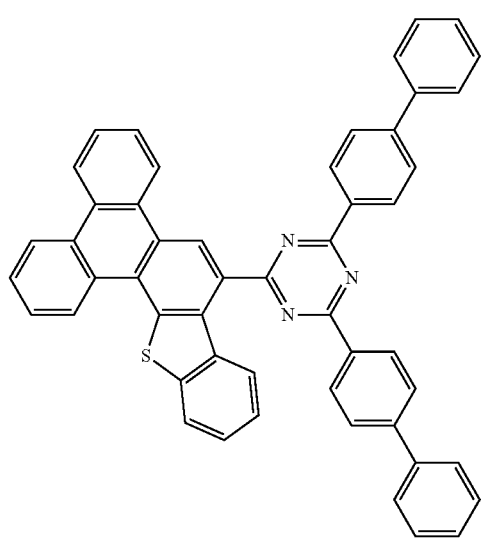
[A-46]
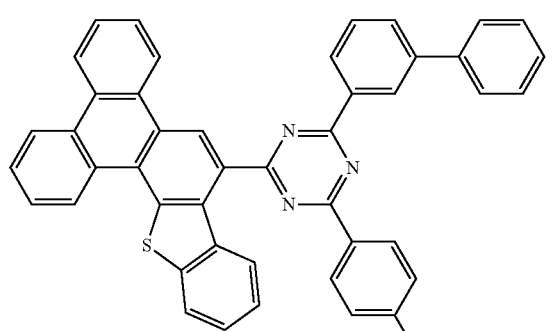
[A-50]
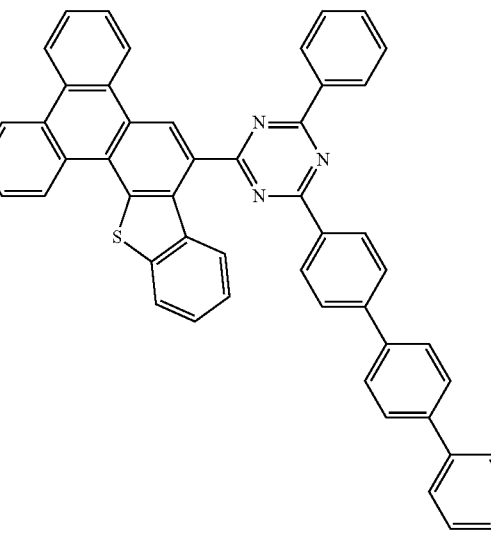
[A-47]
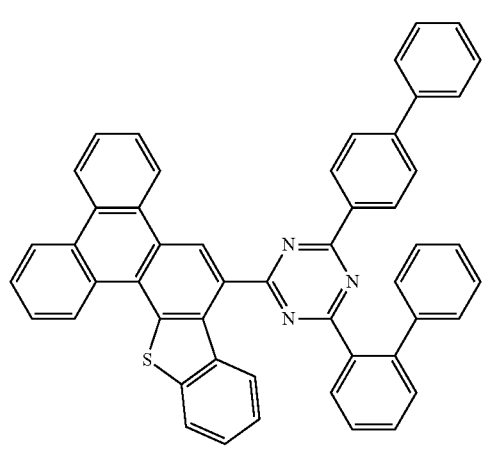

[A-51]
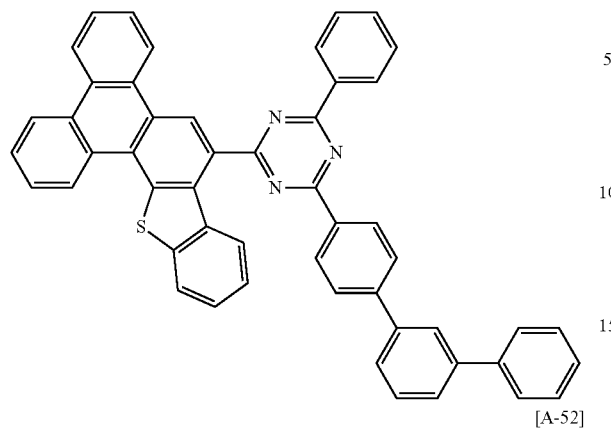
[A-52]
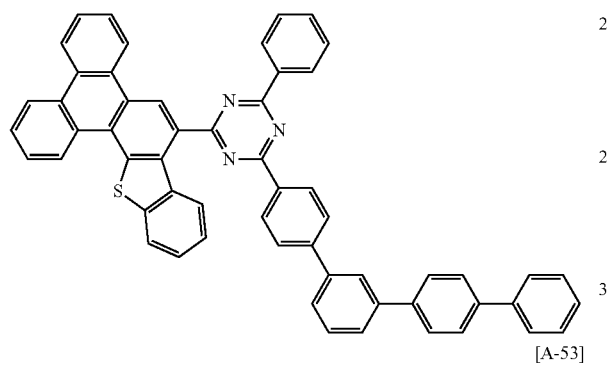
[A-53]
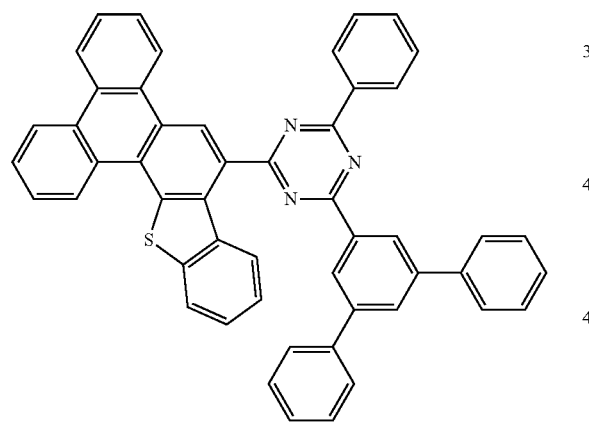
[A-54]
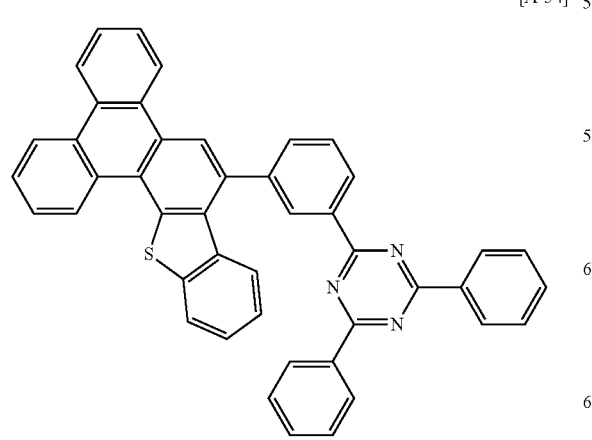
[A-55]
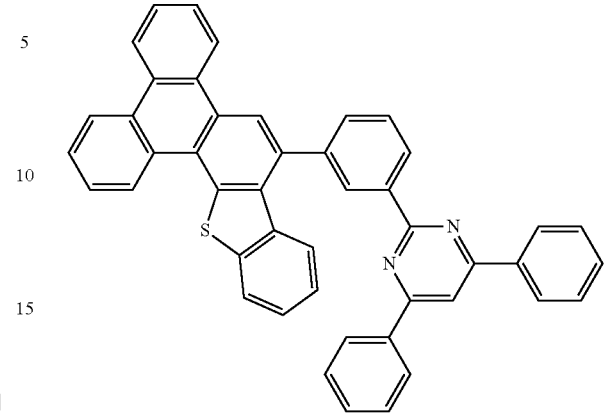
[A-56]
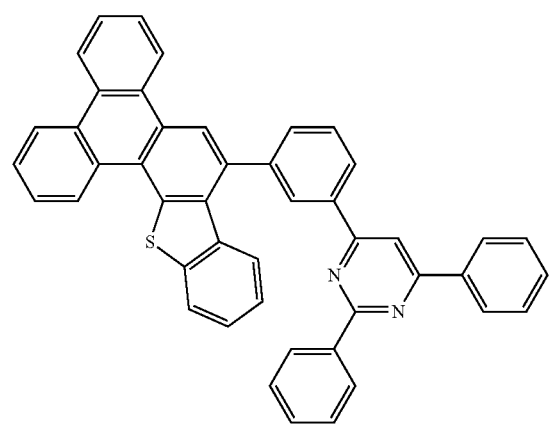
[A-57]
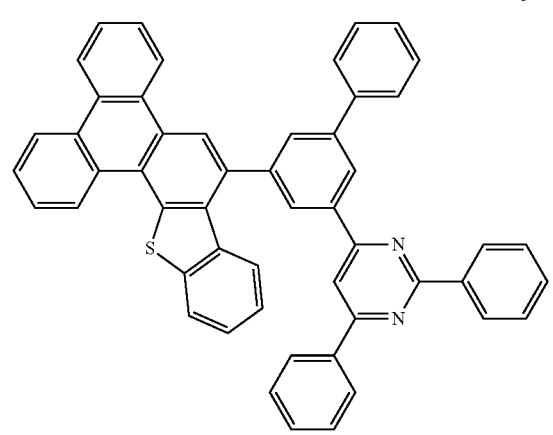

-continued
[A-58]
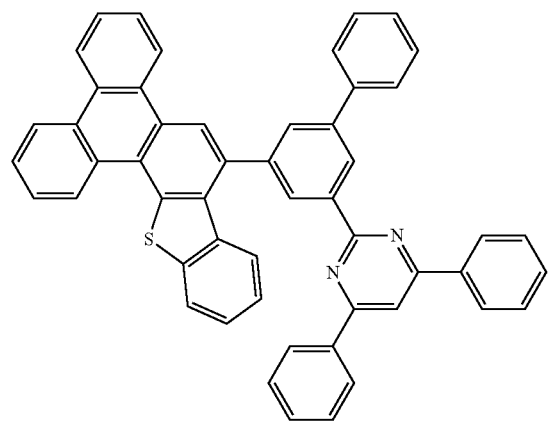
[A-59]
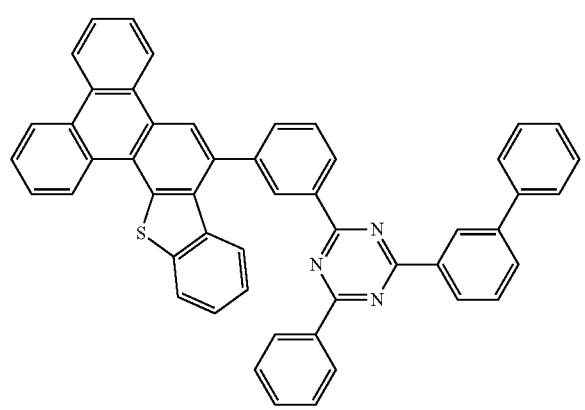
[A-60]
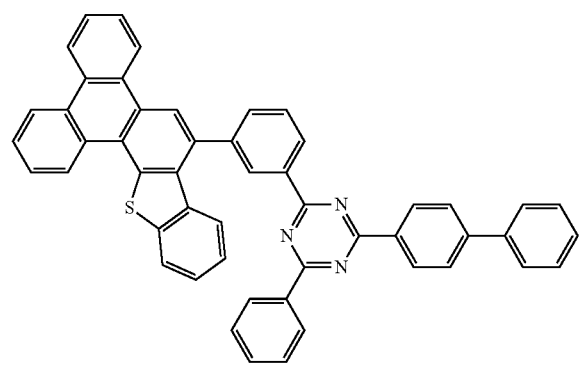
-continued
[A-61]
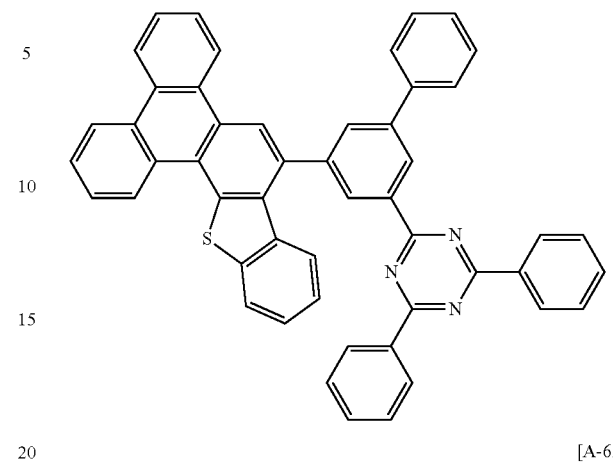
[A-62]
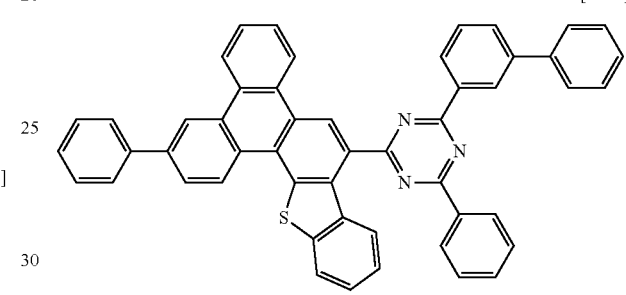
[A-63]
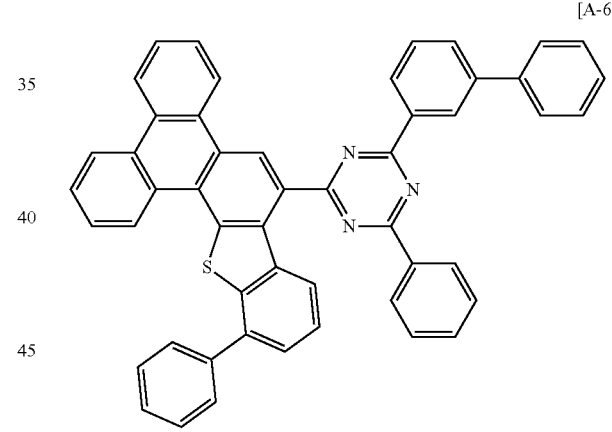
[A-64]
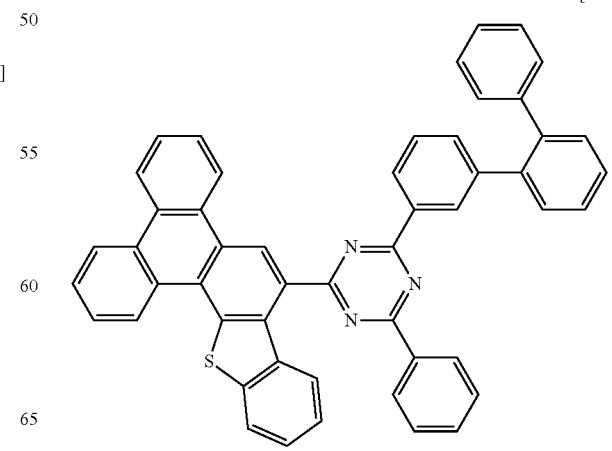

[A-65]
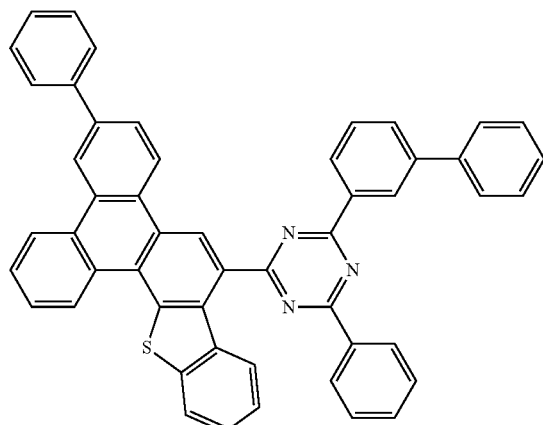
[A-66]
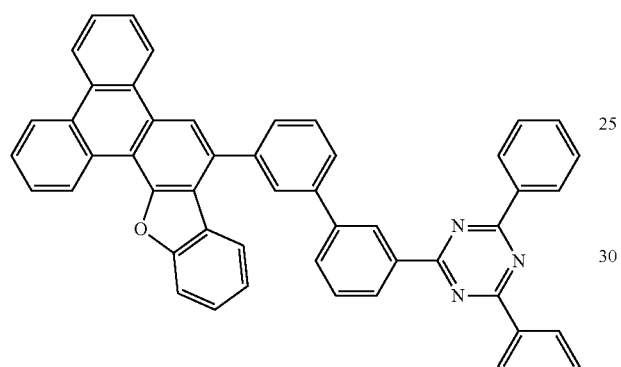
[A-67]
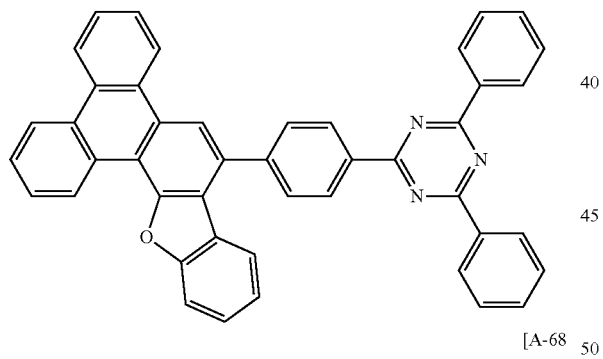
[A-68]
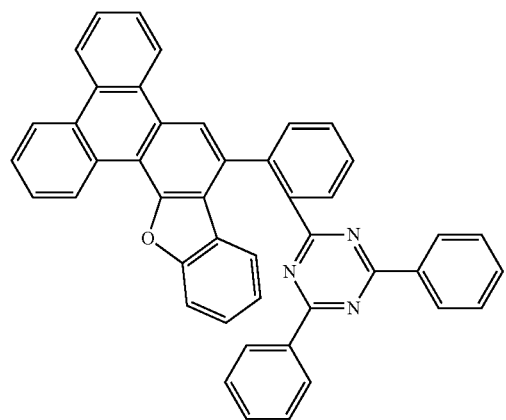
[A-69]
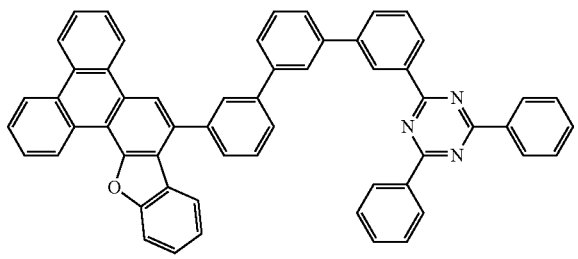
[A-70]
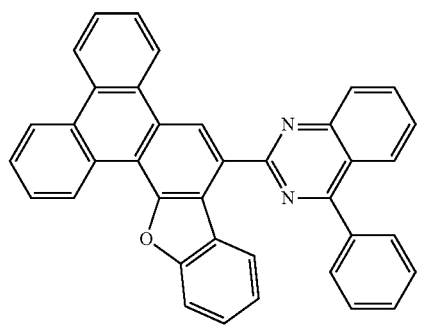
[A-71]
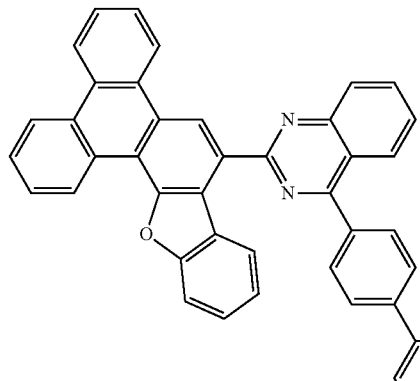
[A-72]
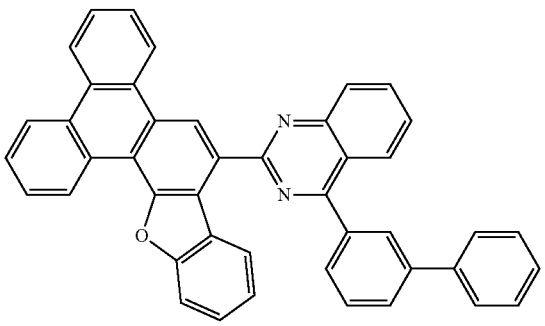

[A-73]
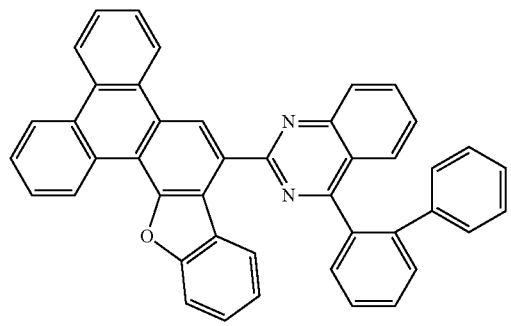
[A-74]
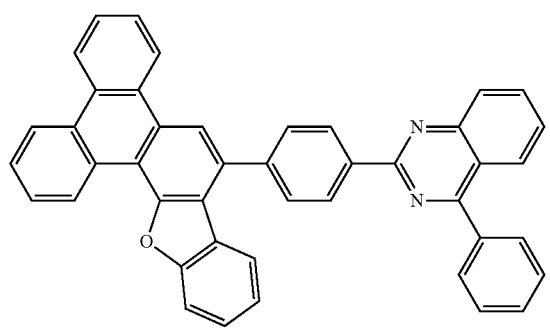
[A-75]
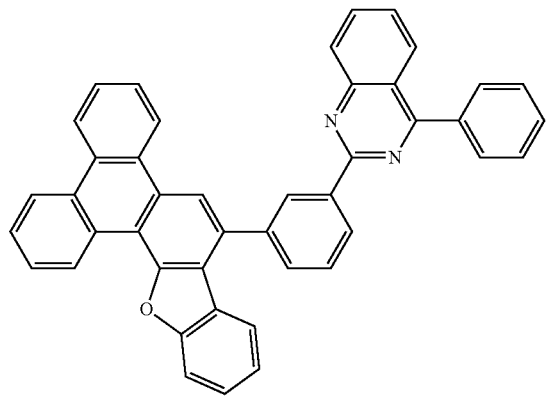
[A-76]
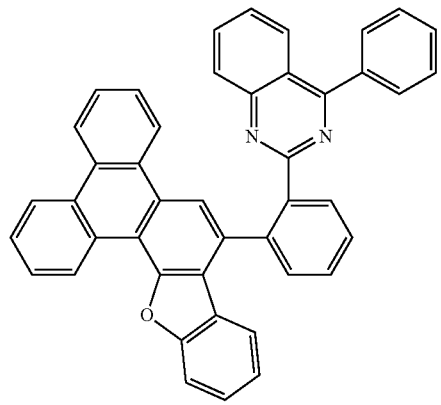
[A-77]
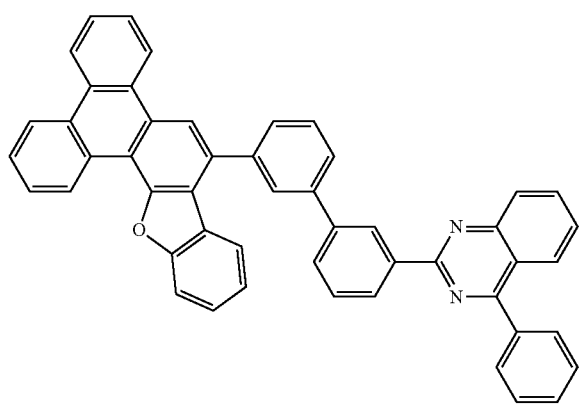
[A-78]
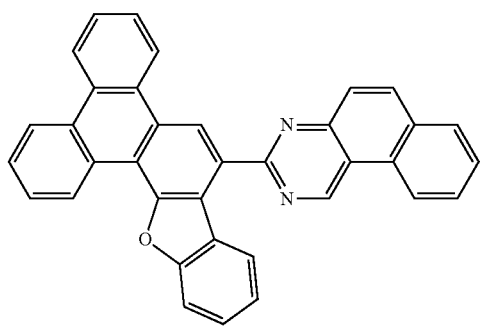
[A-79]
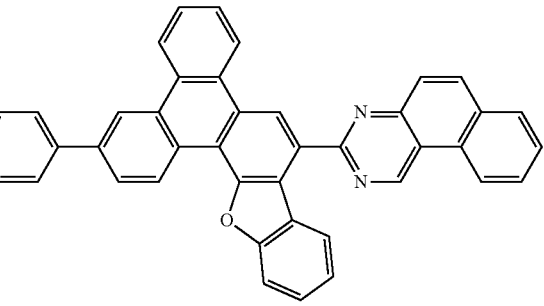
[A-80]
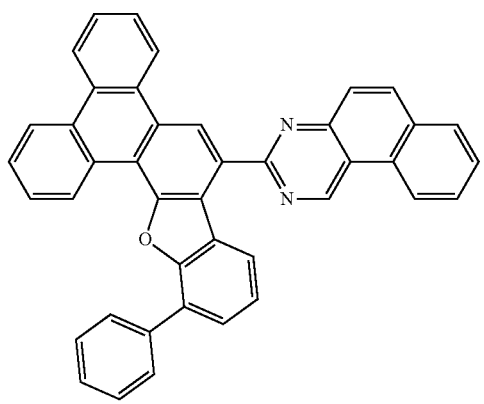

[A-81]

[A-82]

[A-83]

[A-84]

[A-85]

[A-86]

[A-87]

[A-88]

[A-89]
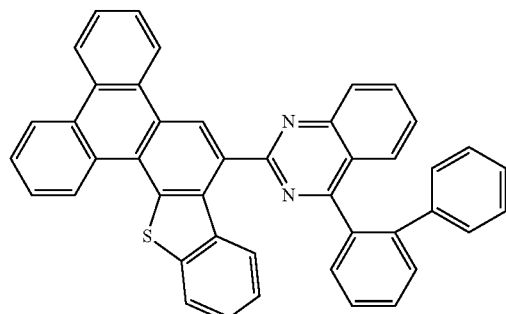
[A-90]
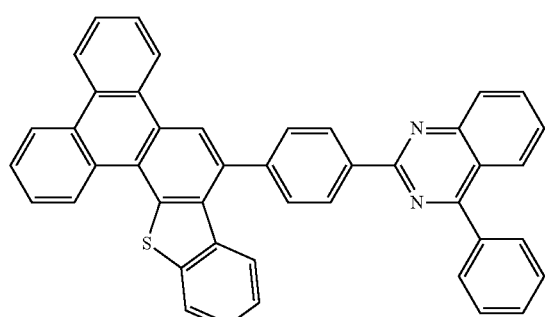
[A-91]
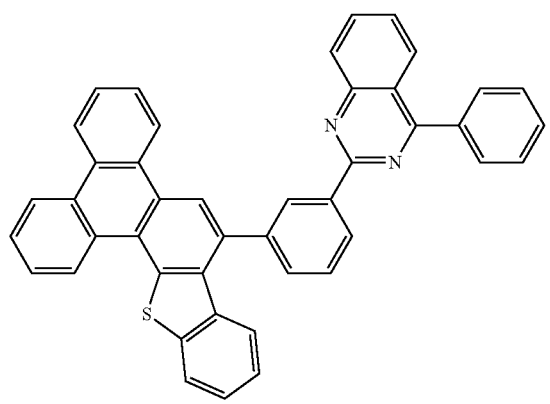
[A-92]
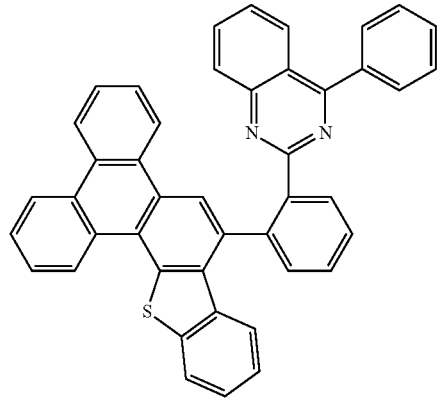
[A-93]
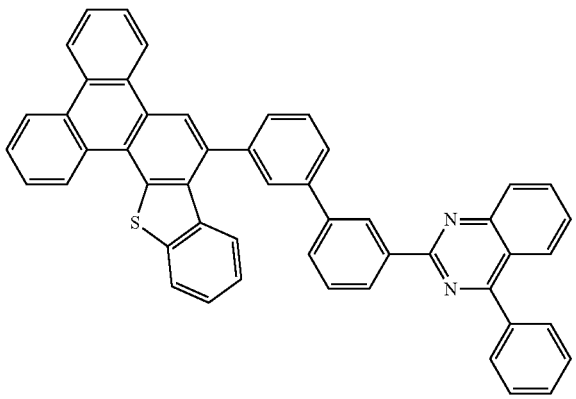
[A-94]
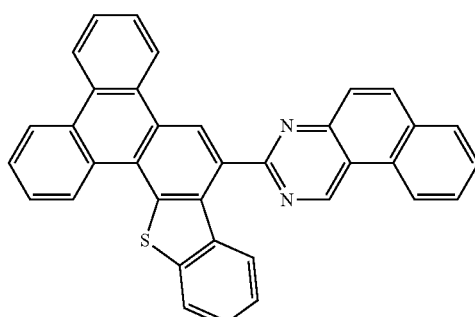
[A-95]
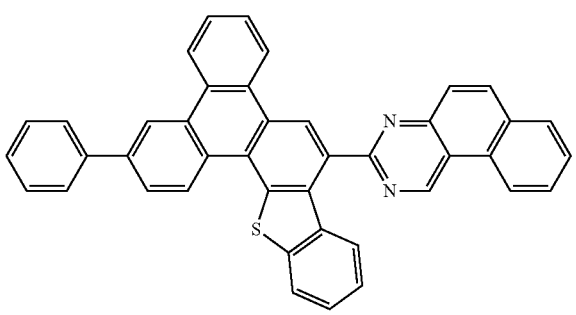
[A-96]
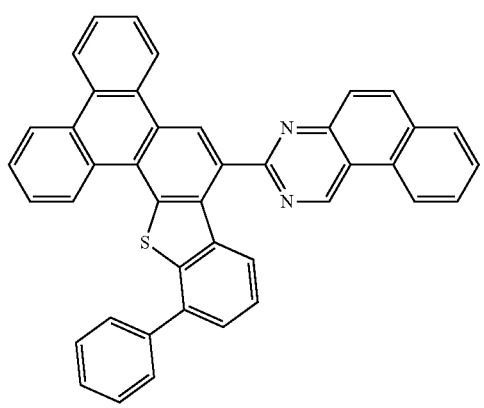

[A-97]
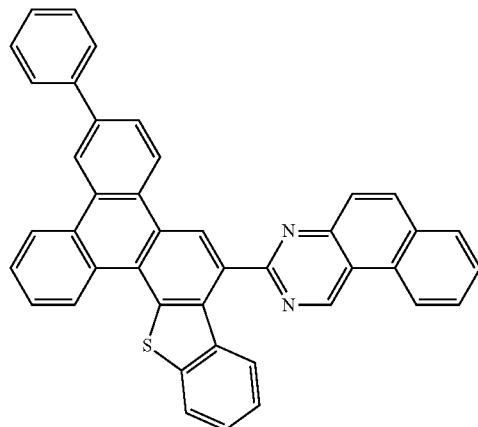
[A-101]
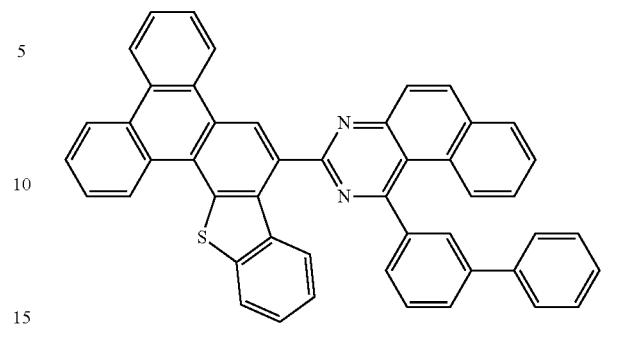
[A-98]
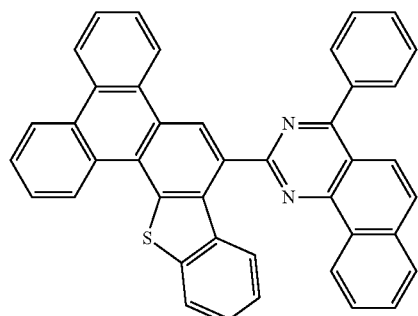
[A-102]
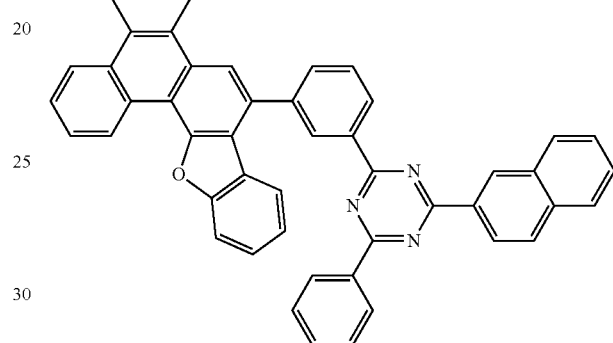
[A-99]
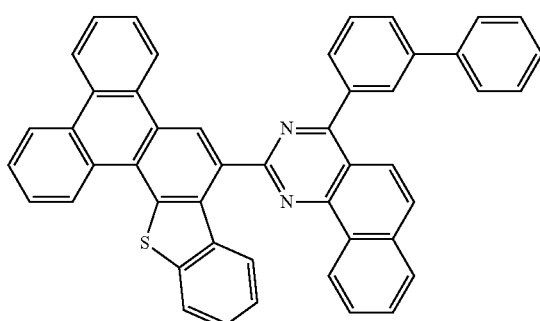
[A-103]
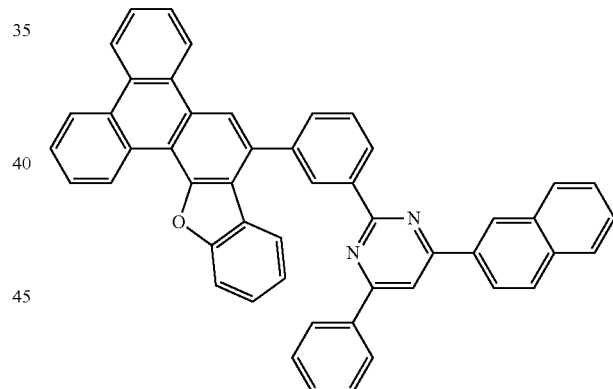
[A-100]
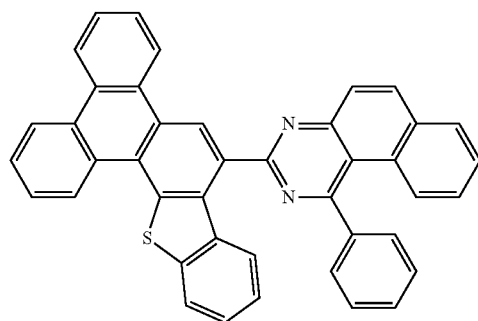
[A-104]
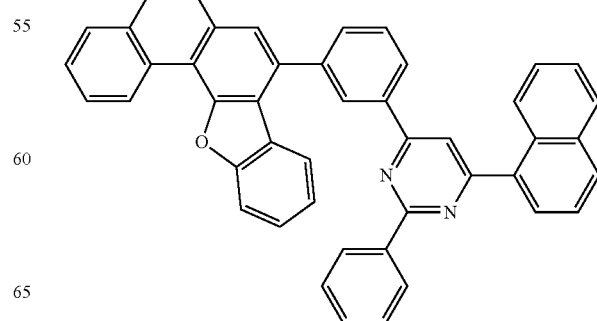

[A-105]
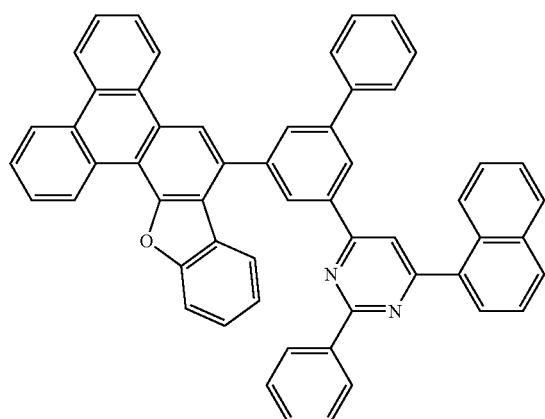
[A-106]
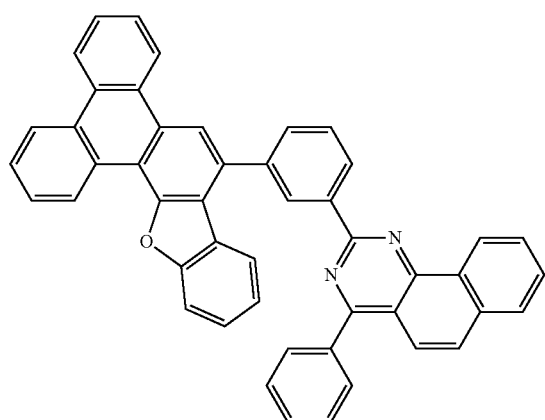
[A-107]
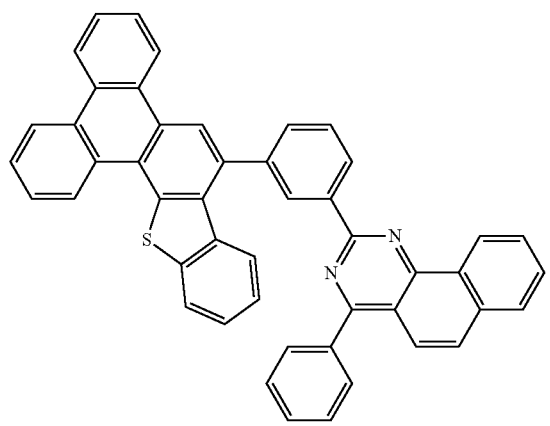
[B-1]
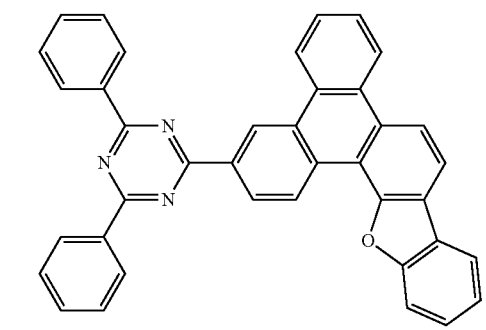
[B-2]
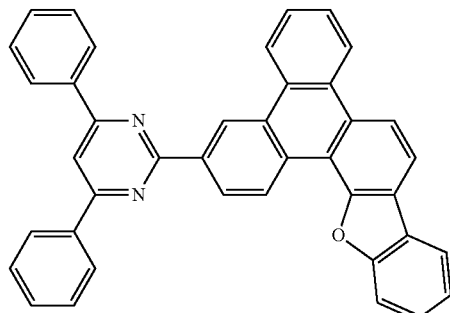
[B-3]
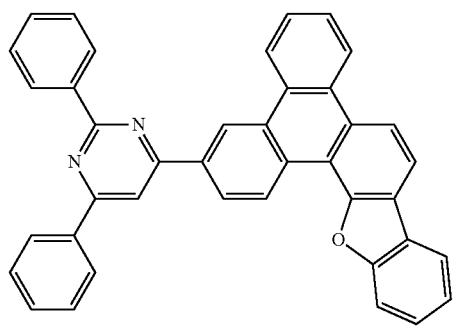
[B-4]
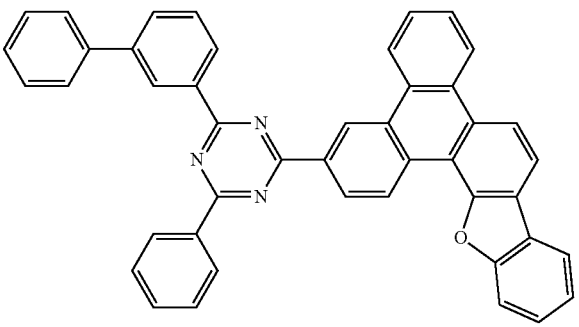
[B-5]
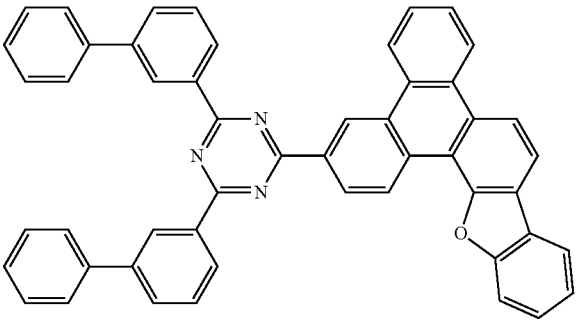

[B-6]
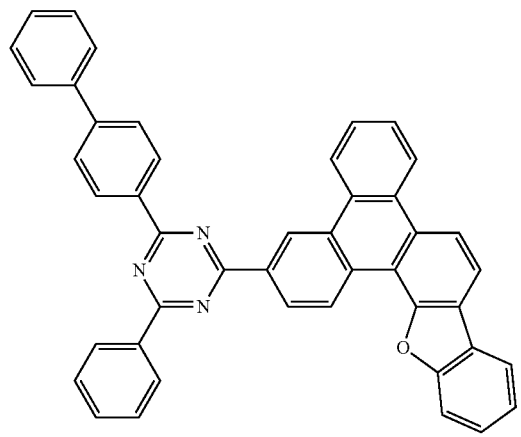
[B-7]
[B-8]
[B-9]
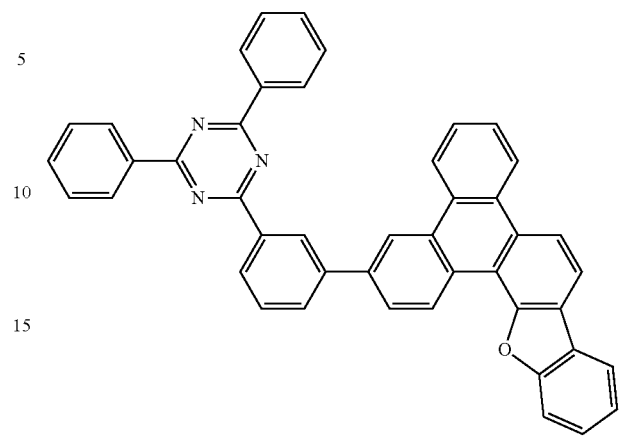
[B-10]
[B-11]
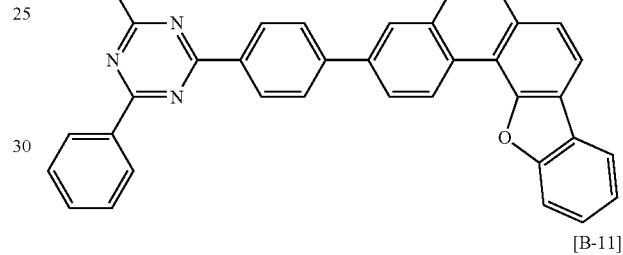
[B-12]
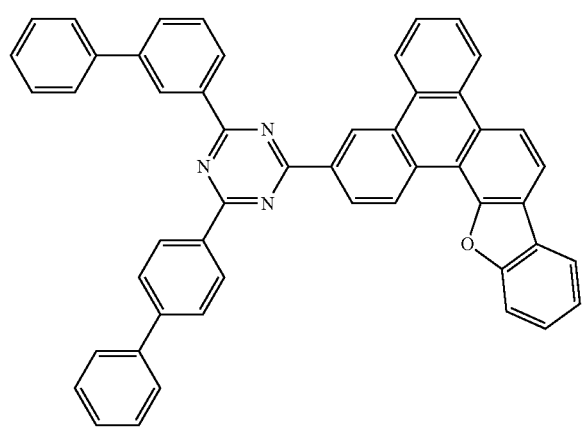
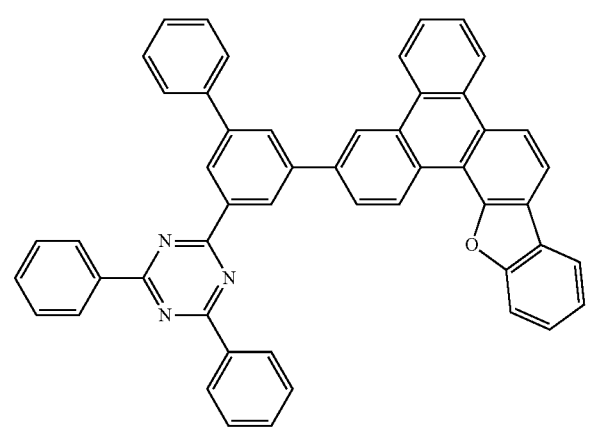

[B-13]
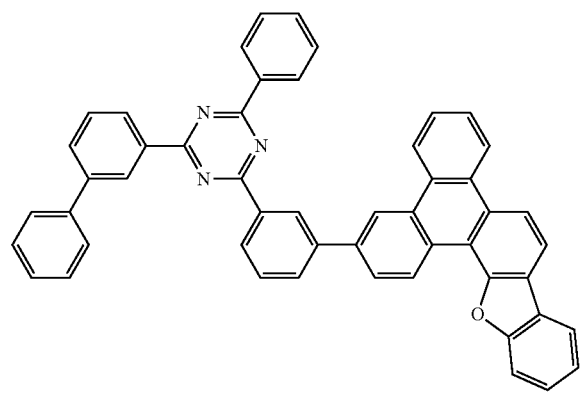
[B-14]
[B-15]
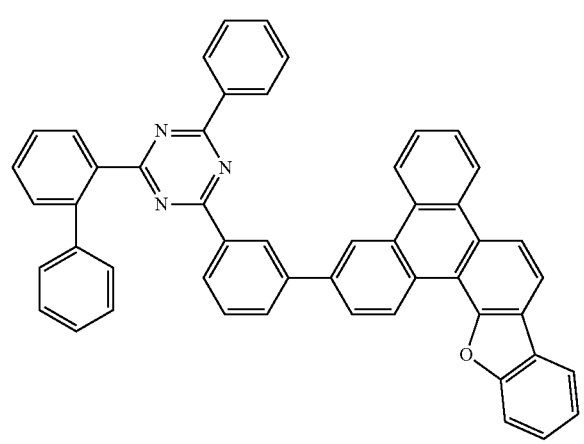
[B-16]
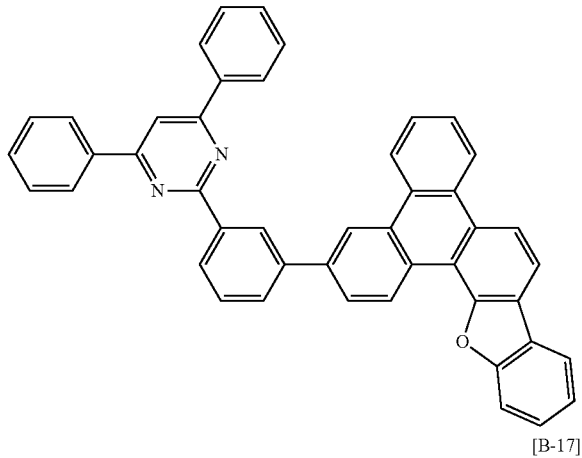
[B-17]
[B-18]
[B-19]
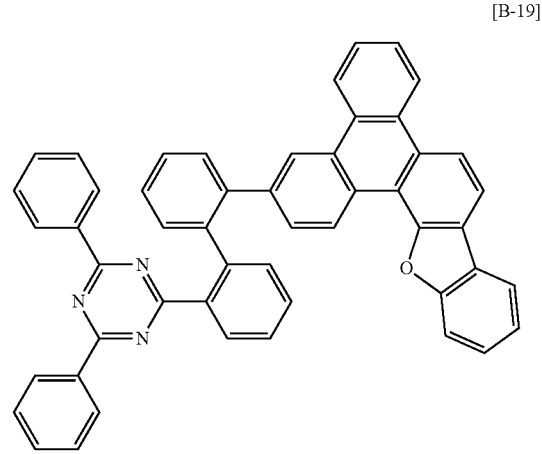

-continued
[B-20]
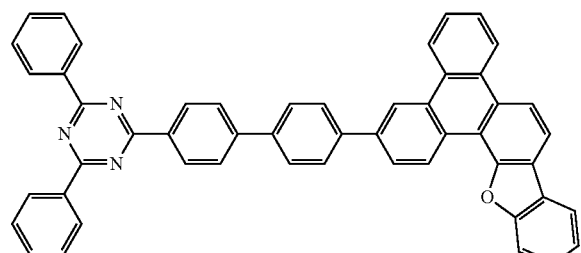
[B-21]
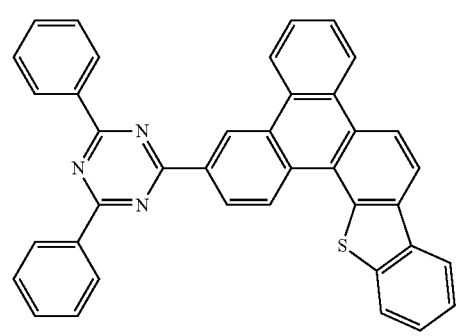
[B-22]
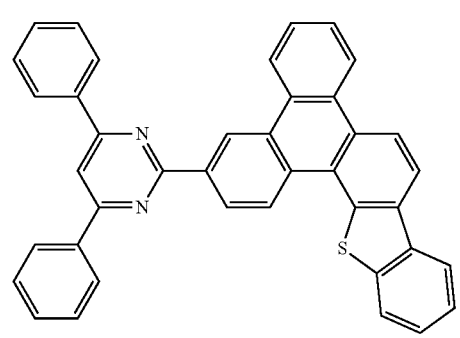
[B-23]
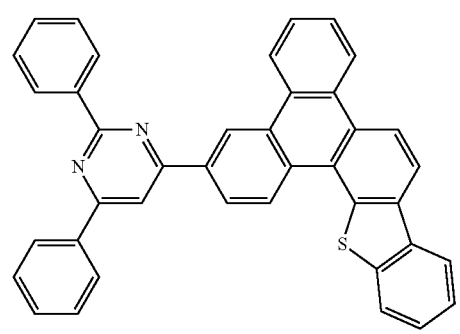
[B-24]
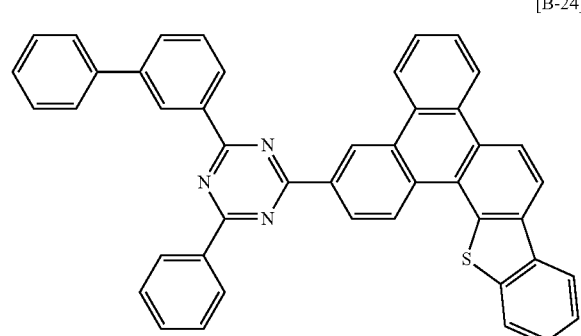
-continued
[B-25]
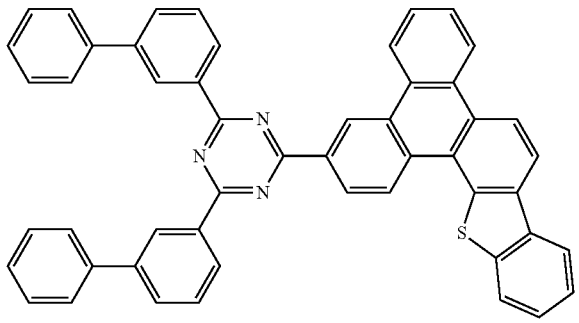
[B-26]
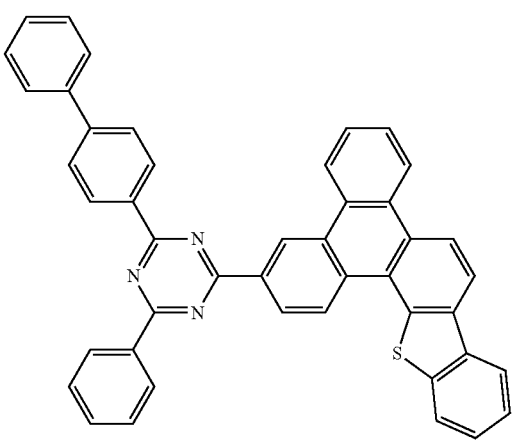
[B-27]
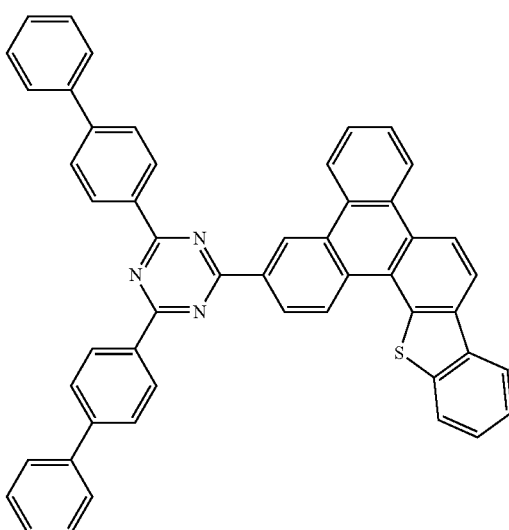

[B-28] 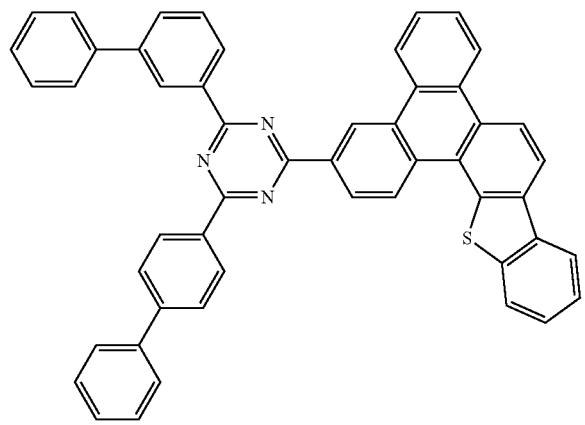
[B-29] 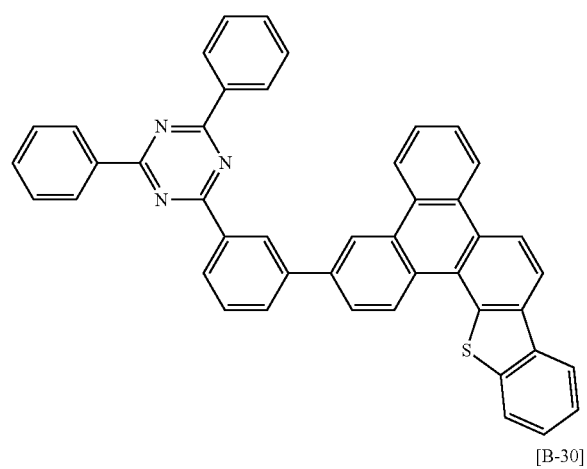
[B-30] 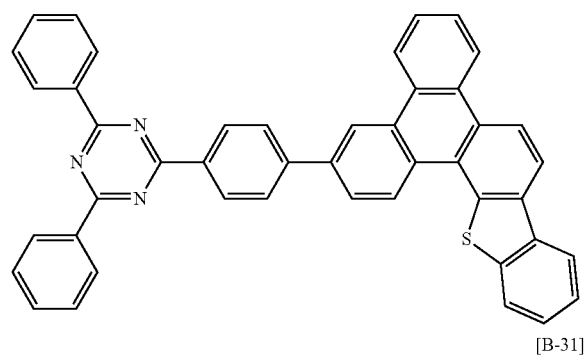
[B-31] 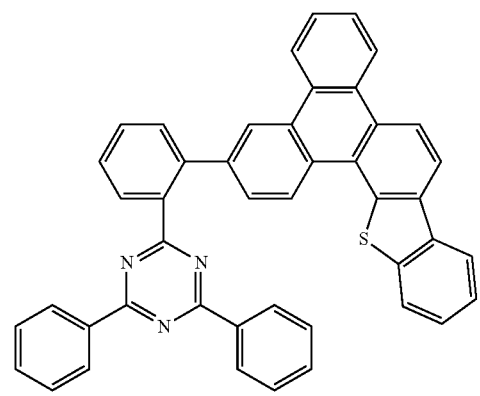
[B-32] 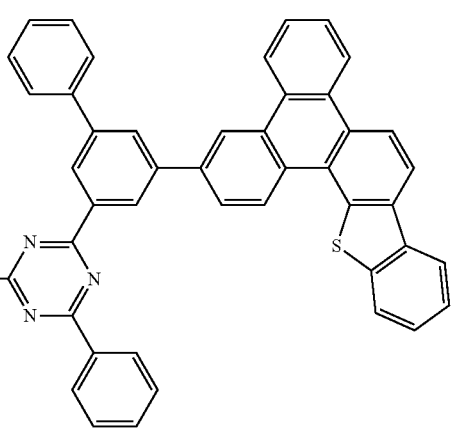
[B-33] 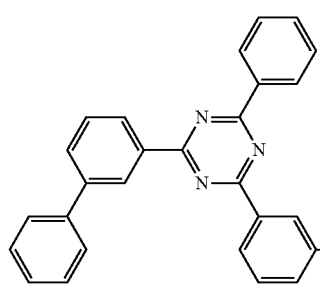
[B-34] 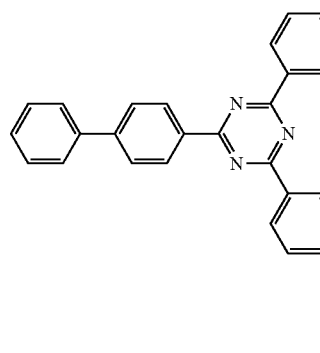

[B-35]
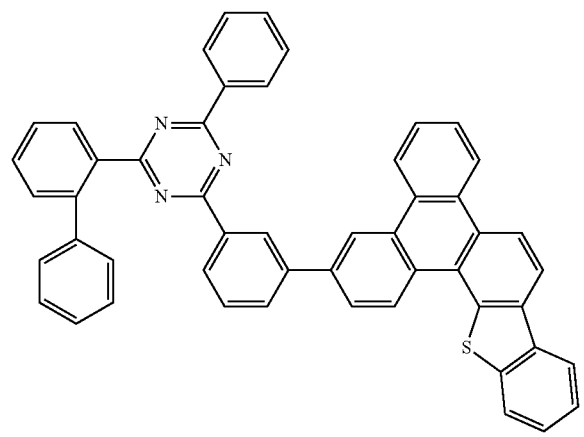
[B-36]
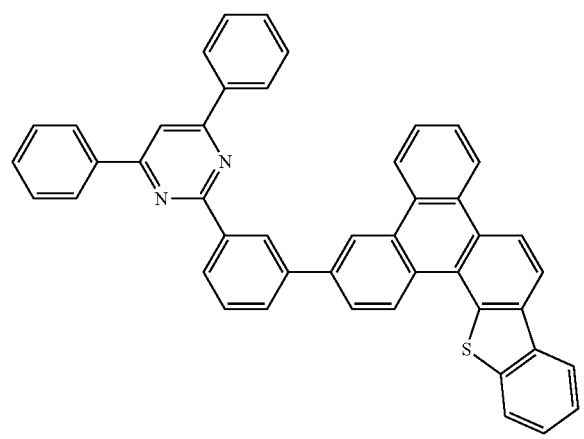
[B-37]
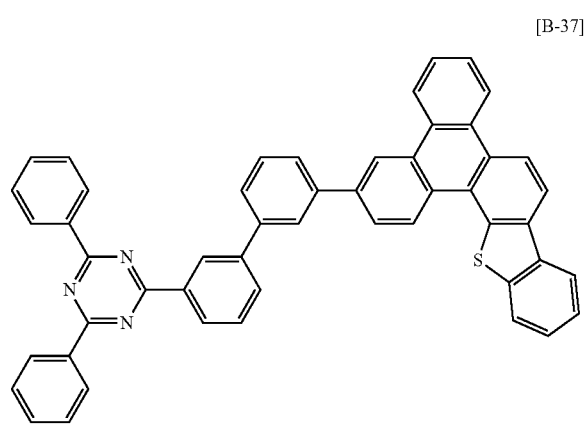
[B-38]
[B-39]
[B-40]
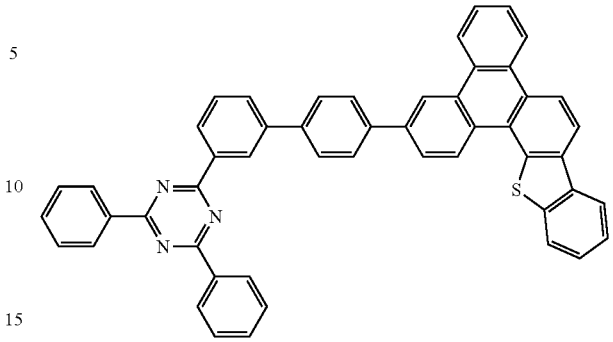
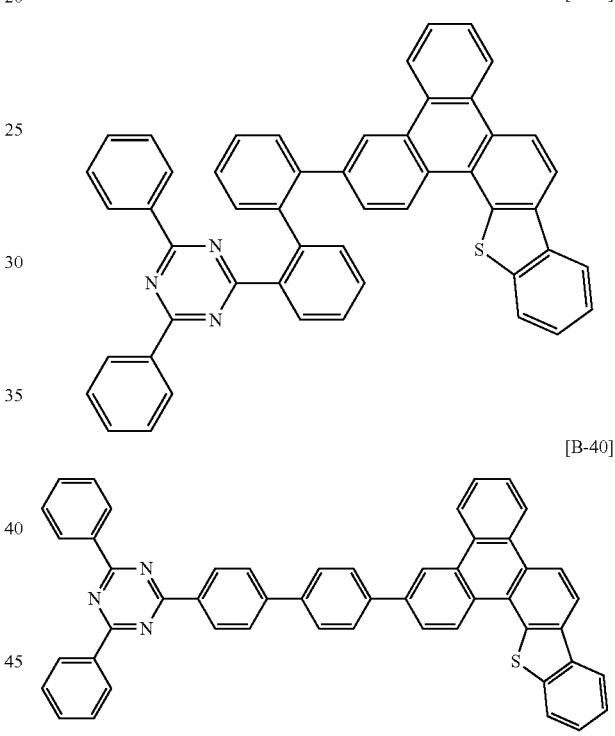
[B-41]
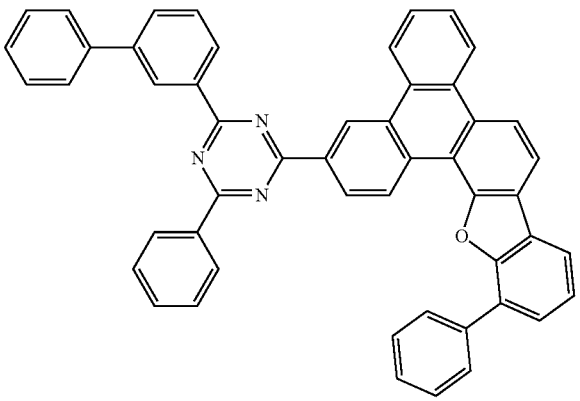

[B-42]
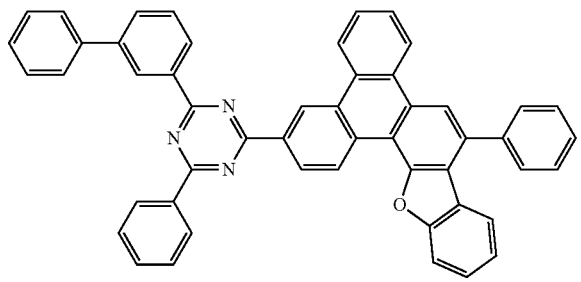
[B-43]
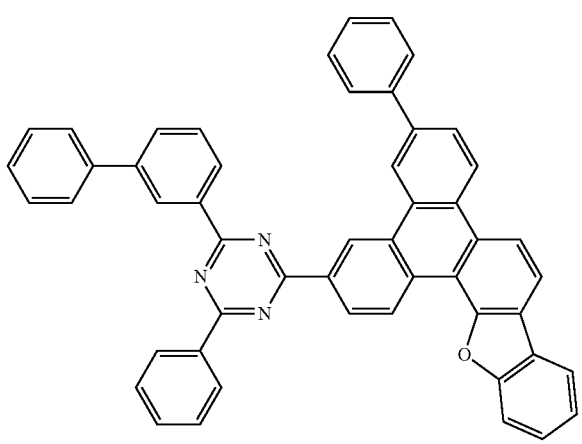
[B-44]
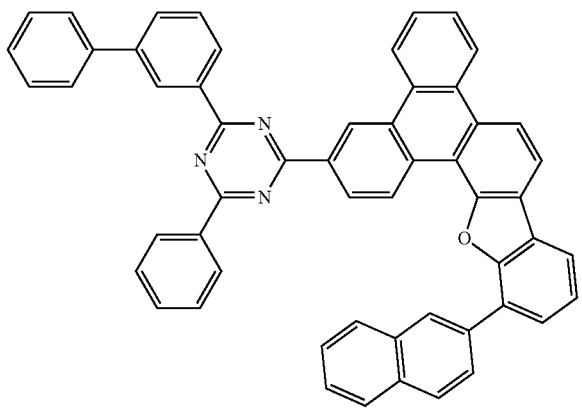
[B-45]
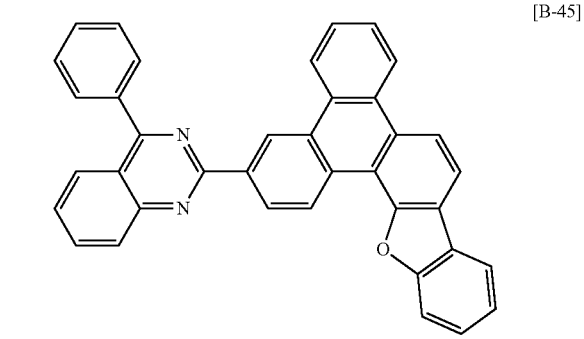
[B-46]
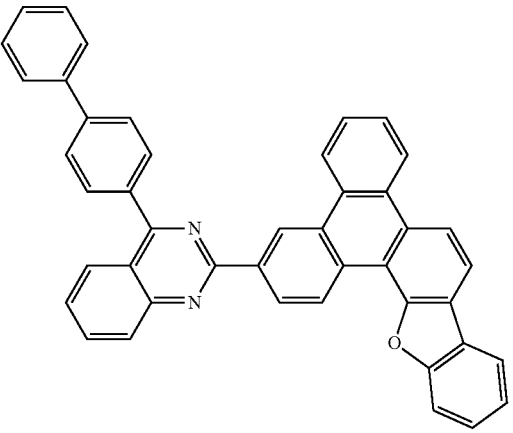
[B-47]
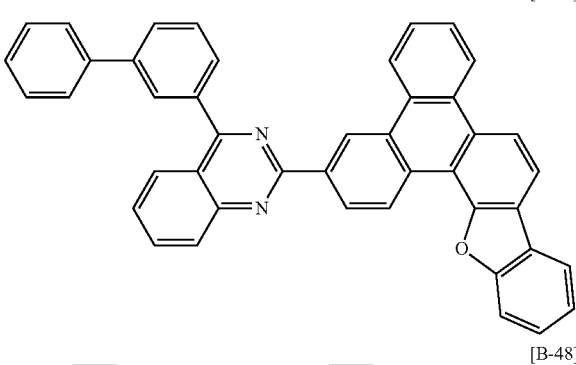
[B-48]
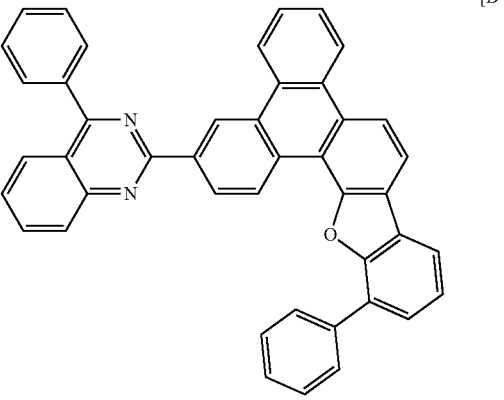
[B-49]
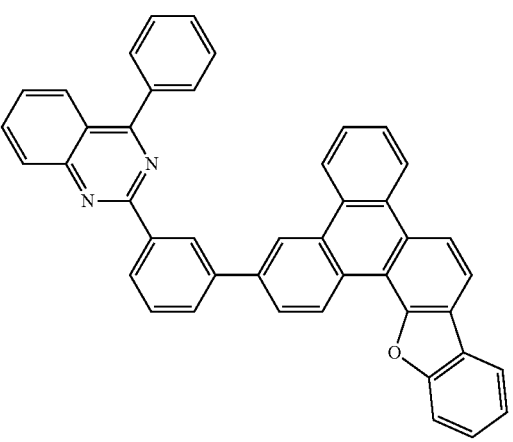

[B-50]
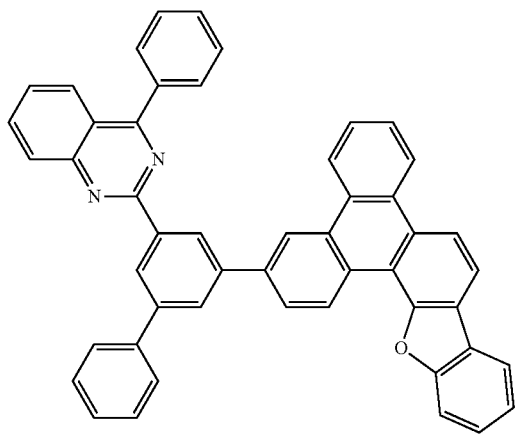
[B-51]
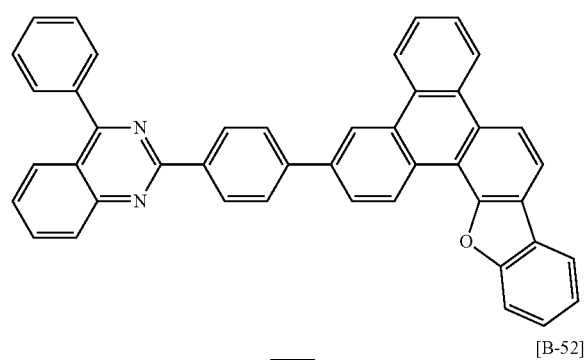
[B-52]
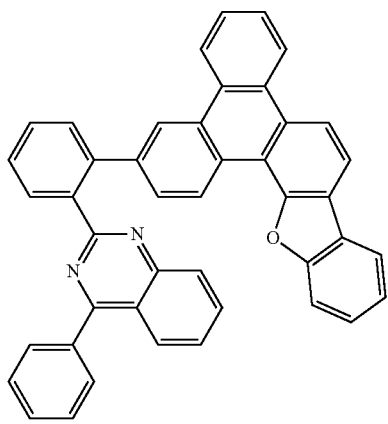
[B-53]
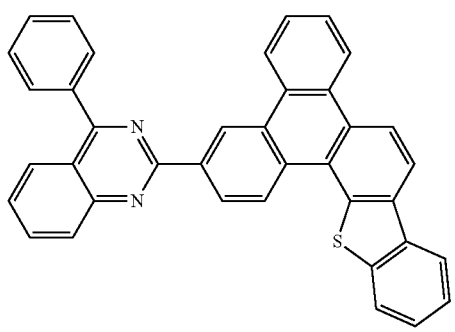
[B-54]
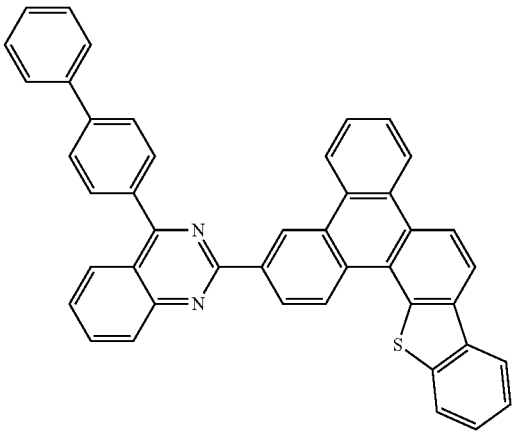
[B-55]
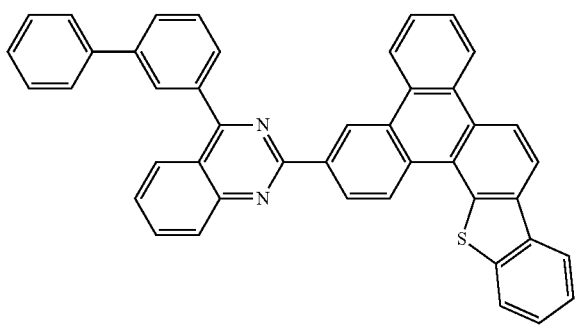
[B-56]
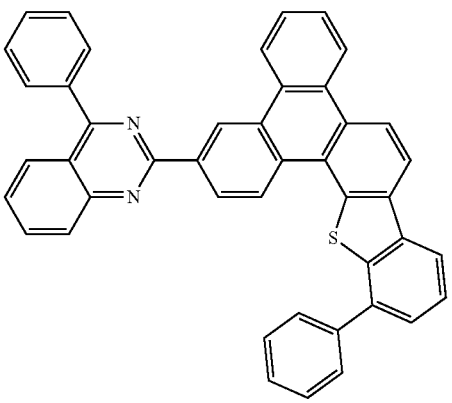
[B-57]
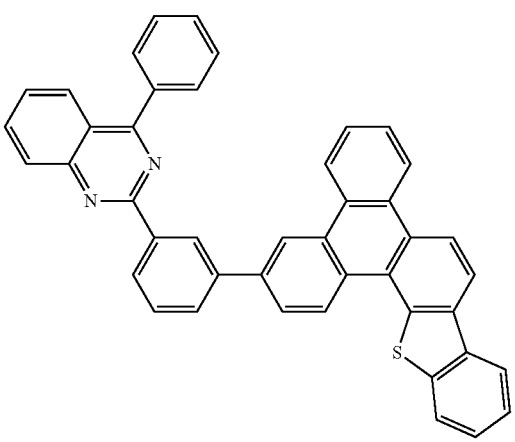

[B-58]

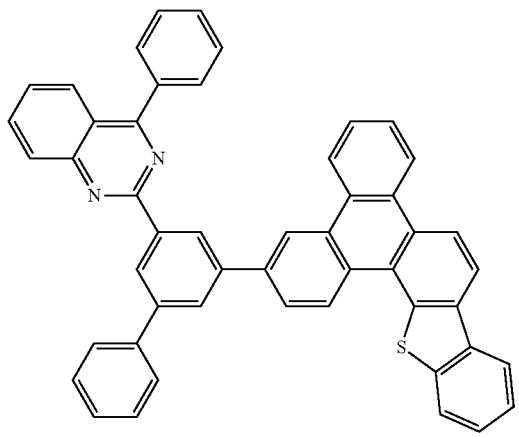

[B-60]

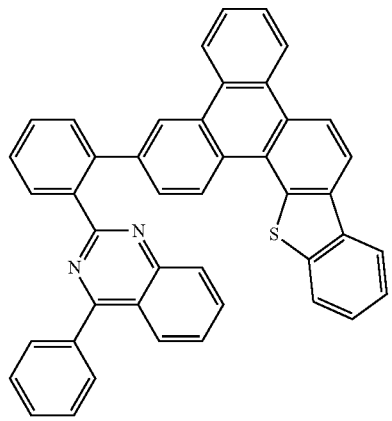

[B-59]

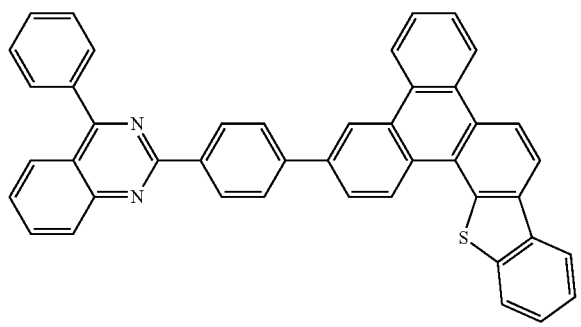

7. An organic optoelectronic device, comprising
an anode and a cathode facing each other, and
at least one organic layer disposed between the anode and the cathode,
wherein the organic layer comprises the compound for an organic optoelectronic device of claim 1.

8. The organic optoelectronic device of claim 7, wherein
the organic layer comprises a light emitting layer, and
the compound for an organic optoelectronic device is included as a host of the light emitting layer.

9. The organic optoelectronic device of claim 8, wherein
the organic layer further comprises at least one auxiliary layer selected from a hole injection layer, a hole transport layer, an electron blocking layer, an electron transport layer, an electron injection layer, and a hole blocking layer,
the auxiliary layer further comprises an electron transport auxiliary layer that is adjacent to the light emitting layer, and
the electron transport auxiliary layer comprises the compound for an organic optoelectronic device.

10. A display device comprising the organic optoelectronic device of claim 7.

* * * * *